United States Patent [19]
Cukierski et al.

[11] Patent Number: 5,872,126
[45] Date of Patent: Feb. 16, 1999

[54] METHODS AND COMPOSITIONS FOR TREATING PRETERM LABOR

[75] Inventors: Mark A. Cukierski, Souderton; Stanley G. Spence, North Wales, both of Pa.; Joanne Waldstreicher, Scotch Plains, N.J.

[73] Assignee: Merck & Co., Inc., Rahway, N.J.

[21] Appl. No.: 920,505

[22] Filed: Aug. 29, 1997

Related U.S. Application Data

[60] Provisional application No. 60/025,519, Sep. 6, 1996.
[51] Int. Cl.$^6$ .................................................. A61K 31/58
[52] U.S. Cl. .................. 514/284; 514/232.5; 514/241; 514/253; 514/254; 514/261
[58] Field of Search ............................. 514/254, 284, 514/253, 241, 261, 232.5

[56] References Cited

U.S. PATENT DOCUMENTS

| | | | |
|---|---|---|---|
| 4,760,071 | 7/1988 | Rasmusson et al. | 514/284 |
| 5,278,159 | 1/1994 | Bakshi et al. | 514/232.5 |
| 5,324,734 | 6/1994 | Gilbert et al. | 514/281 |
| 5,359,071 | 10/1994 | Durette et al. | 546/78 |
| 5,504,116 | 4/1996 | Kao et al. | 514/626 |
| 5,510,351 | 4/1996 | Graham et al. | 514/253 |
| 5,510,485 | 4/1996 | Graham et al. | 544/336 |
| 5,516,799 | 5/1996 | Alliger | 514/557 |
| 5,525,608 | 6/1996 | Adams et al. | 514/284 |
| 5,527,806 | 6/1996 | Holt et al. | 514/284 |
| 5,536,727 | 7/1996 | Witzel et al. | 514/284 |
| 5,565,467 | 10/1996 | Batchelor et al. | 514/284 |
| 5,610,162 | 3/1997 | Witzel et al. | 514/284 |

FOREIGN PATENT DOCUMENTS

| | | | |
|---|---|---|---|
| WO 93/23038 | 11/1993 | WIPO . | |
| WO 93/23039 | 11/1993 | WIPO . | |
| WO 93/23048 | 11/1993 | WIPO . | |
| WO 93/23420 | 11/1993 | WIPO . | |
| WO 94/07861 | 4/1994 | WIPO . | |
| WO 95/00147 | 1/1995 | WIPO . | |
| WO 95/02607 | 1/1995 | WIPO . | |
| 95/11254 | 4/1995 | WIPO | 514/284 |
| WO 95/11254 | 4/1995 | WIPO . | |
| WO 95/28928 | 11/1995 | WIPO . | |
| WO 95/32215 | 11/1995 | WIPO . | |
| WO 96/22100 | 7/1996 | WIPO . | |

OTHER PUBLICATIONS

Myatt et al., Prostaglandins 48:285–296 (1994), "Identification and changes in concentrations of prostaglandin H synthase (PGHS) isoforms in rat myometrium . . . ".

Marrone et al., Endocrinology 109:41–45 (1981), "Progesterone metabolism by the hypothalamus, pituitary, and uterus of the rat during pregnancy".

Benbow et al., Biology of Reproduction 52:1327–1333 (1995), "Distribution and metabolism of maternal progesterone in the uterus, placenta, and fetus during rat pregnancy".

Mahendroo, Molecular Endocrinology 10:380–392 (1996), "5alpha–reducted androgens play a key role in murine parturition".

Abdellilah et al., J. Pharmacol. & Exper. Therapeutics 265(3):1205–1212 (1933), "Progesterone and mifepristone modify principally the responses of circular myometrium to oxytocin in preparturient rats . . . ".

Casey et al., Progress in Endocrinology, The proceedings of the 9th Int'l Congress of Endocrinology, Nice 1992, pp. 638–643, "Human parturition: prostaglandins and cytokines are sequelae of labor".

Flint et al., Endocrinology 92:624–627 (1973), "The appearance of an endometrial 20alpha–hydroxysteroid dehydrogenase towards the end of pregnancy in the rat".

Howard et al., Steroids 19:35–45 (1972), "Progesterone metabolism by uterine tissue of pregnant rats".

Benlow et al, Biology of Reproduction, vol. 52, pp. 1327–1333, 1995.

Flint et al, Endocrinology, vol. 92, pp. 624–627, 1973.

Howard et al, Steroids, vol. 19, pp. 35–45, 1972.

Marrone et al, Partuition in Mammals and Man, Thibault et al Eds), pp. 481–501, 1993.

Myatt et al, Prostaglandins, vol. 48, pp. 285–296, 1994.

*Primary Examiner*—James H. Reamer
*Attorney, Agent, or Firm*—Catherine D. Fitch; Melvin Winokur

[57] ABSTRACT

The present invention provides for a method of treating preterm labor in a subject in need of such treatment comprising administration of a therapeutically effective amount of an inhibitor of 5α-reductase type 1 to the subject. The present invention further provides for a method of preventing premature labor in a subject susceptible thereto comprising administration of a labor-preventive amount of an inhibitor of 5α-reductase type 1 to the subject. Further, the present invention also relates to a method of reducing the risk of premature labor in a subject at risk therefor. The present invention also provides for a method for stopping labor preparatory (i.e., prior) to Cesarean delivery in a subject in need of such treatment comprising administration of a therapeutically effective amount of an inhibitor of 5α-reductase type 1 to the subject.

Further, the present invention provides for compositions useful in the methods of the present invention, as well as a method of manufacture of a medicament useful for treating pre-term labor and for stopping labor preparatory to Cesarean delivery.

23 Claims, No Drawings

METHODS AND COMPOSITIONS FOR TREATING PRETERM LABOR

CROSS REFERENCE TO RELATED APPLICATIONS

The present application claims priority of U.S. Provisional Application Ser. No. 60/025,519, filed Sep. 6, 1996, now abandoned.

FIELD OF THE INVENTION

The present invention provides for a novel method of treating preterm labor, a method for stopping labor preparatory (i.e., prior) to Cesarean delivery, a method for preventing preterm labor, and a method of controlling the timing of parturition to effect delivery of farm animals during daylight hours. The present invention also provides for a method of manufacture of a medicament useful for treating preterm labor and for stopping labor preparatory to Cesarean delivery, and for compositions useful in the methods of treating and preventing preterm labor, stopping labor prior to Cesarean delivery and controlling the timing of parturition of farm animals.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include β2-adrenergic agonists, magnesium sulfate and ethanol. In addition, oxytocin receptor antagonists are in development. Ritodrine, the leading β2-adrenergic agonist, causes a number of cardiovascular and metabolic side effects in the mother, including tachycardia, increased renin secretion, hyperglycemia (and reactive hypoglycemia in the infant). Other β2-adrenergic agonists, including salbutamol, terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

The present invention may also be used to stop labor preparatory to Cesarean delivery.

The enzyme 5α-reductase catalyzes the reduction of testosterone (T) to the more potent androgen, 5α-dihydrotestosterone (dihydrotestosterone" or DHT), as shown below:

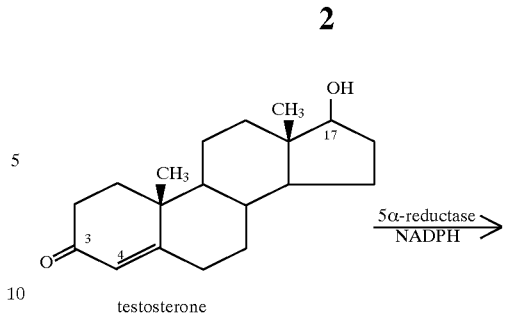

testosterone

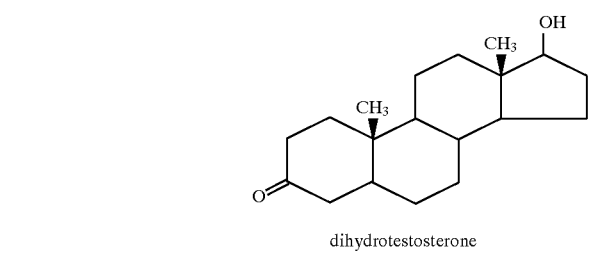

dihydrotestosterone

5α-reductase also catalyzes the reduction of progesterone to dihydroprogesterone, as shown below:

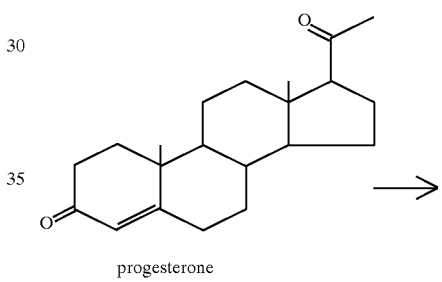

progesterone

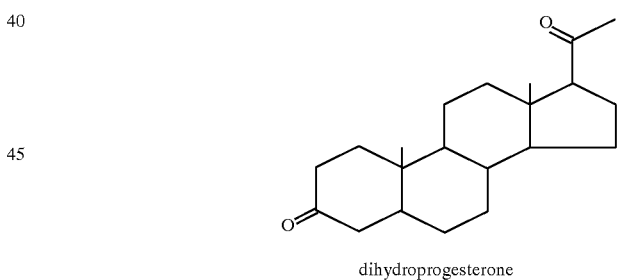

dihydroprogesterone and the reduction of androstenedione to androstanedione, as shown below:

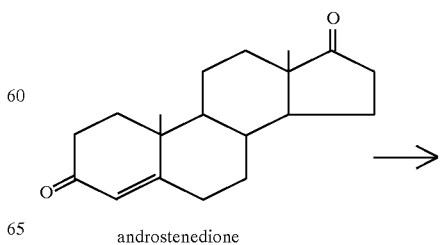

androstenedione

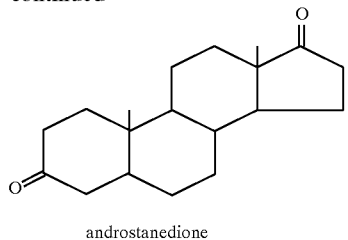

androstanedione

There are two isozymes of 5α-reductase in humans. One isozyme (type 1) predominates in the sebaceous glands of facial skin and skin tissue. The other (type 2) predominates in the prostate.

Finasteride (17β-(N-tert-butylcarbamoyl)-3-oxo-4-aza-5α-androst-1-en-3-one, as shown below, is a potent inhibitor of the human type 2 enzyme.

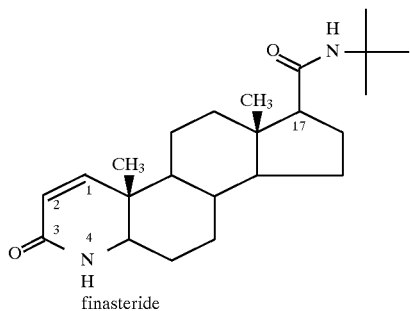

finasteride

Under the tradename PROSCAR®, finasteride is known to be useful in the treatment of hyperandrogenic conditions, see e.g., U.S. Pat. No. 4,760,071. Finasteride is currently prescribed for the treatment of benign prostatic hyperplasia (BPH), a condition affecting to some degree the majority of men over age 55. Finasteride's usefulness in the treatment of androgenic alopecia and prostatic cancer is described in the following documents: EP 0 285 382, published 5 Oct., 1988, EP 0 285 383, published 5 Oct., 1988 and Canadian patents 1,302,277 and 1,302,276.

Inhibitors of 5α-reductase type 1 have also been described. See, e.g., U.S. Pat. No. 5,527,807, issued Jun. 18, 1996, WO 93/23420, published Nov. 25, 1993, U.S. Pat. No. 5,510,351, issued Apr. 23, 2013, WO 93/23038, published Nov. 25, 1993, WO 93/23048, published Nov. 25, 1993, WO 93/23041, published Nov. 25, 1993, WO 93/23040, published Nov. 25, 1993, WO 93/23039, published Nov. 25, 1993, U.S. Pat. No. 5,510,485, issued Apr. 23, 1996, WO 94/07861, published Apr. 14, 1994, U.S. Pat. No. 5,359,071, issued Oct. 25, 1994, WO 95/11254, published Apr. 27, 1995, WO 95/00147, published Jan. 5, 1995, WO 95/28928, published Nov. 2, 1995, U.S. Pat. No. 5,516,799, issued May 14, 1996, U.S. Pat. No. 5,278,159, issued Jan. 11, 1994, U.S. Pat. No. 5,324,734, issued Jun. 28, 1994, WO 95/02607, published Jan. 26, 1995, WO 95/32215, published Nov. 30, 1995, WO 96/22100, published Jul. 25, 1996.

Also known are compounds which are potent inhibitors of both 5α-reductase type 1 and type 2. These include the compounds described in WO 95/12398, published May 11, 1995, WO 95/07926, published Mar. 23, 1995, and WO 95/07927, published Mar. 23, 1995.

RU-486, also known as mifepristone, is known to be a progesterone antagonist. Abdellilah et al., in Progesterone and Mifepristone modify principally the response of circular myometrium to oxytocin in preparturient rats: comparison with response to acetylcholine and to calcium, J. Pharmacol. and Exp. Therp. 265(3):1205–1212 (1993), report that an oral dose of 10 mg/kg of RU-486 on GD 21 was able to induce parturition in pregnant rats treated with 200 mg/kg progesterone subcutaneously.

Mahendroo et al., in 5α-reduced androgens play a key role in murine parturition, Molecular Endocrinology 10:380–92 (1996) describe a study involving mice homozygous for genetic null mutations of type 1 5α-reductase. Seventy percent of these mice failed to initiate parturition. In those studies, the serum progesterone levels in the homozygous mutated mice were not markedly different from wild type mice during the later part of pregnancy. Administration of the progesterone antagonist RU-486 was able to induce parturition in 100% of the mice homozygous for genetic null mutations of type 1 5α-reductase. In addition, administration of 5α-androstan-3α,17β-diol (3α-Adiol) was able to induce parturition in 93% of the homozygous mutated mice.

Benbow and Waddell, in Distribution and Metabolism of Maternal Progesterone in the Uterus, Placenta, and Fetus during Rat Pregnancy, Biology of Reproduction 52:1327–1333 (1995) report that in the rat, plasma progesterone concentration decreases substantially during the last six days of pregnancy.

Flint and Armstrong, in The appearance of an endometrial 20α-hydroxysteroid dehydrogenase towards the end of pregnancy in the rat, Endocrinology 92:624–627 (1973) describe that in the rat the activity of 5α-reductase was low at days 14–16 and increased 2.5-fold before the end of pregnancy, and that the activity of 20α-hydroxy-steroid dehydrogenase increased 3.5-fold during the latter half of gestation. They note that the decrease in peripheral plasma progesterone concentration occurring on day 21 of gestation in the rat has been implicated as a possible cause of the onset of labor.

Howard and Weist, in Progesterone metabolism by uterine tissue of pregnant rats, Steroids 19:35–45 (1972) observed a tenfold increase in metabolic activity of progesterone between day 11 and day 21 of pregnancy when the results were expressed as nanograms of progesterone metabolized per gram of tissue per hour.

Maltier et al. (Parturition in Reproduction in Mammals and Man. Thibault et al (Eds.) Elllipses Publishing, Paris 1993; pp.: 481–501) discuss parturition and note that at the end of pregnancy, the progesterone/oestradiol-17β ratio decreases by 40% in the myometrium.

Marrone and Karavolas, in Progesterone metabolism by the hypothalamus, pituitary, and uterus of the rat during pregnancy, Endocrinology 109:41–45 (1981) report on the in vitro metabolism of progesterone by the hypothalamus, anterior pituitary and uterus of the rat during pregnancy and observed increased metabolism of progesterone by the uterus at the end of pregnancy and decrease of 5α-reductase activity in the pituitary.

Myatt et al., in Identification and changes in concentration of prostaglandin H synthase isoforms in rat myometrium at parturition Prostaglandins 48:285–296 (1994) note that nuclear progesterone receptor concentrations were maximal on days 16–18 of pregnancy, decreased from days 18 to 22 (delivery) and fell 24 hours postpartum in the rat.

SUMMARY OF THE INVENTION

The present invention provides for a method of treating preterm labor in a subject in need of such treatment comprising administration of a therapeutically effective amount of an inhibitor of 5α-reductase type 1 to the subject. The present invention further provides for a method of preventing premature labor in a subject susceptible thereto comprising administration of a labor-preventive amount of an inhibitor of 5α-reductase type 1 to the subject. Further, the present invention also relates to a method of reducing the risk of premature labor in a subject at risk therefor. The present invention also provides for a method for stopping labor preparatory (i.e., prior) to Cesarean delivery in a subject in need of such treatment comprising administration of a therapeutically effective amount of an inhibitor of 5α-reductase type 1 to the subject.

Further, the present invention provides for compositions useful in the methods of the present invention, as well as a method of manufacture of a medicament useful for treating pre-term labor and for stopping labor preparatory to Cesarean delivery.

DETAILED DESCRIPTION OF THE INVENTION

In one embodiment, the present invention provides for a method of treating preterm labor in a subject in need of such treatment comprising administration of a therapeutically effective amount of an inhibitor of 5α-reductase type 1 to the subject.

In another embodiment of the present invention is a method of preventing premature labor in a subject susceptible thereto, comprising administration of a labor preventive amount of an inhibitor of 5α-reductase type 1 to the subject.

In yet another embodiment of the present invention is provided a method for reducing the risk of premature labor in a subject at risk therefor comprising administration of a labor preventive amount of an inhibitor of 5α-reductase type 1 to the subject.

Another embodiment of the present invention is a method for stopping labor preparatory (i.e., prior) to Cesarean delivery in a subject in need of such treatment comprising administration of a therapeutically effective amount of an inhibitor of 5α-reductase type 1 to the subject.

The present invention is also directed to a method for controlling the timing of parturition in farm animals so that delivery of the neonates occurs during the daytime. Approximately 80% of livestock are delivered at night and up to 5 to 10% of newborns die because the deliveries are not monitored properly. A 5α-reductase type 1 inhibitor is administered to the mother on the evening before the expected delivery. This delays parturition so that the delivery occurs during the daylight hours. By delaying the timing of parturition, proper monitoring of the delivery and the neonates is ensured, resulting in increased survival rates of the newborns.

The present invention is also related to the use of a 5α-reductase type 1 inhibitor for the manufacture of a medicament useful in the treatment of preterm labor in a subject in need of such treatment.

The present invention is further related to the use of a 5α-reductase type 1 inhibitor for the manufacture of a medicament useful in the prevention of premature labor in a subject susceptible thereto.

Still further, the present invention is related to the use of a 5α-reductase type 1 inhibitor for the manufacture of a medicament useful in reducing the risk of premature labor in a subject at risk therefor.

Another aspect of the present invention is the use of a 5α-reductase type 1 inhibitor for the manufacture of a medicament useful in stopping labor preparatory (i.e., prior) to Cesarean delivery in a subject in need of such treatment.

Yet a further aspect of the present invention is the use of a 5α-reductase type 1 inhibitor for the manufacture of a medicament useful in controlling the timing of parturition in farm animals so that delivery of the neonates occurs during the daytime.

Inhibitors of 5α-reductase type 1 are known in the art. For a given compound, its 5α-reductase type 1 inhibitory activity may be determined by assaying its activity as described in Example 24 in the present application. Compounds having an $IC_{50}$ under about 100 nM are 5α-reductase type 1 inhibitors useful in the present invention.

Inhibitors of 5α-reductase type 1 useful in the present invention include the 16-substituted compounds described in WO 95/11254 of structural formula I:

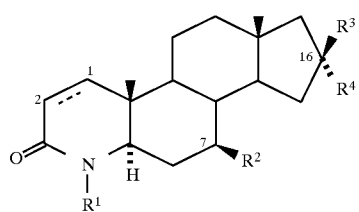

or a pharmaceutically acceptable salt or ester thereof wherein:

the C1–C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)$NR_bR_c$, where $R_b$ and $R_c$ are independently H, $C_{1-6}$ alkyl, aryl, or aryl $C_{1-6}$ alkyl; wherein the alkyl moiety can be substituted with 1–3 of: halo; $C_{1-4}$alkoxy;
or trifluoromethyl; and the aryl moiety can be substituted with 1–3 of: halo; $C_{1-4}$ alkyl; $C_{1-4}$ alkoxy; or trifluoromethyl;
(g) $C_{1-10}$ alkyl-X—;
(h) $C_{2-10}$ alkenyl-X—;
wherein the $C_{1-10}$ alkyl in (g) and $C_{2-10}$ alkenyl in (h) can be unsubstituted or substituted with one to three of:
i) halo; hydroxy; cyano; nitro; mono-, di- or trihalomethyl; oxo; hydroxysulfonyl; carboxy;
ii) hydroxy $C_{1-6}$ alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;
iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
iv) —C(O)$NR_bR_c$; —N($R_b$)—C(O)—$R_c$; —$NR_bR_c$;
where $R_b$ and $R_c$ are defined above;
(i) aryl-X—;

(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

wherein the aryl in (i) and heteroaryl in (j) can be unsubstituted or substituted with one to three of:

v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$ alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$ alkyl; $R_bR_cN$—C(O)—$C_{1-6}$ alkyl; $C_{1-6}$ alkanoylamino $C_{1-6}$ alkyl; $C_{1-6}$ aroylamino $C_{1-6}$ alkyl; wherein the $C_{1-6}$ alkyl moiety can be substituted with 1–3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$ alkyl; $C_{1-4}$alkoxy; or trifluoromethyl;

viii) —C(O)$NR_bR_c$; —O—C(O)—$NR_bR_c$; —N($R_b$)—C(O)—$R_c$; —$NR_bR_c$; $R_b$—C(O)—N($R_c$)—; where $R_b$ and $R_c$ are defined in (f) above; and —N($R_b$)—C(O)—$OR_g$, wherein $R_g$ is $C_{1-6}$ alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$ alkyl; $C_{1-4}$ alkoxy, or trifluoromethyl; —N($R_b$)—C(O) $NR_cR_d$, wherein $R_d$ is selected from H, $C_{1-6}$ alkyl, and aryl; in which said $C_{1-6}$ alkyl and aryl can be substituted as described above in (f) for $R_b$ and $R_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) $R^3$ and $R^4$ taken together can be carbonyl oxygen;

(l) $R^3$ and $R^4$ taken together can be =CH—$R_g$, wherein $R_g$ is defined in viii); and wherein:

X is selected from the group consisting of:
—O—; —S(O)$_n$—; —C(O)—; —CH(Re)—; —C(O)—O—*; —C(O)—N($R_e$)—*; —N($R_e$) —C(O)—O—*; —O—C(O)—N($R_e$)—*; —N($R_e$)C(O)—N($R_e$)—; —O—CH($R_e$)—*; —N($R_e$)—; wherein $R_e$ is H, $C_{1-3}$ alkyl, aryl, aryl- $C_{1-3}$ alkyl, or unsubstituted or substituted heteroaryl, as defined above in (j);

wherein the asterisk (*) denotes the bond which is attached to the 16-position in Structure I; and n is zero, 1 or 2.

In one embodiment of the compounds of structural Formula I are those wherein $R^1$ is hydrogen or methyl and $R^2$ is hydrogen or methyl.

A further embodiment of the compounds of Formula I are those wherein:

one of $R^3$ and $R^4$ is selected from the group consisting of hydrogen and methyl, and the other is selected from the group consisting of:

(b) cyano;
(c) fluoro;
(e) OH;
(g) $C_{1-10}$ alkyl-X—; or $C_{1-10}$ alkyl-X—, where alkyl can be substituted with aryl, and wherein aryl in turn can be substituted with 1–2 of halo or $C_{1-6}$ alkyl;
(h) $C_{2-10}$ alkenyl-X—;
(i) aryl-X—;
(j) heteroaryl-X—, wherein heteroaryl is a 5 or 6 membered heteroaromatic ring containing 1–2 ring nitrogen atoms; wherein the aryl in (i) and heteroaryl in (j) can be unsubstituted or substituted with one to two of:

x) halo; cyano; nitro; trihalomethyl; trihalomethoxy; $C_{1-6}$ alkyl; aryl; $C_{1-6}$ alkylsulfonyl; $C_{1-6}$ alkylarylsulfonamino;

xi) —$NR_bR_c$; $R_b$—C(O)—N($R_c$)—; wherein $R_b$ and $R_c$ are independently H, $C_{1-6}$ alkyl, aryl, or aryl $C_{1-6}$ alkyl; wherein the alkyl moiety can be substituted with 1–3 of: halo; $C_{14}$alkoxy; or trifluoromethyl; and the aryl moiety can be substituted with 1–3 of: halo; $C_{1-4}$ alkyl; $C_{1-4}$ alkoxy; or trifluoromethyl;

xii) a heterocyclic group, which is a 5 membered aromatic ring, containing one ring nitrogen atom, or one ring oxygen and one ring nitrogen atom; and (k) wherein $R^3$ and $R^4$ taken together can be carbonyl oxygen; and wherein:

X is selected from the group consisting of:
—O—; —S(O)$_n$—; —CH($R_e$)—; —C(O)—N ($R_e$)—*;
—O—C(O)—N($R_e$)—*;
wherein $R_e$ is H, $C_{1-3}$ alkyl, aryl, aryl $C_{1-3}$ alkyl;
wherein the asterisk (*) denotes the bond which is attached to the 16-position in Structure I; and n is zero or 2.

Compounds of Formula I which may be employed in the present invention include but are not limited to the following:

4-aza-4,7β-dimethyl-5α-androstane-3,16-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;

3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5β-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy]-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane;

pharmaceutically acceptable salts thereof, and analogs of the above-described compounds wherein the C1–C2 carbon-carbon bond is a double bond, and/or $R^1$ is —H, and/or $R^2$ is —H or methyl, where appropriate.

In another embodiment of compounds of Formula I are those further limited to those wherein the $C_1$–$C_2$ carbon-carbon bond is a single bond, $R^1$ is methyl, $R^2$ is methyl, $R^3$ is selected from unsubstituted or substituted aryloxy, and $R^4$ is hydrogen.

Some non-limiting examples of compounds of Formula I within this embodiment are:

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-trifluoromethoxyphenoxy)-5α-androstane;

3-oxo-4-aza-4,7β-dimethyl-16β-(4-methylsulfonylphenoxy)-5α-androstane;

3-oxo-4-aza-4,7β-dimethyl-16β-[4-(4-tolylsulfonylamino)phenoxy]-5α-androstane;

3-oxo-4-aza-4,7β-dimethyl-16β-[(4-phenyl)phenoxy]-5α-androstane;

3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane;

and the pharmaceutically acceptable salts thereof.

Particularly useful compounds of structural Formula I are 3-oxo-4-aza-4,7β-dimethyl-16β-(4-chlorophenoxy)-5α-androstane, 3-oxo-4-aza-4,7β-dimethyl-16β-(phenoxy)-5α-androstane, and 3-oxo-4-aza-7-methyl-16β-(4-methylphenoxy)-5α-androst-1-ene, or pharmaceutically acceptable salts thereof.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diastereomers.

The alkyl and alkenyl groups can be unsubstituted or substituted with one or more, and preferably 1–3, of:

i) halo; hydroxy; cyano; nitro; mono-, di- or trihalomethyl; oxo; hydroxysulfonyl; carboxy;

ii) hydroxy $C_{1-6}$ alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;

iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;

iv) —C(O)NR$_b$R$_c$; —N(R$_b$)—C(O)—R$_c$; —NR$_b$R$_c$; where R$_b$ and R$_c$ are defined above; and halo is F, Cl, Br or I.

As used herein the term "aryl", i.e., $C_{6-10}$ aryl, is intended to mean phenyl or naphthyl, including 1-naphthyl and 2-naphthyl, either unsubstituted or substituted as described below.

The term "heteroaryl" as used herein, is intended to include a 5, 6 or 7 membered heteroaromatic radical containing at least one member selected from the group consisting of: one ring oxygen atom, one ring sulfur atom, 1–4 ring nitrogen atoms, or combinations thereof; in which the heteroaryl ring can also be fused with one benzo or heteroaromatic ring. This category includes the following either unsubstituted or substituted heteroaromatic rings (as described below): pyridyl, furyl, pyrryl, thienyl, isothiazolyl, imidazolyl, benzimidazolyl, tetrazolyl, pyrazinyl, pyrimidyl, quinolyl, quinazolinyl, isoquinolyl, benzofuryl, isobenzofuryl, benzothienyl, pyrazolyl, indolyl, isoindolyl, purinyl, carbazolyl, isoxazolyl, thiazolyl, isothiazolyl, oxazolyl, benzthiazolyl, and benzoxazolyl. The heteroaryl ring may be attached within structural Formula I by a heteroatom, e.g., N, or carbon atom in the ring, which results in the creation of a stable structure. The heteroaryl ring can also be fused to a benzo ring.

The one to three, and more usefully one to two substituents which can be on the $C_{6-10}$ aryl and heteroaryl groups named above are independently selected from:

v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$ alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxycarbonyl; $C_{1-6}$ alkyloxycarbonyl $C_{1-6}$ alkyl; R$_b$R$_c$N—C(O)—$C_{1-6}$ alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$ alkyl; $C_{1-4}$alkoxy; or trifluoromethyl;

viii) —C(O)NR$_b$R$_c$; —O—C(O)—NR$_b$R$_c$; -N(R$_b$)—C(O)-R$_c$; —NR$_b$R$_c$; R$_b$—C(O)—N(R$_c$)—; where R$_b$ and R$_c$ are defined in (e) above; and —N(R$_b$)—C(O)—OR$_c$, wherein this instance R$_c$ is $C_{1-6}$ alkyl or aryl; —N(R$_b$)—C(O) NR$_c$R$_d$, wherein R$_d$ is selected from H, $C_{1-6}$ alkyl, and aryl; in which said $C_{1-6}$ alkyl and aryl can be substituted as described above in (e) for R$_b$ and R$_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, and wherein the heterocyclic ring can be fused with a benzo ring, and wherein said heterocyclic ring can be substituted with one to three substituents, as defined above for v), vi), vii) and viii), excluding ix) a heterocyclic group.

The fused heteroaromatic ring systems include: purine, imidazoimidazole, imidazothiazole, pyridopyrimidine, pyridopyridazine, pyrimidopyrimidine, imidazopyridazine, pyrrolopyridine, imidazo-pyridine, and the like.

The "heterocyclic" group includes the fully unsaturated heteroaryl rings described above and also their respective dihydro, tetrahydro and hexahydro derivatives resulting in partially unsaturated and fully saturated versions of the ring systems. Examples include: dihydroimidazolyl, dihydrooxazolyl, dihydropyridyl, tetrahydrofuryl, dihydropyrryl, tetrahydrothienyl, dihydroisothiazolyl, 1,2-dihydrobenzimidazolyl, 1,2-dihydrotetrazolyl, 1,2-dihydropyrazinyl, 1,2-dihydropyrimidyl, 1,2-dihydroquinolyl, 1,2,3,4-tetrahydroisoquinolyl, 1,2,3,4-tetrahydrobenzofuryl, 1,2,3,4-tetrahydroisobenzofuryl, 1,2,3,4-tetrahydrobenzothienyl, 1,2,3,4-tetrahydropyrazolyl, 1,2,3,4-tetrahydroindolyl, 1,2,3,4-tetrahydroisoindolyl, 1,2,3,4-tetrahydropurinyl, 1,2,3,4-tetrahydrocarbazolyl, 1,2,3,4-tetrahydroisoxazolyl, 1,2,3,4-tetrahydro-thiazolyl, 1,2,3,4-tetrahydrooxazolyl, 1,2,3,4-tetrahydrobenzthiazolyl, and 1,2,3,4-tetrahydrobenzoxazolyl. and the like.

The heterocyclic group can be substituted in the same fashion as described above for heteroaryl.

Whenever the terms "alkyl", "alkenyl", "alkyloxy (or alkoxy)", "aryl" or "heteroaryl", or one of their prefix roots, appear in a name of a substituent in Formula I, (e.g., aralkoxyaryloxy) they shall have the same definitions as those described above for "alkyl", "altkenyl", "alkyloxy (or alkoxy)", "aryl" and "heteroaryl", respectively. Designated numbers of carbon atoms (e.g., $C_{1-10}$) shall refer independently to the number of carbon atoms in an alkyl or alkenyl moiety or to the alkyl or alkenyl portion of a larger substituent in which alkyl or alkenyl appears as its prefix root.

Other 5α-reductase inhibitors which are useful in the method and compositions of the present invention include the compounds described in U.S. Pat. No. 5,525,608 of structural Formula II:

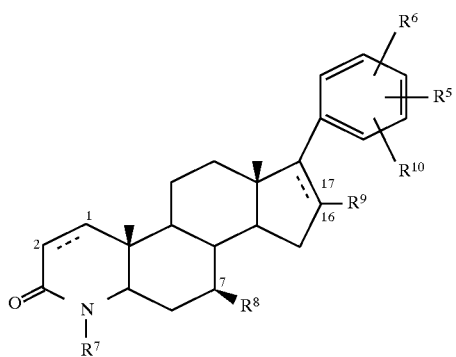

II or a pharmaceutically acceptable salt or ester thereof, wherein: the C1–C2 bond and the C16–C17 bond designated "---" each independently represent a single or double bond; $R^7$ and $R^8$ are independently selected from:
1) —H,
2) —$CH_3$ and
3) —$CH_2CH_3$;

$R^9$ is selected from:
1) —H and
2) —$CH_3$; and $R^9$ is β-oriented if C16–C17 is saturated; $R^{10}$, $R^5$ and $R^6$ are independently selected from:

1) —H,
2) —$C_{1-8}$ alkyl, unsubstituted or substituted with —OH,
3) —$C_{1-3}$ perfluoroalkyl,
4) -halo,
5) —OR $^{11}$, wherein $R^{11}$ is
   a) —H,
   b) —$C_{1-8}$ alkyl,
   c) —$C_{1-6}$ alkylcarbonyl,
   d) —$C_{1-6}$ alkylsulfonyl, or
   e) —$C_{1-6}$ alkoxycarbonyl,
6) —$NHR^{11}$,
7) —$NO_2$,
8) —$S(C_{1-6}$ alkylcarbonyl),
9) —$S(O)_n C_{1-8}$ alkyl, wherein n is 0, 1 or 2,
10) —$CO_2 R^{12}$ wherein $R^{12}$ is
    a) —H or
    b) —$C_{1-8}$ alkyl,
11) —$C(O)R^{12}$,
12) —$C(O)N(R^{12})_2$,
13) —CN,
14) —$C(R^{12})_2 OR^{11}$,
15) —$C(R^{12})_2 NR^{11}$,
16) —$C(R^{12})_2 S(C_{1-8}$ alkyl),
17) —$C(R^{12})_2 S(C_{1-6}$ alkylcarbonyl), and
18) phenyl, unsubstituted or having 1 to 3 substituents selected from:
   a) —OH,
   b) halo,
   c) $C_{1-3}$ alkyl, and
   d) $C_{1-3}$ alkoxy; or $R^{10}$ and $R^5$ or $R^5$ and $R^6$, on vicinal carbon atoms, may be joined to form with the phenyl to which they are attached a naphthyl or indanyl group; and the 17-position substituent is β-oriented if C16–C17 is saturated.

In one embodiment of the compounds are compounds of Formula I having structural Formula III:

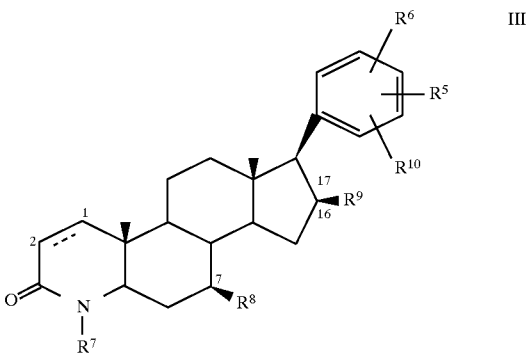

III or a pharmaceutically acceptable salt or ester thereof.

In one class of this embodiment are compounds of Formula IV

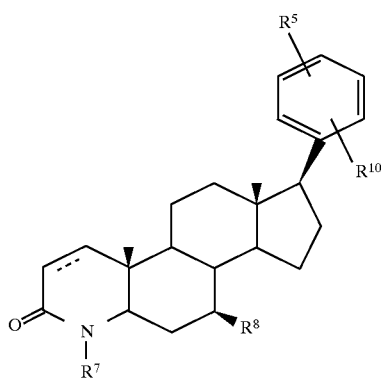

IV or a pharmaceutically acceptable salt or ester thereof, wherein:

$R^7$ is —H or —CH$_3$; and
$R^8$ is —CH$_3$ or —CH$_2$CH$_3$; and
$R^{10}$ and $R^5$ are as defined above in Formula I.

In a second embodiment of the compounds of structural Formula II are compounds of Formula I having structural Formula V:

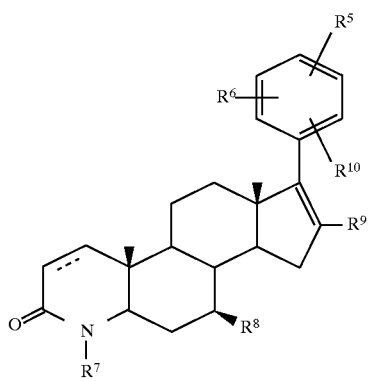

V or a pharmaceutically acceptable salt or ester thereof.

In one class of this second embodiment of compounds of Formula II of Formula VI

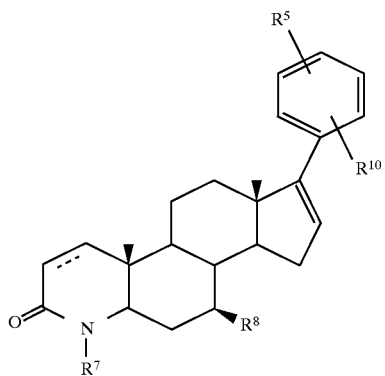

VI or a pharmaceutically acceptable salt or ester thereof, wherein:

$R^7$ is —H or —CH$_3$; and
$R^8$ is —CH$_3$ or —CH$_2$CH$_3$; and
$R^{10}$ and $R^5$ are as defined above in Formula II.

In one sub-class are compounds of either Formula IV or Formula VI further limited to those wherein:

$R^7$ is —H or —CH$_3$;
$R^8$ is —CH$_3$; and $R^{10}$ and $R^5$ are independently selected from
a) —H,
b) —OH,
c) —CH$_3$,
d) —OCH$_3$,
e) —S(O)$_n$—CH$_3$,
f) —CF$_3$,
g) halo,
h) —CHO,
i) CN,
j) —NHR$^{11}$, or $R^{10}$ and $R^5$ are on vicinal carbon atoms and are joined to form with the phenyl to which they are attached a naphthyl group.

In a second sub-class are compounds of either Formula IV or Formula VI further limited to those wherein: the C1–C2 bond is a single bond; $R^7$ is —H or —CH$_3$; and $R^8$ is —CH$_3$.

Within this second sub-class are compounds of formula either IV or Formula VI still further limited to those wherein $R^{10}$ and $R^5$ are independently selected from:

a) —H,
b) —OH,
c) —CH$_3$,
d) —OCH$_3$,
e) —S(O)$_n$—CH$_3$,
f) —CF$_3$,
g) halo,
h) —CHO,
i) CN,
j) —NH$^{11}$, or $R^{10}$ and $R^5$ are on vicinal carbon atoms and are joined to form with the phenyl to which they are attached a naphthyl group.

Examples of compounds within this second sub-class are those in the following table:

| $R^7$ | $R^8$ | |
|---|---|---|
| —CH$_3$ | —CH$_3$ | phenyl |
| —CH$_3$ | —CH$_3$ | 4-methylthiophenyl |
| —CH$_3$ | —CH$_3$ | 4-chlorophenyl |
| —CH$_3$ | —CH$_3$ | 3,5-bis(trifluoromethyl)-phenyl |
| —CH$_3$ | —CH$_3$ | 3,5-dichlorophenyl |
| —CH$_3$ | —CH$_3$ | 1-naphthyl |
| —CH$_3$ | —CH$_3$ | 2-methoxyphenyl |
| —CH$_3$ | —CH$_3$ | 3-methoxyphenyl |
| —CH$_3$ | —CH$_3$ | 4-methoxyphenyl |
| —CH$_3$ | —CH$_3$ | 4-methylsulfonylphenyl |
| —CH$_3$ | —CH$_3$ | 3-aminophenyl |
| —CH$_3$ | —CH$_3$ | 3-(carbethoxyamino)-phenyl |

Still other inhibitors of 5α-reductase type I useful in the present invention include the 6-azasteroid derivatives described in U.S. Pat. No. 5,516,799, of structural Formula VII:

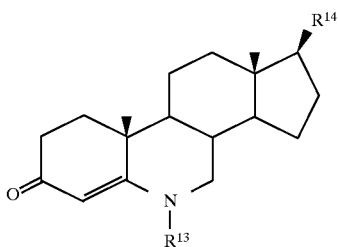

or a pharmaceutically acceptable salt or ester thereof, wherein:

$R^{13}$ is selected from —H, —CH$_3$ and —CH$_2$CH$_3$;
$R^{14}$ is selected from:
1) —H, —OH, —NH$_2$, or =O,
2) —C$_{1-12}$ alkyl,
3) —C$_{1-12}$ alkyl-phenyl,
4) —O—C$_{1-12}$ alkyl or —S(O)$_n$—C$_{1-12}$ alkyl,
5) —O-Het or —S(O)$_n$-Het,
6) —O-phenyl or —S(O)$_n$-phenyl,
7) —C$_{1-6}$ alkyl-X-C$_{1-12}$ alkyl,
8) —C$_{1-6}$ alkyl-X-Het,
9) —C(O)-phenyl,
10) —X—C(O)—C$_{1-12}$ alkyl,
11) —OC(O)—NHC$_{1-12}$ alkyl,
12) —OC(O)—NH-phenyl,
13) —CN, and
14) —NR$^{15}$R$^{16}$, wherein R$^{15}$ and R$^{16}$ are each independently selected from —H, C$_{1-12}$ alkyl, phenyl and Het;

Het is selected from piperidinyl, piperizinyl, pyrrolidinyl, pyrrolyl, furanyl and thienyl;

X is selected from the group consisting of O, NH and S(O)$_n$; and n is zero, 1 or 2.

In one embodiment of compounds of Formula VII are those
wherein X is selected from O and S.

In another embodiment of compounds of formula VII are those wherein:

$R^{13}$ is selected from —H and —CH$_3$; and
$R^{14}$ is selected from —H, —OH, =O, —C$_{1-12}$ alkyl, —C$_{1-12}$ alkyl-phenyl,
—O—C$_{1-12}$ alkyl, —O-phenyl, —OC(O)—NHC$_{1-12}$ alkyl,
—S(O)$_n$—C$_{1-12}$alkyl, and —S(O)$_n$-phenyl.

In one class of this embodiment of compounds of Formula VII further is limited to those wherein:

$R^{13}$ is selected from —H and —CH$_3$;
$R^{14}$ is selected from —H, —OH, =O, —C$_{1-12}$ alkyl, —O—C$_{1-12}$ alkyl,
—OC(O)—NHC$_{1-12}$ alkyl and —S(O)$_n$—C$_{1-12}$ alkyl.

Examples of compounds within this class include, but are not limited to, the following:

6-methyl-6-aza-androst-4-en-3,17-dione;
6-methyl-17-propyl-6-aza-androst-4-en-3-one;
6-methyl-6-aza-androst-4-en-3 -one;
6-methyl-17-hydroxy-6-aza-androst-4-en-3-one;
6-methyl-17-t-butylcarbamoyloxy-6-aza-androst-4-en-3-one;
6-aza-cholest-4-en-3-one; and
6-methyl-6-aza-cholest-4-en-3-one.

Still further examples of 5α-reductase type 1 inhibitors that may be employed in the method and compositions of the present invention include the compound of structural formula VIII:

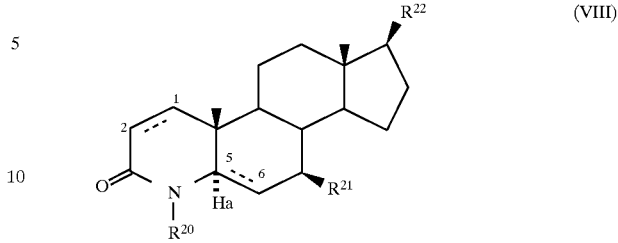

wherein:
the C1–C2 and C5–C6 bonds designated with a dotted line each independently represent a single or double bond, provided that when the C5–C6 is a double bond, H$_a$ is absent and when the C5–C6 bond is a single bond H$_a$ is present and represents hydrogen;
$R^{20}$ is selected from hydrogen and C$_{1-5}$ alkyl;
$R^{21}$ is C$_{1-5}$alkyl, either straight or branched chain; and
$R^{22}$ is C$_{3-7}$alkyl, either straight or branched chain, optionally having one degree of unsaturation;
or a pharmaceutically acceptable salt, or stereoisomer thereof.

In one class of the instant invention are compounds of formula I wherein the C5–C$_6$ bond is a single bond and H$_a$ is present.

In a sub-class of the compounds of this class are compounds wherein R$^{21}$ is methyl.

Compounds illustrating this sub-class are:
7β,20-dimethyl-4-aza-5α-pregn-17-en-3-one,
7β,20-dimethyl-4-aza-5α-pregn-1,17-dien-3-one,
20-ethyl-4,7β-dimethyl-4-aza-5α-pregn-17-en-3-one,
20-ethyl-4,7β-dimethyl-4-aza-5α-pregnan-3-one ,
7β,20-dimethyl-4-aza-5α-pregnan-3-one,
7β,20-dimethyl-4-aza-5α-pregn-1-en-3-one,
20-ethyl-4,7β-dimethyl-4-aza-5α-pregnan-3-one,
20-propyl-4,7β-dimethyl-4-aza-5α-pregnan-3-one,
20-ethyl-4,7β-dimethyl-4-aza-5α-pregn-1-en-3-one,
4,7β,20-trimethyl-4-aza-5α-pregn-1-en-3-one,
20-propyl-4,7β-dimethyl-4-aza-5α-pregn-1-en-3-one,
20-ethyl-7β-methyl-4-aza-5α-pregn-1-en-3-one,
20-propyl-7β-methyl-4-aza-5α-pregnan-3-one,
20-propyl-7β-methyl-4-aza-5α-pregn-1-en-3-one,
17β-n-propyl-7β-methyl-4-aza-5α-androst-1-en-3-one,
17β-n-propyl-4,7β-dimethyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-butyl-4,7β-dimethyl-4-aza-5α-androst-1-en-3-one,
17β-isobutyl-4,7β-dimethyl-4-aza-5α-androst-1-en-3-one,
17β-tert.-butyl-4,7β-dimethyl-4-aza-5α-androst-1-en-3-one,
17β-n-pentyl-7β-methyl-4-aza-5α-androst-1-en-3-one,
17β-isopentyl-7β-methyl-4-aza-5α-androst-1-en-3-one,
17β-(5-methylhexyl)-7β-methyl-4-aza-5α-androst-1-en-3-one,
17β-(5-methylhexyl)-4,7β-dimethyl-4-aza-5α-androst-1-en-3-one,
17β-n-propyl-7β-methyl-4-aza-5α-androstan-3-one,
17β-n-propyl-4,7β-dimethyl-4-aza-5α-androstan-3-one,
17β-n-butyl-7β-methyl-4-aza-5α-androstan-3-one,
17β-n-butyl-4,7β-dimethyl-4-aza-5α-androstan-3-one,
17β-(5-methylhexyl)-7β-methyl-4-aza-5α-androstan-3-one, and
17β-(5-methylhexyl)-4,7β-dimethyl-4-aza-5α-androstan-3-one.

Compounds further illustrating this sub-class are:
7β,20-dimethyl-4-aza-5α-pregn-17-en-3-one,
7β,20-dimethyl-4-aza-5α-pregn-1,17-dien-3-one,
20-ethyl-4,7β-dimethyl-4-aza-5α-pregn-17-en-3-one,
20-ethyl-4,7β-dimethyl-4-aza-5α-pregnan-3-one
7β,20-dimethyl-4-aza-5α-pregnan-3-one,
7β,20-dimethyl-4-aza-5α-pregn-1-en-3-one,
20-ethyl-4,7β-dimethyl-4-aza-5α-pregnan-3-one,
20-propyl-4,7β-dimethyl-4-aza-5α-pregnan-3-one,
17β-n-propyl-7β-methyl-4-aza-5α-androst-1-en-3-one,
17β-n-butyl-7β-methyl-4-aza-5α-androst-1-en-3-one,
17β-(5-methylhexyl)-7β-methyl-4-aza-5α-androst-1-en-3-one,
17β-n-propyl-7β-methyl-4-aza-5α-androstan-3-one,
17β-n-butyl-7β-methyl-4-aza-5α-androstan-3-one, and
17β-(5-methylhexyl)-7β-methyl-4-aza-5α-androstan-3-one.

In a further subclass of the present invention are compounds wherein the C1–C2 bond is a double bond and $R^{20}$ is hydrogen.

Compounds illustrating this subclass include:
7β,20-dimethyl-4-aza-5α-pregn-1,17-dien-3-one,
7β,20-dimethyl-4-aza-5α-pregn-1-en-3-one,
20-ethyl-7β-methyl-4-aza-5α-pregn-1-en-3-one,
20-propyl-7β-methyl-4-aza-5α-pregn-1-en-3-one,
17β-n-propyl-7β-methyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-pentyl-7β-methyl-4-aza-5α-androst-1-en-3-one,
17β-isopentyl-7β-methyl-4-aza-5α-androst-1-en-3-one,
17β-(5-methylhexyl)-7β-methyl-4-aza-5a-androst-1-en-3-one.

In yet another subclass of this class of the present invention are compounds wherein $R^{22}$ is $C_{3-6}$ alkyl.

Compounds illustrating this sub-class are:
7β,20-dimethyl-4-aza-5α-pregn-17-en-3-one,
7β,20-dimethyl-4-aza-5α-pregn-1,17-dien-3-one,
20-ethyl-4,7β-dimethyl-4-aza-5α-pregn-17-en-3-one,
20-ethyl-4,7β-dimethyl-4-aza-5α-pregnan-3-one
7β,20-dimethyl-4-aza-5α-pregnan-3-one,
7β,20-dimethyl-4-aza-5αpregn-1-en-3-one,
20-ethyl-4,7β-dimethyl-4-aza-5α-pregnan-3-one,
20-propyl-4,7-dimethyl-4-aza-5α-pregnan-3-one,
20-ethyl-4,7β-dimethyl-4-aza-5α-pregn-1-en-3-one,
4,7β,20-trimethyl-4-aza-5α-pregn-1-en-3-one,
20-propyl-4,7β-dimethyl-4-aza-5α-pregn-1-en-3-one,
20-ethyl-7β-methyl-4-aza-5α-pregn-1-en-3-one,
20-propyl-7β-methyl-4-aza-5α-pregnan-3-one,
20-propyl-7β-methyl-4-aza-5α-pregn-1-en-3-one,
17β-n-propyl-7β-methyl-4-aza-5α-androst-1-en-3-one,
17β-n-propyl-4,7β-dimethyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-butyl-4,7β-dimethyl-4-aza-5α-androst-1-en-3-one,
17β-isobutyl-4,7β-dimethyl-4-aza-5α-androst-1-en-3-one,
17β-tert.-butyl-4,7β-dimethyl-4-aza-5α-androst-1-en-3-one,
17β-n-pentyl-7β-methyl-4-aza-5α-androst-1-en-3-one,
17β-isopentyl-7β-methyl-4-aza-5α-androst-1-en-3-one,
17β-(5-methylhexyl)-7β-methyl-4-aza-5α-androst-1-en-3-one,
17β-(5-methylhexyl)-4,7β-dimethyl-4-aza-5α-androst-1-en-3-one,
17β-n-propyl-7β-methyl-4-aza-5α-androstan-3-one,
17β-n-propyl-4,7β-dimethyl-4-aza-5α-androstan-3-one,
17β-n-butyl-7β-methyl-4-aza-5α-androstan-3-one, and
17β-n-butyl-4,7β-dimethyl-4-aza-5α-androstan-3-one.

Further illustrating this subclass are compounds wherein $R^{21}$ is methyl.

In a further subclass of the present invention are compounds wherein the C1–C2 bond is a double bond, $R^{20}$ is hydrogen, $R^{21}$ is methyl, and $R^{22}$ is $C_{3-6}$ alkyl.

Compounds illustrating this subclass include:
7β,20-dimethyl-4-aza-5α-pregn-1,17-dien-3-one,
7β,20-dimethyl -4-aza-5α-pregn-1-en-3-one,
20-ethyl-7β-methyl-4-aza-5α-pregn-1-en-3-one,
20-propyl-7β-methyl-4-aza-5α-pregn-1-en-3-one,
17β-n-propyl-7β-methyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-pentyl-7β-methyl-4-aza-5α-androst-1-en-3-one, and
17β-isopentyl-7β-methyl-4-aza-5α-androst-1-en-3-one.

Still further illustrating this subclass are compounds wherein $R^3$ is fully saturated.

Compounds illustrating this subclass include:
7β,20-dimethyl-4-aza-5α-pregn-1-en-3-one,
20-ethyl-7β-methyl-4-aza-5α-pregn-1-en-3-one,
20-propyl-7β-methyl-4-aza-5α-pregn-1-en-3-one,
17β-n-propyl-7β-methyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-pentyl-7β-methyl-4-aza-5α-androst-1-en-3-one, and
17β-isopentyl-7β-methyl-4-aza-5α-androst-1-en-3-one.

In one embodiment of the instant invention are compounds of formula I wherein $R^{23}$ is hydrogen or methyl; $R^{24}$ is hydrogen, methyl, ethyl or propyl; Z is an alpha hydrogen and a beta substituent selected from $C_{1-4}$ alkyl, $C_{2-4}$ alkenyl, $C_{1-4}$ alkoxy, halo-$C_{1-4}$ alkyl, —$CF_3$, and $C_{3-6}$ cycloalkyl; and $R^{25}$ is $C_{1-4}$ alkyl di-substituted with phenyl, wherein each phenyl ring is independently unsubstituted or substituted.

Further compounds useful in the methods and compositions of the present invention include the compounds of structural formula XI:

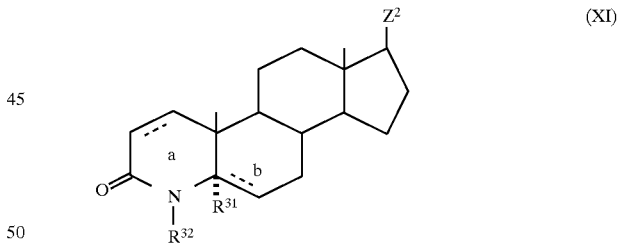

wherein "a" and "b" are both single bonds and $R^{31}$ is hydrogen, or

"a" is a double bond, "b" is a single bond and $R^{31}$ is hydrogen, or

"a" is a single bond, "b" is a double bond and $R^{31}$ is absent;

$Z^2$ is —$XR^{33}$, or —$(CHR^{30})_n$—$XR^{33}$;

n is an integer selected from 1–10;

X is —O— or —$S(O)_p$—, wherein p is zero, 1 or 2;

$R^{30}$ is —H, aryl, or —$C_{1-3}$ alkyl unsubstituted or substituted with aryl and when n is greater than 1, $R^{30}$ can be the same or different at each ocurrence;

$R^{32}$ is —H, methyl, ethyl, —OH, —$NH_2$ or —$SCH_3$;

$R^{33}$ is 1) —$C_{1-20}$ alkyl, unsubstituted or substituted with one or more of:
a) —OH,
b) halo,
c) —$C_{1-8}$ alkoxy,
d) —$C_{1-10}$ alkenyl,
e) —$CONR^{34}R^{34}$, wherein $R^{34}$ is independently
    i) —H,
    ii) —$C_{1-8}$ alkyl unsubstituted or substituted with one or more of $R^{36}$, aryl or heterocycle, the aryl being unsubstituted or substituted with one or more of $R^{36}$ or $R^{38}$,
    iii) aryl unsubstituted or substituted with one or more of $R^{36}$ or $R^{38}$, or
    iv) heterocycle, unsubstituted or substituted with one or more of $R^{36}$ or $R^{38}$,
f) —$COOR^{35}$, wherein $R^{35}$ is
    i) —H,
    ii) —$C_{1-8}$ alkyl unsubstituted or substituted with one or more of $R^{36}$ or aryl, the aryl being unsubstituted or substituted with one or more of $R^{36}$ or $R^{38}$, or
    iii) aryl, unsubstituted or substituted with one or more of $R^{36}$ or $R^{38}$,
g) —$S(O)_p$—$R^{35}$, wherein p is defined above,
h) —$N(R^{34})_2$,
i) aryl, unsubstituted or substituted with one or more of aryl, $R^{36}$ or $R^{38}$,
j) heterocycle, unsubstituted or substituted with one or more of $R^{36}$ or $R^{38}$,
k) —$C_{3-10}$ cycloalkyl, such as cyclohexyl, norbornyl, or adamantyl, unsubstituted or substituted with one or more of $R^{36}$ or $R^{38}$, or
l) —$CONR^{37}$—CO—$NHR^{37}$, wherein $R^{37}$ is —H, —$C_{1-8}$ alkyl, benzyl or cyclohexyl,
2) aryl, unsubstituted or substituted with one or more of aryl, $R^{36}$ or $R^{38}$, or
3) heterocycle or —$C_{3-10}$ cycloalkyl, either of which is unsubstituted or substituted with one or more of $R^{36}$ or $R^{38}$;

$R^{36}$ is 1) —OH,
2) —$C_{1-3}$ alkoxy,
3) —CN,
4) —$COOR^{35}$
5) —$C_{1-8}$alkyl-$COOR^{35}$,
6) —$NO_2$, or
7) —halo; and
8) amino, mono-$C_1$-$C_4$ alkylamino, di-$C_1$-$C_4$alkylamino;

$R^{38}$ is 1) —$C_{1-8}$ alkyl, unsubstituted or substituted with one or more of aryl or $R^{36}$,
2) —CO—A, —$C_{1-8}$ alkyl-CO—A, —NHCO—A, or —$S(O)_p$—A, wherein p is defined above and A is
    a) —H,
    b) —$C_{1-8}$ alkyl, unsubstituted or substituted with one or more of
        i) —$R^{36}$, or
        ii) aryl, unsubstituted or substituted with one or more of $R^{36}$, or
    c) aryl, unsubstituted or substituted with one or more of $R^{36}$,
3) —NHCO-heterocycle,
4) —$N(R^{39})_2$ or —$CON(R^{39})_2$ wherein $R^{39}$ is independently heterocycle, or —A,
5) —NHCO—$(CH_2)_q$—CO—$Q^1$, wherein q is 1–4, and $Q^1$ is —$N(R^{39})_2$ or —$OR^{39}$;

with the proviso that when Z is —$OR^{33}$, $R^{32}$ is —H, a is a single bond and b is a single or double bond, $R^4$ is not isopentyl; or a pharmaceutically acceptable salt or ester thereof.

In one embodiment, this invention is represented by compounds of formula XII:

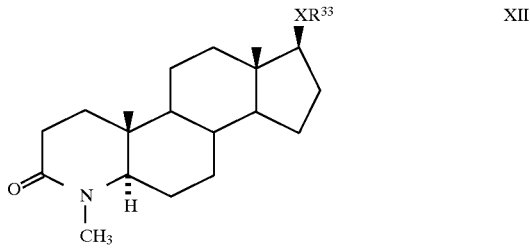

XII wherein $R^{33}$ is —$C_{1-20}$ alkyl, unsubstituted or substituted with one or more of
—OH, halo, —$C_{1-8}$alkoxy, —$C_{1-6}$alkenyl, —$S(O)_p$—$R^{34}$, —$N(R^{34})_2$, aryl unsubstituted or substituted with one or more of aryl, $R^{36}$ or $R^{38}$, heterocycle unsubstituted or substituted with one or more of $R^{36}$ or $R^{38}$, or —$C_{3-10}$ cycloalkyl unsubstituted or substituted with one or more of $R^{36}$ or $R^{38}$
and X, p, $R^{34}$, $R^{36}$ and $R^{38}$ are all defined as in formula XI.

A preferred embodiment of this invention is represented by compounds of formula XII wherein $R^{33}$ is —$C_{1-20}$ alkyl substituted with —$CONR^{34}R^{34}$, —$COOR^{35}$ or —$CONR^{37}CONHR^{37}$, and X, $R^{34}$, $R^{35}$ and $R^{37}$ are defined as in formula I.

A preferred embodiment of this invention is represented by compounds of formula XII wherein $R^{33}$ is
aryl unsubstituted or substituted with one or more of aryl, $R^{36}$ or $R^{38}$;
heterocycle unsubstituted or substituted with one or more of $R^{36}$ or $R^{38}$; or
—$C_{3-10}$ cycloalkyl unsubstituted or substituted with one or more of $R^{36}$ or $R^{38}$; and X, $R^{36}$ and $R^{38}$ are defined as in formula I.

A preferred embodiment of this invention is represented by compounds of formula XIII

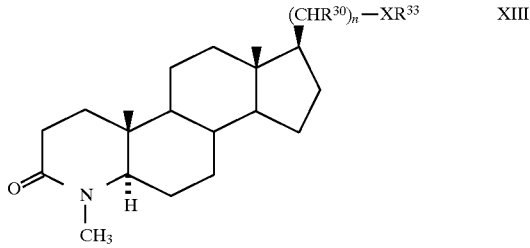

XIII wherein $R^{33}$ is —$C_{1-20}$ alkyl, unsubstituted or substituted with one or more of
—OH, halo, —$C_{1-8}$alkoxy, —$C_{1-6}$alkenyl, —$S(O)_p$—$R^{34}$, —$N(R^{34})_2$, aryl unsubstituted or substituted with one or more of aryl, $R^{36}$ or $R^{38}$, heterocycle unsubstituted or substituted with one or more of $R^{36}$ or $R^{38}$, or —$C_{3-10}$ cycloalkyl unsubstituted or substituted with one or more of $R^{36}$ or $R^{38}$,
and X, $R^{30}$, n, p, $R^{34}$, $R^{36}$ and $R^{38}$ are defined as in formula XI.

Another preferred embodiment of this invention is represented by compounds of formula XIII wherein $R^{33}$ is —$C_{1-20}$ alkyl substituted with —$CONR^{34}R^{34}$, —$COOR^{35}$ or —$CONR^{37}CONHR^{37}$, and X, $R^{30}$, n, $R^{34}$, $R^{35}$ and $R^{37}$ are defined as in formula I.

A further preferred embodiment of this invention is represented by compounds of formula XIII wherein $R^{33}$ is
aryl unsubstituted or substituted with one or more of aryl, $R^{36}$ or $R^{38}$;

heterocycle unsubstituted or substituted with one or more of $R^{36}$ or $R^{38}$; or —$C_{3-10}$ cycloalkyl unsubstituted or substituted with one or more of $R^{36}$ or $R^{38}$; and X, $R^{30}$, n, $R^{36}$ and $R^{38}$ are defined as in formula XI.

Unless stated otherwise, the 17-position substituent is assumed to be in the beta configuration.

Novel compounds of the present invention include but are not limited to the following compounds:

20-(methoxymethyl)-4-methyl-5α-4-azapregnan-3-one,
17-(carbobenzyloxymethoxymethyl)-4-methyl-5α-4-azaandrostan-3-one,
5α-4-azaandrostan-3-on-17β-yloxy-N-(4-acetylphenyl)acetamide,
17α-thiophenoxy-4-methyl-5α-4-azaandrostan-3-one,
17-(methoxymethyl)-4-methyl-5α-4-azaandrostan-3-one,
17-(ethylthiomethyl)-4-methyl-5α-4-azaandrostan-3-one,
17-(carboxymethoxymethyl)-4-methyl-5α-4-azaandrostan-3-one,
17-(carboethoxymethoxymethyl)-4-methyl-5α-4-azaandrostan-3-one,
17-(carbobenzyloxymethoxymethyl)-4-methyl-5α-4-azaandrostan-3-one,
17-(diphenylmethoxymethyl)-4-methyl-5α-4-azaandrostan-3-one,
20-(diphenylmethoxy)-4-methyl-5α-4-azapregnan-3-one,
20-methoxy-4-methyl-5α-4-azapregnan-3-one,
20-(methoxymethyl)-4-methyl-5α-4-azapregnan-3-one,
20-(diphenylmethoxymethyl)-4-methyl-5α-4-azapregnan-3-one,
20-(ethylthiomethyl)-4-methyl-5α-4-azapregnan-3-one,
20-(isopropylthiomethyl)-4-methyl-5α-4-azapregnan-3-one, ethyl 4-methyl-5α-4-azaandrostan-3-on-17β-yloxyacetate, diphenylmethyl 4-methyl-5α-4-azaandrostan-3-on-17β-yloxyacetate,
4-methyl-5α-4-azaandrostan-3-on-17β-yloxy-N-(3,4-dichlorobenzyl)acetamide,
4-methyl-5α-4-azaandrostan-3-on-17β-yloxy-N-phenylacetamide,
4-methyl-5α-4-azaandrostan-3-on-17β-yloxyacetic acid,
4-methyl-5α-4-azaandrostan-3-on-17β-yloxy-N-(4-acetylphenyl)acetamide,
4-methyl-5α-4-azaandrostan-3-on-17β-yloxyacetamide,
7β-(4-biphenyloxy)-4-methyl-5α-4-azaandrostan-3-one,
7β-(2,4-dinitrophenoxy)-4-methyl-5α-4-azaandrostan-3-one,
4-methyl-17α-phenoxy-5α-4-azaandrostan-3-one,
17α-(4-biphenyloxy)-4-methyl-5α-4-azaandrostan-3-one,
17β-diphenylmethoxy-4-methyl-5α-4-azaandrostan-3-one,
4-methyl-17α-thiophenoxy-5α-4-azaandrostan-3-one,
4-methyl-17α-phenylsulfonyl-5α-4-azaandrostan-3-one,
4-methyl-17α-phenylsulfinyl-5α-4-azaandrostan-3-one (isomer a),
4-methyl-17α-phenylsulfinyl-5α-4-azaandrostan-3-one (isomer b),
4-methyl-17β-(4-nitrophenoxy)-5α-4-azaandrostan-3-one,
17β-(4-aminophenoxy)-4-methyl-5α-4-azaandrostan-3-one hydrochloride,
17β-(4-acetamidophenoxy)-4-methyl-5α-4-azaandrostan-3-one,
17β-(4-cyanophenoxy)-4-methyl-5α-4-azaandrostan-3-one,
17β-(4-carboxamidophenoxy)-4-methyl-5α-4-azaandrostan-3-one,
17β-methyleneoxy-[N-cyclohexyl-N-(N-cyclohexylcarbamoyl)-carbamoyl]-4-methyl-5α-4-azaandrostan-3-one,
4-methyl-17β-(3-pyridyl)oxy-5α-4-azaandrostan-3-one,
4-methyl-17β-(2-pyridyl)methoxy-5α-4-azaandrostan-3-one,
17β-benzyloxy-4-methyl-5α-4-azaandrostan-3-one, ethyl 5α-4-azaandrostan-3-on-17β-yloxyacetate,
5α-4-azaandrostan-3-on-17β-yloxyacetic acid,
5α-4-azaandrostan-3-on-17β-yloxy-N-phenylacetamide,
5α-4-azaandrostan-3-on-17β-yloxy-N-(4-acetylphenyl)acetamide, diphenylmethyl 5α-4-azaandrostan-3-on-17β-yloxyacetate,
17β-methyleneoxy-[N-cyclohexyl-N-(N-cyclohexylcarbamoyl)-carbamoyl]-5α-4-azaandrostan-3-one,
5α-4-azaandrostan-3-on-17β-yloxy-N-[4-(1(RS)-hydroxyethyl)-phenyl]acetamide,
5α-4-azaandrostan-3-on-17β-yloxy-N-(4-t-butylphenyl)acetamide,
17β-methyleneoxy-[N-isopropyl-N-(N-isopropylcarbamoyl)-carbamoyl]- 5α-4-azaandrostan-3-one,
17-(4-methylpentyloxy)-4-methyl-5α-4-azaandrostan-3-one,
17-hexyloxy-4-methyl-5α-4-azaandrostan-3-one,
4-methyl-17-propyloxy-5α-4-azaandrostan-3-one,
4-methyl-17-undecyloxy-5α-4-azaandrostan-3-one,
17-allyloxy-4-methyl-5α-4-azaandrostan-3-one,
17-allyloxy-4-methyl-4-azaandrost-5-en-3-one, and
17-hexyloxy-4-methyl-4-azaandrost-5-en-3-one.

Novel compounds of this invention further include, but are not limited to:

17-(4-(isobutyl)benzyloxy)methyl-4-methyl-5α-4-azaandrostan-3-one,
17-(4-acetamidobenzyloxy)methyl-4-methyl-5α-4-azaandrostan-3-one,
4-methyl-17-(3-nitrobenzyloxy)methyl-5α-4-azaandrostan-3-one,
4-methyl-17-(phenoxyethoxymethyl)-5α-4-azaandrostan-3-one,
17-(3-(isopropylthio)propyloxy)methyl-4-methyl-5α-4-azaandrostan-3-one,
17-(2-fluorobenzyloxy)methyl-4-methyl-5α-4-azaandrostan-3-one,
4-methyl-17-(3-(trifluoromethyl)benzyloxy)methyl-5α-4-azaandrostan-3-one,
17-(4-dimethylaminobenzyloxy)methyl-4-methyl-5α-4-azaandrostan-3-one,
17-((N-t-butyl-carboxamido)methoxymethyl)-4-methyl-5α-4-azaandrostan-3-one,
20-(3-(ethylthio)propyl)-4-methyl-5α-4-azapregnan-3-one,
20-(2-(benzyloxy)ethyl)-4-methyl-5α-4-azapregnan-3-one,
20-(3-methoxybenzyloxy)methyl-4-methyl-5α-4-azapregnan-3-one,
17α-(carboethoxymethoxy)benzyl-4-methyl-5α-4-azaandrostan-3-one,
20-(4-(methylthio)benzyloxy)methyl-4-methyl-5α-4-azapregnan-3-one,
4-methyl-17-n-octylthiomethyl-5α-4-azaandrostan-3-one,
20-(t-butylthiomethyl)-4-methyl-5α-4-azapregnan-3-one,
17-(2-furfuryl)thiomethyl-4-methyl-5α-4-azaandrostan-3-one,
17-(geranyloxymethyl)-4-methyl-5α-4-azaandrostan-3-one,
4-methyl-20-(2-(n-nonylthio)ethyl)-5α-4-azapregnan-3-one,
20-(methylthiomethyl)-4-methyl-5α-4-azapregnan-3-one,
17-(4-(benzyloxy)benzyloxy)methyl-4-methyl-5α-4-azaandrostan-3-one,
20-(diphenylnethylthio)methyl-4-methyl-5α-4-azapregnan-3-one,
17-(3-(ethylthio)propyl)-4-methyl-5α-4-azaandrostan-3-one, 4-methyl-20-(phenylthiomethyl)-5α-4-azapregnan-3-one,
17-(ethylsulfonylmethyl)-4-methyl-5α-4-azaandrostan-3-one, or
17-(4-ethoxybenzyloxy)methyl-4-methyl-5α-4-azaandrostan-3-one.

A further compound useful in the methods of the present invention is 4,7β-dimethyl-4-aza-5α-cholestan-3-one.

Also useful in the present invention are compounds which are inhibitors of 5α-reductase type 1 and 5α-reductase type 2. These compounds are also called "dual inhibitors" herein. Suitable dual inhibitors include those compounds wherein the type 1 $IC_{50}$ is under about 100 nM as determined in the assay described in Example 24, and the $IC_{50}$ for the type 2 activity as determined in the assay described in Example 24 is under about 200 nM.

Among the dual inhibitors useful in the methods of the present invention are those of structural formula IX:

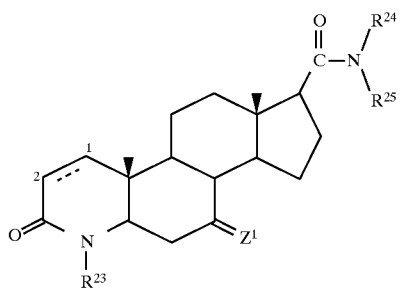

or a pharmaceutically acceptable salt or ester thereof, wherein:
  the $C_1$–$C_2$ bond designated "---" represents a single or double bond;
  $R^{23}$ is selected from:
   1) —H,
   2) —CH$_3$ and
   3) —CH$_2$CH$_3$;
  $Z^1$ is selected from:
   1) oxo,
   2) α-H and a β-substituent selected from:
    a) $C_{1-4}$ alkyl,
    b) $C_{2-4}$ alkenyl,
    c) —CH$_2$ COOH,
    d) —OH,
    e) —COOH,
    f) —COO ($C_{1-4}$ alkyl),
    g) —OCONR$^{26}$R$^{27}$ wherein
     R$^{26}$ and R$^{27}$ are independently selected from
      i) —H,
      ii) —C$_{1-4}$ alkyl,
      iii) phenyl and
      iv) benzyl;
     or R$^{26}$ and R$^{27}$ taken together with the nitrogen to which they are attached represent a 5–6 membered saturated heterocycle optionally containing one other heteroatom selected from —O—, —NH— and —S—;
    h) $C_{1-4}$ alkoxy,
    i) $C_{3-6}$ cycloalkoxy,
    j) —OC(O)R$^{28}$, wherein R$^{28}$ is $C_{1-6}$ alkyl or phenyl,
    k) halo,
    l) halo-$C_{1-2}$ alkyl,
    m) —CF$_3$, and
    n) $C_{3-6}$ cycloalkyl;
   3) =CHR$^{29}$;
   4) spirocyclopropane either unsubstituted or substituted with R$^{29}$;

$R^{24}$ is selected from —H and $C_{1-6}$ alkyl, either unsubstituted or substituted with one or more of aryl, heteroaryl, —COOH or —OH;
$R^{25}$ is —$C_{1-6}$ alkyl substituted with one or more of aryl, heteroaryl,
  —COOH, —OH or di-aryl amino; and
$R^{29}$ is selected from —H and $C_{1-4}$ alkyl.

In one class of this embodiment are compounds of formula I that have structural formula X

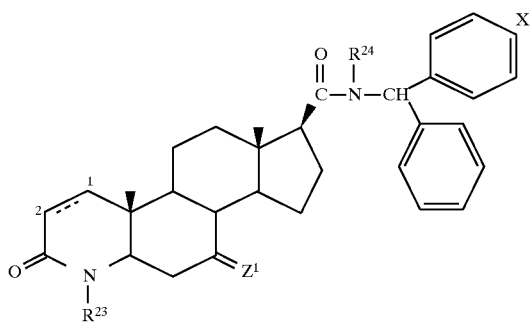

or a pharmaceutically acceptable salt thereof wherein $R^{23}$ is hydrogen or methyl; $R^{24}$ is hydrogen or methyl, and $Z^1$ is alpha hydrogen and beta methyl.

Some examples of compounds within this class are:
N-(diphenylmethyl)-3-oxo-4-aza-7β-methyl-5α-androstane-17β-carboxamide;
N-(diphenylmethyl)-3-oxo-4-aza-7β-methyl-5α-androst-1-ene-17β-carboxamide;
N-(diphenylmethyl)-3-oxo-4-aza-4,7β-dirnethyl-5α-androstane-17β-carboxamide; and
N-(methyl),N-(diphenylmethyl)-3-oxo-4-aza-4,7β-dimethyl-5α-androstane-17β-carboxamide.

Other suitable dual inhibitors include:
17β-N-(2,5-bis(trifluoromethyl))phenyl carbamoyl-4-aza-5α-androst-1-en-3-one.

The term halo or halogen is meant to include fluoro, chloro, bromo and iodo.

Also useful in the present invention are pharmaceutically acceptable salts of the 5α-reductase compounds, where a basic or acidic group is present on the structure. When an acidic substituent is present, i.e. —COOH, there can be formed the ammonium, sodium, potassium, calcium salt, and the like, for use as the dosage form. Where a basic group is present, such as amino, an acidic salt, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, and valerate.

The subject treated in the methods above is a pregnant female mammal, particularly a female human. The method may be employed in a pregnant female mammal who has begun to experience labor prematurely. Alternatively, the method may be employed in a pregnant female mammal with a history of premature labor, or a pregnant female whose pregnancy puts her at risk for premature labor by, for example, involving conditions that make premature labor more likely, including carrying multiple developing embryos, medical disorders such as serious cardiovascular or renal disease, severe anemia, cholestasis of pregnancy, marked hyperthyroidism and poorly controlled diabetes mellitus. Other factors known to correlate with the incidence of preterm labor include maternal age (the very young—under 20 years of age—and older women—over forty years of age—are predisposed); social class (the incidence is higher among the socioeconomically deprived); weight (the malnourished are more often affected); height (women of short stature are prone); prior preterm labors; prior induced abortions; work habits (hard physical work increases the incidence); smoking; and certain pregnancy complications (such as hypertension, bacteriuria, and antepartum hemorrhage). Alternatively, the subject may be a pregnant female farm animal.

A subject in need of the present invention may also be identified as possessing high hormone levels of 3α-diol glucuronide or dihydrotestosterone throughout pregnancy. Alternatively, the subject in need of the present invention may be identified as possessing inadequate hormone levels of progesterone throughout pregnancy.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "Cesarean delivery" shall mean incision through the abdominal and uterine walls for delivery of a fetus.

The term "therapeutically effective amount" means the amount of 5α-reductase inhibitor that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

The 5α-reductase type 1 inhibitors employed in the present invention are useful as pharmacologic agents for mammals, especially for humans, for the treatment and prevention of disorders wherein preterm may be involved. Examples of such disorders include preterm labor. These compounds may also find usefulness for stoppage of labor preparatory to Cesarean delivery.

Generally, the daily dosage of the 5α-reductase inhibitor may be varied over a wide range from 0.01 to 500 mg per adult human per day. In a preferred embodiment, the 5α-reductase inhibitor is administered at a dose of 1.0 to 100 mg per day. For oral administration, the compositions are preferably provided in the form of tablets containing 0.01, 0.05, 0.1, 0.5, 1.0,. 2.5, 5.0, 10.0, 15.0, 25.0, 50.0 and 100 milligrams of active ingredient for the symptomatic adjustment of the dosage to the subject to be treated. An effective amount of the drug is ordinarily supplied at a dosage level of from about 0.0002 mg/kg to about 50 mg/kg of body weight per day. The range is more particularly from about 0.001 to 7 mg/kg of body weight per day.

The dose may be administered in a single daily dose or the total daily dosage may be administered in divided doses of two, three or four times daily. Furthermore, when administered via intranasal routes, transdermal routes, by rectal suppositories, or through a continual intravenous solution, the dosage administration will, of course, be continuous rather than intermittent throughout the dosage regimen.

In the method of treating premature labor and the method of stopping labor preparatory to Cesarean delivery, the 5α-reductase type 1 inhibitor may preferably be administered for a short treatment period. In the methods of preventing premature labor and reducing the risk of premature labor, the treatment is preferably ongoing throughout the pregnancy. Most preferably the compound is administered throughout the last trimester in a subject having a history of premature labor. Alternatively, the treatment may be intermittent.

Formulations of the 5α-reductase inhibitors employed in the present method for medical use comprise the 5α-reductase type 1 inhibitor together with an acceptable carrier thereof and optionally other therapeutically active ingredients. The carrier must be pharmaceutically acceptable in the sense of being compatible with the other ingredients of the formulation and not deleterious to the recipient subject of the formulation.

The present invention, therefor further provides a pharmaceutical formulation comprising a 5α-reductase type 1 inhibitor together with a pharmaceutically acceptable carrier thereof.

The formulations include those suitable for oral, rectal, intravaginal, topical or parenteral (including subcutaneous, intramuscular and intravenous administration). Preferred are those suitable for oral and intravenous administration.

The formulations may be presented in a unit dosage form and may be prepared by any of the methods known in the art of pharmacy. All methods include the step of bringing the active compound in association with a carrier which constitutes one or more ingredients. In general, the formulations are prepared by uniformly and intimately bringing the active compound in association with a liquid carrier, a waxy solid carrier or a finely divided solid carrier, and then, if needed, shaping the product into desired dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet may be made by compression or molding, optionally with one or more accessory ingredients. Compressed tablets may be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like may be made by adding the active compound to the solution or suspension. Additional dispersing agents which may be employed include glycerin and the like.

Formulations for rectal administration may be presented as a suppository with a conventional carrier, i.e., a base that is nontoxic and nonirritating to mucous membranes, compatible with the 5α-reductase type 1 inhibitors, and is stable in storage and does not bind or interfere with the release of the 5α-reductase type 1 inhibitor. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Formulations for vaginal administration may be presented as a vaginal suppository with a conventional carrier, i.e., a base that is nontoxic and nonirritating to the vaginal membranes, compatible with the 5α-reductase type 1 inhibitors, and is stable in storage and does not bind or interfere with the release of the 5α-reductase type 1 inhibitor. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed. For vaginal administration, glycerinated gelatin is the preferred base. Other formulations appropriate for vaginal administration include creams, jellies and aerosol foams.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamide-phenol, polyhydroxyethylaspartamidephenol, or polyethylene-oxide polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations which comprise a sterile aqueous preparation of the active compound which is preferably isotonic with the blood of the recipient. Such formulations suitably comprise a solution or suspension of a compound that is isotonic with the blood of the recipient subject. Such formulations may contain distilled water, 5% dextrose in distilled water or saline and the active compound. Often it is useful to employ a pharmaceutically and pharmacologically acceptable acid addition salt of the active compound that has appropriate solubility for the solvents employed. Useful salts include the hydrochloride isothionate and methanesulfonate salts. Useful formulations also comprise concentrated solutions or solids comprising the active compound which on dilution with an appropriate solvent give a solution suitable for parenteral administration.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention has the objective of treating, preventing, and reducing the risk of premature labor and stopping labor preparatory to Cesarean delivery by oral, rectal, intravaginal, topical or parenteral (including subcutaneous, intramuscular and intravenous administration) administration of a 5α-reductase type 1 inhibitor either alone or in combination with another 5α-reductase inhibitor, either a type 1 inhibitor, a type 2 inhibitor, or a dual inhibitor, other tocolytic agents used in the treatment of preterm labor such as β-adrenergic agonists (e.g., ritodrine, isoproterenol, terbutaline, albuterol), magnesium sulfate, ethanol, other oxytocin antagonists (e.g., atosiban), calcium transport blockers (e.g., nicardipine, nifedipine), prostaglandin synthesis inhibitors (e.g., indomethacin), nitric oxide donors (e.g., nitroglycerine, S-nitroso-N-acetylpenicillamine), phosphodiesterase inhibitors, and progestins (e.g., progesterone). Preferred combinations are simultaneous or alternating treatments of a 5α-reductase type 1 inhibitor and a second tocolytic agent. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. The compounds of the instant invention may also be used in combination with antenatal steroids (e.g., dexamethasone). This particular combination has beneficial effects on the neonate by both decreasing uterine activity to prolong gestation and increasing fetal maturation. It will be understood that the scope of combinations of the compounds of this invention with other agents useful for treating preterm labor related conditions includes in principle any combination with any pharmaceutical composition useful for treating preterm labor, or stopping labor prior to Cesarean delivery.

The 5α-reductase type 1 inhibitors of structural formula VIII that may be employed this invention can be prepared as shown in Scheme 1.

SCHEME 1:

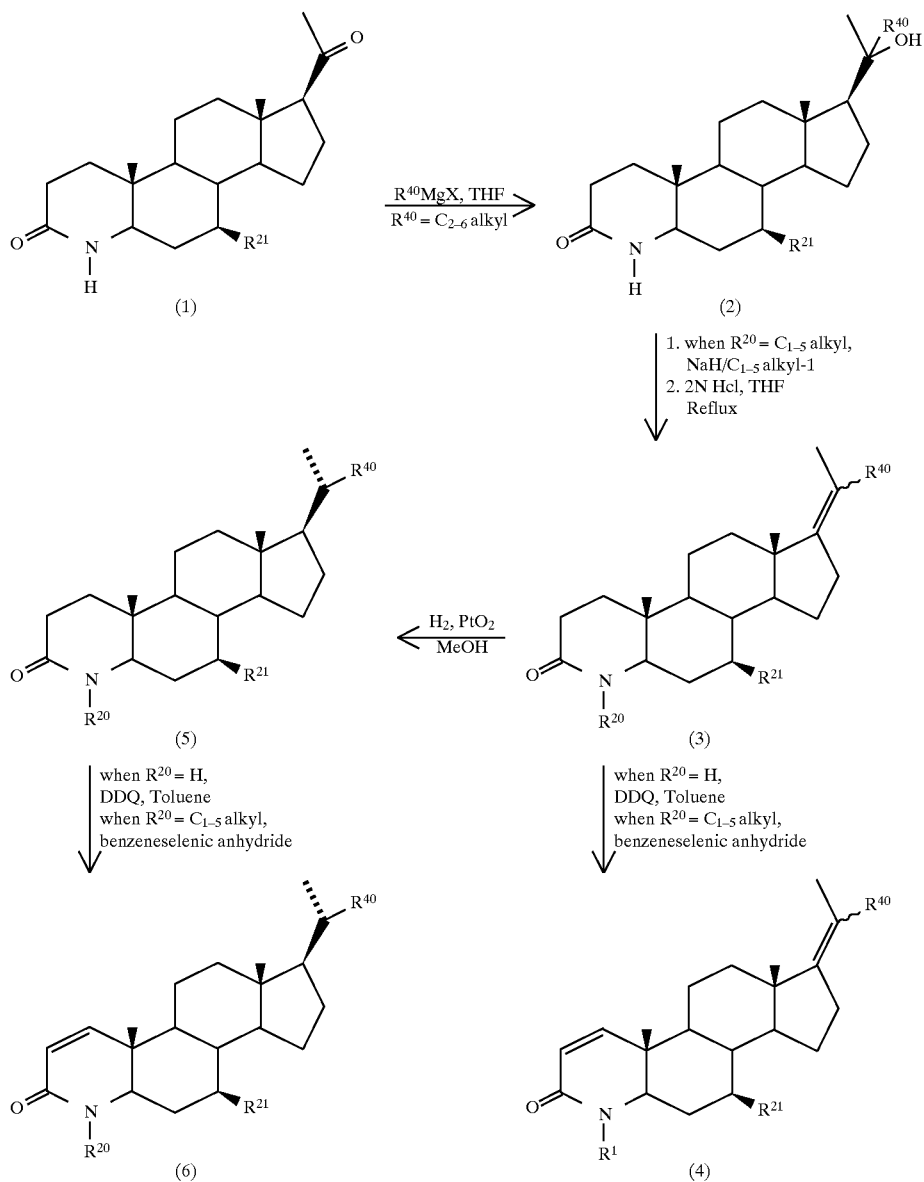

Starting with commercially available pregnenolone acetate, the appropriately 7-substituted derivative is prepared according to the procedures of PCT publication WO 93/23420 and to produce (1), the 7β-alkyl-substituted pregnenolone acetate. Treating (1) with the appropriate $C_{2-6}$ alkyl Grignard in tetrahydrofuran (THF), produces the tertiary carbinol (2). The tertiary carbinol (2) may be alkylated at the 4-position by treatment with sodium hydride and the appropriate $C_{1-5}$ alkyl iodide in a polar aprotic solvent such as THF or dimethylformamide (DMF). The 4-NH or 4-N-alkyl compound is then dehydrated in the presence of acid, for example, HCl or acetic acid, in a solvent such as THF or alcohol to produce the 17-ene (3). The 17-ene (3), in turn, may be dehydrogenated to form the 1,17-diene (4) by treatment with DDQ in toluene or benzeneselenic anhydride in chlorobenzene, or other known methods, for example as described in U.S. Pat. Nos. 5,084,574 and 5,021,571. DDQ is preferred for 4-NH compounds and benzeneselenic anhydride is preferred for 4-N-alkyl compounds.

Alternatively, the 17-ene (3) may be hydrogenated in the presence of a hydrogenation catalyst, for example $PtO_2$, Pd/C, rhodium on alumina, preferably $PtO_2$, in an appropriate solvent such as an alcohol or acetic acid, preferably methanol, to form the 17-alkyl derivative (5). The 17-alkyl derivative (5), in turn, may be dehydrogenated to form the 1-ene (6) by treatment with DDQ in toluene or benzeneselenic anhydride in chlorobenzene, as described above.

The desired 4-N-alkyl substitution may be effected as described previously by treating (2) with the appropriate alkyl iodide, or alternative, the procedure may be carried through with the 4-NH compound, and following after the desired 17-substitution and optional insertion of the 1,2-double bond, the 4-NH compound may be alkylated to the desired 4-N-alkyl compound.

Processes for inserting the 1,2-double bond in a 3-oxo-4-azasteroid are described in U.S. Pat. Nos. 5,084,574 and 5,021,571. The formation of a 7-β bond is described in U.S. Pat. Nos. 4,220,775 5,237,064.

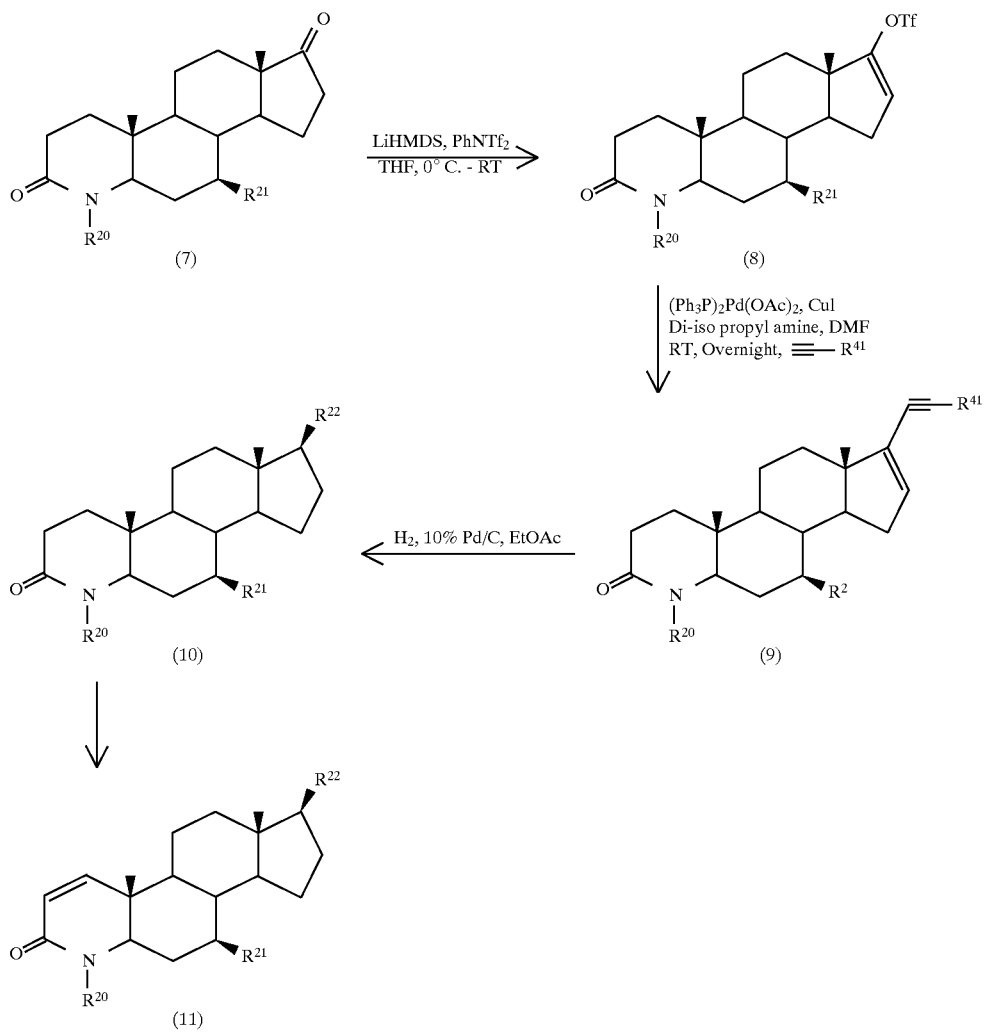

Alternatively, the compounds of the present invention may be prepared according to the procedures of Scheme 2. Compound (7), obtained according to procedures in WO 93/23420, is treated with N-phenyl trifluoro methane sulfonamide in a base such as lithium hexamethyldisilazide in THF to form the enol triflate (8). The enol triflate (8) is converted to the desired enyne (9) by treatment with di(triphenylphosphine)palladium diacetate or other appropriate $Pd_0$ catalyst with a catalytic amount of cuprous iodide and a mild base such as diisopropylamine or triethylamine in DMF with the appropriate alkyne. The enyne (9) is hydrogenated to produce the 17-alkyl derivative (10) by treating with $H_2$ in the presence of 10% Pd/C in an alcoholic or ethyl acetate solvent, preferably ethyl acetate. Insertion of the 1,2-double bond, if desired is accomplished as described in Scheme 1 to produce the 17-alkyl-1-ene (11).

The following examples are not intended to be limitations on the scope of the instant invention in any way, and they should not be so construed. Furthermore, examples are not to be construed as forming the only methods and compositions that are considered as the invention. Those skilled in the art will readily understand that known variations of the conditions, processes, methods and compositions of the following preparative procedures can be used.

EXAMPLE 1

Effect of the 5α-reductase type 1 inhibitor 3-oxo-4-aza-4,7β-dimethyl-16β-(4-chlorophenoxy)-5α-androstane on parturition in the rat Fifty female Sprague-Dawley rats (Charles River Laboratories, Raleigh, N.C.) approximately 11 weeks old, weighing from 211 to 297 grams were assigned to the present study. The female rats were housed singly in stainless steel hanging cages prior to and after cohabitation with a male of the same strain. During cohabitation, females were caged with untreated males of the same strain in a ratio of 1 female: 1 male. On Gestational Day (GD) 15 to 17, females were transferred to individual clear polycarbonate boxes containing Beta-Chip bedding in preparation for delivery and in which they remained with their litters throughout the lactation period. Room temperature was maintained between 19.4° and 25.0° C.; room humidity was maintained between 40 and 60% relative humidity, and room lights were set for alternating 12-hour periods of light and dark throughout the study. All rats had free access to PMI Certified Rodent Diet #5002 and tap water throughout the study.

Vehicle consisted of 0.5% methylcellulose in deionized water with 0.2% sodium laurel sulfate (SLS) and was prepared on a weekly basis and refrigerated when not in use.

The high dose formulation of 3-oxo-4-aza-4,7β-dimethyl-16β-(4-chlorophenoxy)-5α-androstane ("test compound") (4 mg/mL, in vehicle) was prepared on a weekly basis and was refrigerated when not in use. All lower does formulations (0.5, 1.0 and 2.0 mg/mL) were prepared on a daily basis by diluting the high dose preparation with the vehicle. Ten females were randomly allocated to each of the following treatment groups: Control, 2.5 mg test compound/kg/day, 5.0 mg test compound/kg/day, 10 mg test compound/kg/day, 20 mg test compound/kg/day. The formulation was administered by oral gavage in a dosage volume of 5 ml/kg based on the most recent body weight. Females were treated once daily with the dose above from GD 6 through LD (lactation day) 20.

Each female was housed with one untreated male of the same strain. Females were selected for the study when daily examination revealed the presence of copulatory plugs in the cage pan or in the vagina, or the presence of sperm in a vaginal lavage. The day of finding the plugs and/or sperm was considered GD 0.

From GD21 until the completion of delivery (LD 0), each pregnant female was observed on four occasions throughout the day. On GD 24, females were observed twice at 7:30 am and 10:00 am. The onset and completion of delivery and any signs of difficulty in parturition were noted. Those females that had completed delivery at the first observation of the day were assigned a whole day value for the length of gestation (e.g. 21.0 or 22.0 days). Those females that completed delivery during the workday were assigned a half day value (e.g. 21.5 or 22.5 days).

In all drug-treated groups, there were treatment-related increases in the length of gestation. In the 5, 10 and 20 mg/kg/day groups, there were treatment related increases in the failure to initiate or complete parturition. These findings are considered to be treatment-related due to the high incidence of occurrence. The length of gestation data are summarized below as the number of females completing parturition on various days of gestation:

| Delivery Day | Control | mg/kg/day 2.5 | 5.0 | 10.0 | 20 |
|---|---|---|---|---|---|
| GD 22.0 | 6 | 2 | 2 | — | — |
| GD 22.5 | 2 | 7 | 2 | 2 | 1 |
| GD 23.0 | 2 | — | 2 | 3 | 3 |
| GD 23.5 | — | — | — | — | — |
| Sacrificed GD 24* | — | — | 3 | 3 | 6 |
| Mean Length of Gestation ± SD | 22.3 ± 0.4 | 22.8 ± 0.4 | 22.7 ± 0.7 | 22.8 ± 0.3 | 22.9 ± 0.2 |

*Sacrificed on GD 24 due to failure to initiate or complete parturition.

These effects are probably pharmacologically mediated through the local inhibition of placental 5α-reductase type 1, resulting in decreased progesterone catabolism. Prior to parturition, a decrease in the ration of uterine progesterone/estradiol, has been shown to be necessary for the onset of synchronous uterine contractions and successful delivery. (Maltier, et al. 1993) In this regard, administration of exogenous progesterone has been shown to prolong pregnancy and impair myometrial contractile activity in the rat. In the rat uterus, nuclear progesterone receptor concentration increases sharply from GD 20. Uterine and placental metabolism of progesterone also increases substantially during the last trimester of pregnancy in the rat, primarily due to the enhanced activity of 5α-reductase, 3α-hydroxysteroid dehydrogenase and 20α-hydroxysteroid dehydrogenase. Example 4 demonstrated high levels of 5α-reductase type 1 in the rat placenta.

EXAMPLE 2

In order to determine if termination of drug treatment with the 5α-reductase type 1 inhibitor 3-oxo-4-aza-4,7β-dimethyl-16β-(4-chlorophenoxy)-5α-androstane ("test compound") on GD 17, 19 or 20 would allow the 3-oxo-4-aza-4,7β-dimethyl-16β-(4-chlorophenoxy)-5α-androstane-treated pregnant females to initiate and complete parturition, Sprague-Dawley rats (Charles River Laboratories, Raleigh, N.C.) were approximately ten weeks of age and weighted 223 to 276 grams on Gestation Day 0 (GD 0, the day of finding copulatory plugs). The design of the study is as described below. All animals were housed and fed as described in Example 1, with the exception of a 1 hour transient electrical failure, during which power outage dim illumination was provided by emergency backup lighting.

A dose of 20 mg/kg/day of the test compound was given once daily by oral gavage to the three treatment groups of 10 mated females each, designated by the treatment interval (GD 6–17, GD 6–19, and GD 6–20), at a dose volume of 5 mL/kg. (GD 6–17 received treatment from Gestational Day 6 through 17, etc.) An additional group of 10 females similarly received the vehicle (0.5% methylcellulose in deionized water with 0.02% sodium lauryl sulfate (SLS)) on GD 6–20 and served as the control.

| Treatment Group | Treatment Interval | Number Assigned |
|---|---|---|
| Control (0.5% methylcellulose 0.02% SLS) | GD 6-20 | 10 |
| Test compound | | |
| 20 mg/kg/day | GD 6-17 | 10 |
| 20 mg/kg/day | GD 6-19 | 10 |
| 20 mg/kg/day | GD 6-20 | 10 |

In all test compound-treated groups there were increases in the length of gestation, relative to controls, regardless of the dosing interval (GD 6–17, GD 6–19 and GD 6–20). In the drug treated groups dosed during GD 6–19 and GD 6–20 there were drug-related increases in the number of pregnant females that failed to initiate or complete delivery (1/10 and 2/9) respectively. The data are summarized below as the number of pregnant females completing parturition on various days of gestation:

| Delivery Day | Control | 20 mg/kg/day GD 6-17 | GD 6-19 | GD 6-20 |
|---|---|---|---|---|
| GD 22.0 | 5 | 3 | 1 | — |
| GD 22.5 | 2 | 1 | 3 | — |
| GD 23.0 | 3 | 6 | 4 | 5 |
| GD 23.5 | — | — | 1 | — |
| GD 24 | — | — | — | 2 |
| Sacrificed GD 24* | — | — | 1 | 2 |
| Mean Length of Gestation ± SD | 22.4 ± 0.5 | 22.6 ± 0.5 | 22.8 ± 0.4 | 23.3 ± 0.5 |

*Sacrificed on GD 24 due to failure to initiate or complete parturition.

Similar findings were noted in the experiment of Example 1. These effects may be pharmacologically mediated through local inhibition of placental 5α-reductase type 1, resulting in decreased progesterone catabolism.

EXAMPLE 3

In order to determine if the effects in the experiments conducted in Examples 1 and 2 were due to decreased progesterone catabolism associated with inhibition of 5α-reductase by the 5α-reductase type 1 inhibitor 3-oxo-4-aza-4,7β-dimethyl-16β-(4-chlorophenoxy)-5α-androstane ("test compound"), the following study was performed with the 5α-reductase inhibitor 3-oxo-4-aza-4,7β-dimethyl-16β-(4-chlorophenoxy)-5α-androstane and the progesterone antagonist RU-486.

Fifty-six pregnant female Sprague-Dawley rats (Charles River Laboratories, Raleigh, N.C.), approximately 10.5 weeks old weighing from 212 to 319 grams were employed in the study. They were fed and housed as described in EXAMPLE 1. The females were assigned to the following groups based on a weight independent random allocation scheme:

| Treatment Group | Number Assigned |
| --- | --- |
| Group 1: Control (Control article) | 14 |
| Group 2: Control article and on GD 21 RU-486 @ 10 mg/kg | 14 |
| Group 3: test compound @ 20 mg/kg/day | 14 |
| Group 4: test compound @ 20 mg/kg/day and on GD 21 RU-486 @ 10 mg/kg | 14 |

The dose of 20 mg/kg/day of the test compound was selected based on the results of EXAMPLE 1, in which there were drug-related increases in the incidence of females that failed to initiate or complete parturition when the dams were dosed with 5–20 mg/kg/day during GD 6 through LD 20. A dose of 10 mg/kg off RU-486 was selected based on the studies of Abdellilah et al., Progesterone and Mifepristone modify principally the response of circular myometrium to oxytocin in preparturient rats: comparison with response to acetylcholine and to calcium *J. Pharmacol. and Exp. Therp.* 265(3):1205–1212 (1993), in which an oral dose of 10 mg/kg of RU-486 on GD 21 was able to induce parturition in pregnant rats treated with 200 mg/kg progesterone subcutaneously.

The drugs were administered by oral gavage. The control article and vehicle consisted of 0.5% methylcellulose in deionized water with 0.02% sodium lauryl sulfate (SLS) and were prepared on a weekly basis and refrigerated when not in use. The test compound formulation (4 mg/mL, in vehicle) was prepared on a weekly basis and was refrigerated when not in use. The RU-486 formulation (2 mg base compound/mL, in 0.5% methylcellulose in deionized water) was prepared on a daily basis.

In Groups 1 and 3 (0.5% methylcellulose control group and the group receiving 20 mg/kg/day of test compound, respectively) mean serum progesterone values decreased as expected on GD 15 through GD 21. However, in Group 3 mean serum progesterone values were approximately 1.6, 1.4, 1.6 and 3.3 times above control group 1 serum progesterone values on GD 15, 17, 19 and 21, respectively. These findings are considered to be pharmacologically mediated through the decreased progesterone catabolism associated with inhibition of type 1 5α-reductase by the test compound. In Group 3, there was a positive correlation between high individual serum progesterone values on GD 21 and the failure to initiate or complete parturition.

In Group 3 (20 mg/kg/day test compound), there was a drug related increase in females that failed to initiate or complete parturition. In females that completed parturition in Group 3, there was a drug related increase in the mean length of gestation (23.3 days vs. 22.3 days in control Groups 1 and 2). In light of the elevated serum progesterone levels in Group 3, these findings are considered to be pharmacologically mediated through inhibition of type 1 5α-reductase by the test compound. In Group 4, all dams treated with test compound were able to complete parturition following the administration of RU-486 on GD 21. The fact that all pregnant females in this group completed delivery supports the hypothesis that the elevated serum progesterone levels associated with treatment with the 5α-reductase type 1 inhibitor 3-oxo-4-aza-4,7β-dimethyl-16β-(4-chlorophenoxy)-5α-androstane are responsible for the adverse effects on parturition noted with the test compound. The length of gestation data are summarized below as the number of females completing parturition on various days of gestation:

| Delivery Day | Control | Control/ RU-486 | test compound | test compound/ RU-486 |
| --- | --- | --- | --- | --- |
| GD 22.0 | 7 | 7 | 1 | 4 |
| GD 22.5 | 2 | 5 | — | 3 |
| GD 23.0 | 3 | 2 | 2 | 6 |
| GD 23.5 | — | — | — | — |
| GD 24 | — | — | 3 | — |
| Sacrificed Early * | — | — | 7 | — |
| Mean Length of Gestation ± SD$^a$ | 22.3 ± 0.4 | 22.3 ± 0.4 | 23.3 ± 0.8 | 22.6 ± 0.4 |

* Sacrificed on GD 24 due to failure to initiate or complete parturition.
$^a$includes only females completing delivery

EXAMPLE 4

5α-reductase content of rat placenta

The 5α-reductase content of microsomes prepared from rat placenta was determined.

Rat placenta was obtained from Bioproducts for Science. The tissue was homogenized in 10 volumes of buffer containing 0.25 sucrose, 40 mM potassium phosphate pH 6.5, 5 mM magnesium sulfate, 25 mM potassium chloride, 1 mM phenylmethylsulfonyl fluoride, and 1 mM dithiothreitol using a Potter Elverhjem homogenizer. The homogenate was centrifuged at 100,000×g for 60 minutes at 4° C. The pellet was resuspended in 1.5 volumes of buffer. Glycerol was added to the resuspended pellet to a final concentration of 20%. COS cell expressed rat 5α-reductase was used as the source of type 1 and type 2 in these studies for comparison.

All samples in the enzyme assay were tested in a reaction mixture containing 33 mM succinic acid, 44 mM imidazole, 33 mM diethanolamine (SID), pH 5.5 and pH 7.5, 0.5 μM [7-$^3$H]-testosterone (specific activity approximately 20–30 Ci/mmol), 1.5 μM unlabeled testosterone, 1 mM DTT and 500 mM NADPH in a final volume of 100 mL. The assay was initiated by the addition of enzyme and incubated at 37° C. for 15 min.

High levels of 5α-reductase were present in this tissue (131 pmol/min/mg). This about nine-fold higher than normally seen for rat prostate. The isozyme present in this tissue was determined by taking advantage of the difference in pH optimum for the rat type 1 (neutral) and type 2 (acidic) 5α-reductases. Highest levels of 5α-reductase are found at neutral pH as expected for a type 1 5α-reductase. The Km value of 5.2 μM for the activity in rat placenta microsomes is also in good agreement for the type 1 5α-reductase (1.7 μM). Similarly, the $IC_{50}$ for finasteride of 11 nM agrees well with the value of 13 nM obtained with the recombinant rat type 1 5α-reductase. A summary of the properties of the 5α-reductase in rat placenta is provided in the table below:

TABLE

Properties of the 5α-reductase in rat placenta

| Source | pH optimum | Km (μM) testosterone | $IC_{50}$ (nM) finasteride |
| --- | --- | --- | --- |
| rat placenta | ~7.0 | 5.2 | 11 |
| rat type 1 | ~6.5 | 1.7 | 13 |
| rate type 2 | 5.5 | 0.15 | 1 |

EXAMPLE 5

Synthesis of 7β,20-Dimethyl-4-aza-5α-pregna-17-en-3-one

Step 1: 3-Acetoxy-pregn-5-en-20-ol

Sodium borohydride (21 gm) was added to a solution of pregnenolone acetate (100 g, 0.28 mol) in absolute ethanol (1 L) and methylene chloride (0.4 L) at −10° C. After stirring overnight at 4° C., another amount of sodium borohydride (10.5 gm) was added and the reaction stirred at room temperature overnight. The reaction mixture was quenched by pouring into 5% sodium phosphate monobasic (2 L) and extracted with methylene chloride. The organic extracts were dried over anhydrous magnesium sulfate and filtered through a pad of anhydrous sodium sulfate. The solvent was removed by rotoevaporation to give the title compound.

Step 2: 3-Acetoxy-20-tert-butyldimethylsilyloxy-pregn-5-ene

Imidazole (203.7 gm, 2.28 mol) was added to a stirred suspension of 3-acetoxy-pregn-5-en-20-ol (361 gm, 1 mol, product of Step 1) in dimethylformamide (3.7 L). t-Butyldimethylsilyl chloride (228.9 mg, 1.52 mol) was added over a 10–15 min period. The mixture was stirred at room temperature for 3 days. The dimethylformamide was removed by decantation and methanol (50 mL) was added to it. Water (4 L) was added and the solution extracted with ethyl acetate (2×4 L). The precipitate remaining behind after decantation was dissolved in ethyl acetate and added to the above ethyl acetate extracts. The combined solvent extracts were washed with water, saturated salt solution, and dried over anhydrous magnesium sulfate. The solvent was removed by rotoevaporation and the product purified by column chromatography on silica gel eluted with 2:1 hexane-methylene chloride followed by 1:1 hexane-methylene chloride. The title compound was isolated as a mixture of 20α- and β-isomers.

Step 3: 3-Acetoxy-20-tert-butyldimethylsiyloxy-pregn-5-en-7-one

To a solution of 3-acetoxy-20-tert-butyldimethylsilyloxy-pregn-5-ene (337 gm, 0.71 mol, product of Step 2) in methyl ethyl ketone (4 L) was added N-hydroxyphthalimide (115.8 gm, 0.71 mol) and dibenzoyl peroxide (1.1 gm, 4.4 mmol). Air was bubbled through the reaction as the reaction was refluxed for 7.5 hr. Additional N-hydroxyphthalimide (9 gm) and dibenzoyl peroxide (0.1 gm) were added and reflux continued for 5 hr. The solvent was removed by rotoevaporation and methylene chloride (0.7 L) was added and warmed to 40° C. Upon cooling to room temperature, the suspension was filtered and the filtrate washed with methylene chloride (0.2 L). The filtrate was rotoevaporated and treated with pyridine (1.35 L) and acetic anhydride (135 mL). After stirring overnight, the solvent was removed by rotoevaporation and the dark orange oil dissolved in methanol (0.6 L). The mixture was heated to 50° C. and then cooled to room temperature. The solution was allowed to stand for 3 days and then cooled in an ice bath. The precipitate was filtered, washed with methanol, and dried to yield the title compound. The filtrate was rotoevaporated to a dry gum to yield the crude product.

Step 4: 20-tert-Butyldimethylsilyloxy-7-methyl-pregn-5-ene-3,7-diol

A solution of 3-acetoxy-20-tert-butyldimethylsilyloxy-pregn-5-en-7-one (279 gm, 0.57 mol, product of Step 3) in tetrahydrofuran (5.6 L) was cooled to 4° C. A 3M solution of methyl magnesium chloride in tetrahydrofuran (1.037 L, 3.1 mol) was added at such a rate as to keep the temperature 0° C. The ice bath was removed and the reaction allowed to warm to room temperature overnight. The reaction was cooled in an ice bath and quenched with a 20% solution of ammonium chloride (3 L). The organic layer was removed and the aqueous layer extracted with ethyl acetate. The organic layers were combined, washed with saturated salt solution, and dried over anhydrous magnesium sulfate. The solution was filtered through a pad of anhydrous sodium sulfate and the solvent removed by rotoevaporation to yield the title compound.

Step 5: 20-tert-Butyldimethylsilyloxy-7-methyl-pregn-4,6-dien-3-one

A solution of 20-tert-butyldimethylsilyloxy-7-methyl-pregn-5-ene-3,7-diol (298 gm, 0.59 mol, product of Step 4) in toluene (3 L) and cyclohexanone (1.03 L) was azeotroped to remove 750 mL of solvent. A solution of aluminum isopropoxide (121 gm) in toluene (620 mL) was added and the solution azeotroped to remove another 650 mL of solvent. A reflux condenser was added and the solution refluxed overnight. The solution was cooled to 40° C. and Supercell™ (125 gm) and water (125 mL) were added. After stirring for 10 min, the mixture was filtered and the solids washed with toluene (550 mL). The solvent was removed by rotoevaporation to yield a orange liquid which was purified by column chromatography on silica gel eluted with hexane, followed by 5–10% ethyl acetate in hexanes. The title compound was isolated as a mixture of 20α- and 20β-isomers.

Step 6: 20-tert-Butyldimethylsilyloxy-7β-methyl-pregn-4-en-3-one

A slurry of 5% palladium on carbon (7.12 gm) and benzyl alcohol (213 mL) in heptane (356 mL) was refluxed for 20 min. The mixture was cooled to 80° C. and a solution of 20-tert-butyldimethylsilyloxy-7-methyl-pregn-4,6-dien-3-one (71.2 gm, 0.16 mol, product of Step 5) in heptane (427 mL) was added. The slurry was refluxed for 9.5 h. The reaction was cooled to room temperature and filtered through SOLKA FLOK filter aid which was subsequently washed with hexane. The filtrate was extracted with acetonitrile which was subsequently back-extracted with hexane. The heptane and hexane extracts were combined, washed with saturated sodium sulfate and saturated salt solutions, and dried over anhydrous magnesium sulfate. The solution was filtered through a pad of anhydrous sodium sulfate and the solvent removed by rotoevaporation. The title compound was purified by column chromatography on silica gel eluted with 7% ethyl acetate in hexanes.

Step 7: 20-tert-Butyldimethylsilyloxy-7β-methyl-5-oxo-A-nor-3,5-secopregnan-3-oic acid To a solution of 20-tert-butyldimethylsilyloxy-7β-methyl-pregn-4-en-3-one (73.57 gm, 0.165 mol, product of Step 6) in tert-butanol (0.96 L) was added a solution of sodium carbonate (25.8 gm) in water (120 mL). The mixture was heated to 80° C. with stirring. A warm solution of sodium periodate (244 gm) and potassium permanganate (1.91 gm) in water (0.96 L) was slowly added and then the reaction refluxed for 2 h. The reaction was cooled to room temperature and filtered through a pad of SuperCell™. The filter cake was washed with water (2×190 mL). The combined filtrates were rotoevaporated to remove the tert-butanol and washed with methylene chloride. The aqueous solution was acidified to pH~3 with 2N hydrochloric acid and extracted with methylene chloride (3×). The organic extracts were combined, washed with 5% sodium bisulfite solution and saturated salt solution, and dried over anhydrous magnesium sulfate. The solvent was removed by rotoevaporation to yield the title compound as a white foam.

Step 8: 20-tert-Butyldimethylsilyloxy-7β-methyl-4-azapregn-5-ene

To a solution of 20-tert-butyldimethylsilyloxy-7β-methyl-5-oxo-A-nor-3,5-secopregnan-3-oic acid (26 gm., 56 mmol, product of Step 7) in ethylene glycol (500 mL) under nitrogen was added anhydrous ammonium acetate (50 gm). The mixture was heated at 180° C. for 5 h, cooled to room temperature, and diluted with water (3.5 L). After stirring for 1 hr, the solid was filtered and the aqueous layer was extracted with methylene chloride (500 mL). The organic layer was dried over anhydrous magnesium sulfate and the solvent removed by rotoevaporation. The residue was combined with the filtered solid and dried in a vacuum oven overnight to give the title compound.

Step 9: 20-tert-Butyldimethylsilyloxy-7β-methyl-5α-4-azapregnane

To a solution of 20-tert-butyldimethylsilyloxy-7β-methyl-4-azapregn-5-ene (23.9 g, 53.6 mmol, product of Step 8) in acetic acid (250 mL) was added platinum oxide (1.8 gm). The mixture was stirred overnight under hydrogen (1 atmosphere). The reaction mixture was filtered through a pad of Celite™ filter aid (trademark for diatomaceous earth) and the filtrate was coevaporated with toluene (3×500 mL) to remove all of the acetic acid. The residue was dissolved in chloroform and filtered again through a pad of Celite™ filter aid to remove residual catalyst. The solvent was removed by roto-evaporation to yield the title compound which was taken directly on to the next step without any further purification.

Step 10: 20-Hydroxy-7β-methyl-5α-4-azapregnan-3-one

To a slurry of crude 20-tert-butyldimethylsilyloxy-7β-methyl-5α-4-azapregnane (25.2 g, product of Step 9) in acetonitrile (300 mL) was added an aqueous solution of hydrofluoric acid (12 mL). After stirring for 8 hr at room temperature, the reaction mixture was cooled to 0° C. and saturated sodium bicarbonate solution was slowly added. The mixture was extracted with methylene chloride (3×500 mL) and the combined extracts washed with water, saturated salt solution and dried over anhydrous sodium sulfate. The solvent was removed by rotoevaporation to give the title compound which was used without purification in the subsequent reaction.

Step 11: 7β-Methyl-5α-4-azapregnane-3,20-dione

To a stirred solution of 20-hydroxy-7β-methyl-5α-4-azapregnan-3-one (22.3 gms, 67 mmol, product of Step 10) in dry methylene chloride under nitrogen (110 mL) was added 4-methyl morpholine N-oxide (11.8 gms, 100 mmol) followed by 4 Å molecular sieves (33 gm). To this mixture was added tetrapropylammonium perruthenate (1.2 gm). After stirring at room temperature for 4 h, the reaction mixture was poured through pad of silica gel in a 300 mL sintered glass funnel which was subsequently eluted with 4:1 ethyl acetate/methylene chloride (5 L). The solvent was removed by rotoevaporation and the title compound recrystallized.

Step 12: 20-Hydroxy-7β,20-dimethyl-4-aza-5α-pregnan-3-one

To a solution of 7β-methyl-4-aza-5α-pregnane-3,20-dione (1.24 g., 3.73 mmol., product of Step 11) in tetrahydrofuran (20 mL.) was added methylmagnesiumbromide in diethyl ether (3.73 mL., 11.2 mmol) at room temperature. The reaction was stirred for 45 minutes under a nitrogen atmosphere and then quenched with saturated ammonium chloride solution and diluted with ethyl acetate (500 mL.). The organic phase was washed with water (500 mL.,×2) and brine solution (300 mL.). It was dried over sodium sulfate, filtered and the solvent evaporated in vacuo to give a white foam. The foam was flash chromatographed on silica gel using methanol in methylene chloride (1:19) as the mobile phase to yield a white foam. The foam was then recrystallized in methylene chloride and hexane (1:4) to yield the titled compound as white crystals. Rf=0.35, 5% methanol-:methylene chloride. 400 MHz $^1$H NMR (CDCl$_3$): δ 0.82 (s, 3H); 0.87 (s, 3H); 1.16(s, 3H); 1.27 (s, 3H); 3.04 (dd, 1H).

Step 13: 7β,20-Dimethyl-4-aza-5α-pregn-17-en-3-one

A mixture of 20-Hydroxy-7β-methyl-4-aza-5α-pregnan-3-one (0.810 g., 2.35 mmol, product of Step 12), 2M hydrochloric acid (35 mL.) and tetrahydrofuran (THF, 35 mL.) was refluxed at 70° C. for 3 hours. THF was then evaporated in vacuo and the aqueous phase was basified using 2.5M sodium hydroxide. The aqueous phase was then extracted with methylene chloride (200 mL) three times. The organic phases were combined and washed water (500 mL.) and brine (300 mL.). The organic phase was then dried with sodium sulfate, filtered and the solvent evaporated in vacuo to give a yellow oil. The oil was recrystallized in methylene chloride and hexane (1:3) to give a yellow solid.

EXAMPLE 6

Synthesis of 7β,20-dimethyl-4-aza-5α-pregnan-3-one

To a solution of 7β,20-dimethyl-4-aza-5α-pregna-17-en-3-one (730 mg., 2.22 mmol, the product of Example 1) and methanol (40 mL) was added platinum oxide (250 mg). This mixture was stirred under a hydrogen atmosphere overnight. It was then filtered through Celite™ diatomaceous earth and the solvent was removed under vacuum. The crude residue was chromatographed using 10% 2-propanol in hexane as the mobile phase to yield the titled compound as a white solid. 400 MHz $^1$H NMR (CDCl$_3$): δ 0.66 (s, 3H); 0.83 (d, 3H); 0.85 (s, 3H); 0.91 (d, 3H); 0.99 (d, 3H); 3.05 (dd, 1H). Mass spec.=332 (M+1)

EXAMPLE 7

Synthesis of 7β,20-dimethyl-4-aza-5α-pregn-1-en-3-one

To a solution of 7β,20-dimethyl-4-aza-5α-pregna-3-one (500 mg., 1.51 mmol, the product of Example 2) in dry toluene (15 mL.) was added 2,3-dichloro-5,6-dicyano-1,4-benzoquinone (410 mg, 1.81 mmol), bis(trimethyl silyl) trifluoroacetamide (1.6 mL, 6.04 mmol) and triflic acid (0.00625 mL., 0.068 mmol). The mixture was stirred under nitrogen atmosphere overnight, followed by addition of methyl acetoacetate 90.032 mL., 0.30 mmol). The mixture was then refluxed overnight. The reaction mixture was poured into water (100 mL) containing sodium bicarbonate (800 mg.) and sodium sulfite (300 mg) and extracted with methylene chloride (3×100 mL). The organic phases were combined and washed with water (200 mL) and brine (100 mL). The organic phase was dried over sodium sulfate, filtered and the solvent evaporated in vacuo. The residue was purified by flash chromatography on silica gel eluded with 15% acetone in methylene chloride and recrystallization methyl ethyl ketone (MEK) to yield titled compound. 400 MHz $^1$H NMR (CDCl$_3$): δ 0.67 (s, 3H); 0.82 (d, 3H); 0.89 (s, 3H); 0.92 (d, 3H); 1.01 (d, 3H); 3.34 (dd, 1H); 5.78 (dd, 1H); 6.78 (d, 1H). Mass spec.=330 (M+1)

EXAMPLE 8

Synthesis of 7β,20-dimethyl-4-aza-5α-pregn-1,17-dien-3-one

The titled compound was synthesized in the same fashion as 7β,20-dimethyl-4-aza-5α-pregna-1-ene-3-one, starting with 7β,20-dimethyl-4-aza-5α-pregna-17-en-3-one with the exception it was purified by recrystallization in ethyl acetate. 400 MHz $^1$H NMR (CDCl$_3$): δ 0.85 (s, 3H); 0.90 (s, 3H); 1.04 (d, 3H); 1.54 (s, 3H); 1.68 (s, 3H); 3.34 (dd, 1H); 5.78 (dd, 1H); 6.78 (d, 1H). Mass spec.=328 (M+1)

EXAMPLE 9

Synthesis of 20-ethyl-4,7β-dimethyl-4-aza-5α-pregn-17-en-3-one

Step 1: Preparation of 20-Ethyl-20-hydroxy-7β-methyl-4-aza-5α-pregnan-3-one

The titled compound was synthesized in a similar fashion to 20-Hydroxy-7β,20-dimethyl-4-aza-5α-pregnane-3-one using 3M ethylmagnesium bromide in diethyl ether in place of the methylmagnesium bromide. 400 MHz $^1$H NMR (CDCl$_3$): δ 0.82 (s, 3H); 0.84 (t, 3H); 0.86 (s, 3H); 0.99 (d, 3H); 1.23 (s, 3H); 3.03 (dd, 1H). Mass spec.=343 (M−18)

Step 2: Preparation of 20-Ethyl-20-hydroxy-4,7β-dimethyl-4-aza-5α-pregnan-3-one

To a slurry of sodium hydride (8.0 mg., 0.2 mmol) and 20-Ethyl-20-hydroxy-7β-methyl-4-aza-5α-pregnan-3-one (63.0 mg., 0.17 mmol, product of Step 1) in tetrahydrofuran was added methyl iodide (15.0 μL., 2.55 mmol). The solution was allowed to stir under a nitrogen atmosphere at room temperature overnight. The reaction was quenched with water and extracted with ethyl acetate (2×100 mL.). The organic phase was washed with water (100 mL) and brine (100 mL) and dried over sodium sulfate. The solvent was evaporated in vacuo and the residue purified via flash chromatography on silica gel eluding with 10% acetone in methylene chloride to yield the titled compound as a white foam. 400 MHz $^1$H NMR (CDCl$_3$): δ 0.81–0.84 (t, 3H); 0.083 (s, 3H); 0.85 (s, 3H); 1.03 (d, 3H); 1.22 (s, 3H); 2.9 (s, 3H); 2.99 (dd, 1H). Mass spec.=375 (M+)

Step 3: 20-ethyl-4,7β-dimethyl-4-aza-5α-pregn-17-en-3-one

The titled compound was synthesized in a similar fashion to 7β,20-dimethyl-4-aza-5α-pregna-17-ene-3-one and taken forward without any purification.

EXAMPLE 10

Synthesis of 20-ethyl-4,7β-dimethyl-4-aza-5α-pregnan-3-one

The titled compound was synthesized in a similar fashion to 7β,20-dimethyl-4-aza-5α-pregnane-3-one, starting with the product of Example 5. 400 MHz $^1$H NMR (CDCl$_3$): δ 0.64 (d, 3H); 0.79 (d, 3H); 0.83 (s, 3H); 0.88 (d, 3H); 1.04 (d, 3H); 2.89 (s, 3H); 3.0 (dd, 1H). Mass spec.=359 (M+)

EXAMPLE 11

Synthesis of 20-propyl-4,7β-dimethyl-4-aza-5α-pregnan-3-one

Step 1: 20-Allyl-20-hydroxy-7β-methyl-4-aza-5α-pregnan-3-one

The titled compound was synthesized in a similar fashion to 20-Hydroxy-7β,20-dimethyl-4-aza-5α-pregnan-3-one using 2M allylmagnesium chloride in tetrahydrofuran in place of the methylmagnesium bromide. No further purification was done prior to the following step.

Step 2: 20-Allyl-20-hydroxy-4,7β-dimethyl-4-aza-5α-pregnan-3-one

The titled compound was synthesized in a fashion similar to 20-ethyl-20-Hydroxy-4,7β-dimethyl-4-aza-5α-pregnan-3-one. 400 MHz $^1$H NMR (CDCl$_3$): δ 0.82 (s, 3H); 0.85 (s, 3H); 1.03 (d, 3H); 1.26 (s, 3H);2.89 (s,3H); 3.00 (dd, 1H); 5.05 (dd, 2H); 5.78 (m, 1H).

Step 3: 20-propyl-4,7β-dimethyl-4-aza-5α-pregnan-3-one

A slurry of 20-allyl-20-Hydroxy-4,7β-dimethyl-4-aza-5α-pregnan-3-one (29.0 mg., 0.075 mmol), 10% palladium on carbon (5.0 mg.) and a mixture of ethyl acetate-ethanol (5.0 mL., 1:1) was stirred for 48 hours under a hydrogen atmosphere at room temperature. The reaction was then filtered through Celite™ and the solvent evaporated in vacuo. The residue was purified via HPLC on a Waters 19×300 mm 8μ silica Nova Pak column using a 5 to 10% 2-propanol/hexane linear gradient at a 20 mL. per minute flow rate to yield the titled compound. 400 MHz $^1$H NMR (CDCl$_3$): δ 0.65 (s, 3H); 0.80 (m, 9H); 1.02 (d, 3H); 2.89 (s, 3H); 3.00 (dd, 1H). Mass spec.=373 (M+)

EXAMPLE 12

Oral Composition

As a specific embodiment of an oral composition of a compound of this invention, 10 mg of 3-oxo-4-aza-4,7β-dimethyl-16β-(4-chlorophenoxy)-5α-androstane is formulated with sufficient finely divided lactose to provide a total amount of 580 to 590 mg to fill a size 0 hard gelatin capsule.

EXAMPLE 13

Oral Composition

As a specific embodiment of an oral composition of a compound of this invention, 20 mg of 3-oxo-4-aza-4,7β-dimethyl-16β-phenoxy-5α-androstane is formulated with sufficient finely divided lactose to provide a total amount of 580 to 590 mg to fill a size 0 hard gelatin capsule.

EXAMPLE 14

Oral Composition

As a specific embodiment of an oral composition of a compound of this invention, 15 mg of 3-oxo-4-aza-7-methyl-16β-(4-methylphenoxy)-5α-androst-1-ene is formulated with sufficient finely divided lactose to provide a total amount of 580 to 590 mg to fill a size 0 hard gelatin capsule.

EXAMPLE 15

Oral Composition

As a specific embodiment of an oral composition of a compound of this invention, 5 mg of 17β-N-(2,5-bis (trifluoromethyl)) phenyl carbamoyl-4-aza-5α-androst-1-en-3-one is formulated with sufficient finely divided lactose to provide a total amount of 580 to 590 mg to fill a size 0 hard gelatin capsule.

EXAMPLE 16

Transdermal Patch Formulation

| Ingredient | Amount |
| --- | --- |
| 5α-reductase type 1 inhibitor | 40 g |
| Silicone fluid | 45 g |
| Colloidal silicone dioxide | 2.5 g |

The silicone fluid and 5α-reductase type 1 inhibitor compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 cm² patches. For 100 Patches.

EXAMPLE 17

Suppository

| Ingredient | Amount |
| --- | --- |
| 5α-reductase type 1 inhibitor | 25 g |
| Polyethylene glycol 1000 | 1481 g |
| Polyethylene glycol 4000 | 494 g |

The polyethylene glycol 1000 and polyethylene glycol 4000 are mixed and melted. The 5α-reductase type 1 inhibitor is mixed into the molten mixture, poured into molds and allowed to cool. For 1000 suppositories.

EXAMPLE 18

Vaginal Suppository

| Ingredient | Amount |
| --- | --- |
| 5α-reductase type 1 inhibitor | 25 g |
| Water | 175 mL |
| Glycerin | 1400 g |
| Pharmagel B | 310 g |
| Methylparaben | 10 g |

The 5α-reductase type 1 inhibitor is dispersed in water. Glycerin is added, followed by addition of Pharmagel B and methylparaben. The mixture is poured into molds. For 1000 suppositories.

EXAMPLE 19

Injectable Solution

| Ingredient | Amount |
| --- | --- |
| 5α-reductase type 1 inhibitor | 10 g |
| Buffering agents | q.s. |

-continued

| Ingredient | Amount |
| --- | --- |
| Porpylene glycol | 400 mg |
| Water for injection | 600 mL |

The 5α-reductase type 1 inhibitor and buffering agents are dissolved in the propylene glycol at about 50° C. The water for injection is then added with stirring and the resulting solution is filtered, filled into ampules, sealed and sterilized by autoclaving. For 1000 Ampules.

EXAMPLE 20

Injectable Solution

| Ingredient | Amount |
| --- | --- |
| 5α-reductase type 1 inhibitor | 10 g |
| Buffering agents | q.s. |
| Magnesium sulfate heptahydrate | 100 mg |
| Water for injection | 880 mL |

The 5α-reductase type 1 inhibitor, magnesium sulfate heptahydrate and buffering agents are dissolved in the water for injection with stirring, and the resulting solution is filtered, filled into ampules, sealed and sterilized by autoclaving. For 1000 Ampules.

EXAMPLE 21

Injectable Solution

| Ingredient | Amount |
| --- | --- |
| 5α-reductase type 1 inhibitor | 10 g |
| Ritodrine HCl | 10 g |
| Acetic Acid | 4.25 g |
| Sodium metabisulfite | 100 mg |
| Sodium hydroxide | 3.0 g |
| Water for injection | 970 mL |

The 5α-reductase type 1 inhibitor, ritodrine HCl, acetic acid, sodium metabisulfite and sodium chloride are dissolved in the water for injection with stirring, and the resulting solution is filtered. Hydrochloric acid or sodium hydroxide are used to adjust pH. Ampules are filled under nitrogen. For 1000 Ampules.

EXAMPLE 22

Treatment Protocol

A patient undergoing premature labor is administered an amount of a 5α-reductase type 1 inhibitor sufficient to quiet labor. If labor recurs again once the patient is off of the drug, the administration of the 5α-reductase type 1 inhibitor is begun again and maintained for a longer period of time.

EXAMPLE 23

Preparation of Human Prostatic and Scalp 5α-Reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

EXAMPLE 24

5α-Reductase Assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μL. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μL. Typically, the assay was initiated by the addition of 50–100 μg prostatic homogenate or 75–200 μg scalp homogenate and incubated at 37° C. After 10–50 min the reaction was quenched by extraction with 250 μL of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman Partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655α Autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. IC$_{50}$ values represent the concentration of inhibitor required to decrease enzyme conversion of testosterone to dihydrotestosterone by 50% of the control. IC$_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5αreductase 2 inhibitor is a compound that shows inhibition of the 5α-reductase 2 isozyme in the above-described assay, having an IC$_{50}$ value of about or under 100 nM.

The compounds are tested in the above-described assay for 5α-reductase type 1 and type 2 inhibition, and were found to have IC$_{50}$ values under about 100 nM for inhibition of the type 1 isozyme. Compounds found to have IC$_{50}$ values of under about 50 nM for inhibition of the type 1 isozyme are called type 1 inhibitors. Compounds called "dual inhibitors" additionally had IC$_{50}$'s under about 200 nM for inhibition of the type 2 isozyme.

EXAMPLE 25

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A. G., "The Culture of Dermal Papilla Cells From Human Hair Follicles," Br. *J. Dermatol.*, 110:685–689 (1984) and Itami, S. et al., "5α-Reductase Activity In Cultured Human Dermal Papilla Cells From Beard Compared With Reticular Dermal Fibroblasts," *J. Invest. Dermatol.*, 94:150–152 (1990). Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM MgCl$_2$, and 2 mM CaCl$_2$, by vortexing and 10 passes through a 25-gauge needle. The crude homogenate is further homogenized by a Teflon-glass homogenizer, and is used as the cell homogenate. For the study of subcellular localization of 5α-reductase, the cell homogenate is centrifuged at 800×g for 10 min to yield a crude nuclear pellet. The resultant supernatant is centrifuged at 10,000×g for 15 min to produce a crude mitochondrial pellet. The supernatant is centrifuged at 100,000×g for 60 min to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 mL of the cell homogenate, in a final volume of 100 mL. Each tube contains 50–100 mg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," *J. Biol. Chem.*, 193:265–275 (1951).

After incubation, the reaction is stopped by adding 4 times volume of chloroform-methanol (2/1:V/V) containing 110 mg each of carrier steroids. The extracted steroids are analyzed by thin-layer chromatography as previously described by Gomez, et al., "In Vitro Metabolism Of Testosterone-4-$^{14}$C and D-androstene-3, 17-dione-4-$^{14}$C In Human Skin.," *Biochem.*, 7:24–32 (1968), and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intented, therefore, that the invention be defined by the scope of the claims which follow and that such claims be interpreted as broadly as a reasonable.

What is claimed is:

1. A method of treating preterm labor in a mammal in need thereof, comprising administering to the mammal a therapeutically effective amount of an inhibitor of 5α-reductase type 1.

2. The method of treating preterm labor according to claim 1 wherein the inhibitor of 5α-reductase type 1 is selected from:

(I) a compound of structural formula (I):

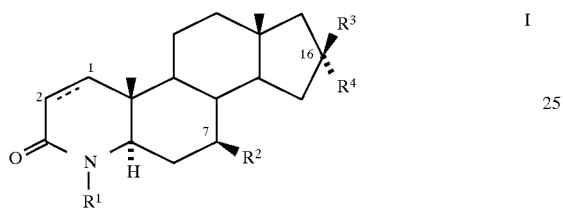

or a pharmaceutically acceptable salt or ester thereof wherein:

the C1–C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:

(a) amino;
(b) cyano;
(c) fluoro;
(d) methyl;
(e) OH;
(f) —C(O)NR$_b$R$_c$, where R$_b$ and R$_c$ are independently H, $C_{1-6}$ alkyl, aryl, or aryl $C_{1-6}$ alkyl; wherein the alkyl moiety can be substituted with 1–3 of: halo; $C_{1-4}$alkoxy;

or trifluoromethyl; and the aryl moiety can be substituted with 1–3 of: halo; $C_{1-4}$ alkyl; $C_{1-4}$ alkoxy; or trifluoromethyl;

(g) $C_{1-10}$ alkyl-X—;
(h) $C_{2-10}$ alkenyl-X—;

wherein the $C_{1-10}$ alkyl in (g) and $C_{2-10}$ alkenyl in (h) can be unsubstituted or substituted with one to three of:

(i) halo; hydroxy; cyano; nitro; mono-, di- or trihalomethyl; oxo; hydroxysulfonyl; carboxy;
(ii) hydroxy $C_{1-6}$ alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;
(iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
(iv) —C(O)NR$_b$R$_c$; —N(R$_b$)—C(O)—R$_c$; —NR$_b$R$_c$;

where R$_b$ and R$_c$ are defined above;

(i) aryl-X—;
(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

wherein the aryl in (i) and heteroaryl in (j) can be unsubstituted or substituted with one to three of:

(v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;
(vi) $C_{1-6}$ alkyl; hydroxy $C_{1-6}$ alkyl; $C_{1-6}$ alkyloxy; $C_{1-6}$ alkyloxy $C_{1-6}$ alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$ alkyl; R$_b$R$_c$N—C(O)—$C_{1-6}$ alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;
(vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$ alkyl; $C_{1-4}$alkoxy; or trifluoromethyl;
(viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is $C_{1-6}$ alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$ alkyl; $C_{1-4}$ alkoxy, or trifluoromethyl; —N(R$_b$)—C(O) NR$_c$R$_d$, wherein R$_d$ is selected from H, $C_{1-6}$ alkyl, and aryl; in which said $C_{1-6}$ alkyl and aryl can be substituted as described above in (f) for R$_b$ and R$_c$;
(ix) a heterocyclic group, which is a 5, 6 or 7 membered ring, containing at least one member selected from the group consisting of:

one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for (v), (vi), (vii) and (viii), excluding (ix) a heterocyclic group; and (k) $R^3$ and $R^4$ taken together can be carbonyl oxygen;
(l) $R^3$ and $R^4$ taken together can be 50 CH—R$_g$, wherein R$_g$ is defined in viii); and wherein:

X is selected from the group consisting of:

—O—; —S(O)$_n$—; —C(O)—; —CH(R$_e$)—; —C(O)—O—*; —C(O)—N(R$_e$)—*; —N(R$_e$)—C(O)—O—*; —O—C(O)—N(R$_e$)—*; —N(R$_e$)C(O)—N(R$_e$)—;

—O—CH($R_e$)—\*; —N($R_e$)—; wherein $R_e$ is H, $C_{1-3}$ alkyl, aryl, aryl- $C_{1-3}$ alkyl, or unsubstituted or substituted heteroaryl, as defined above in (j);

wherein the asterisk (\*) denotes the bond which is attached to the 16-position in Structure I; and n is zero, 1 or 2;

(II) a compound of structural formula (II):

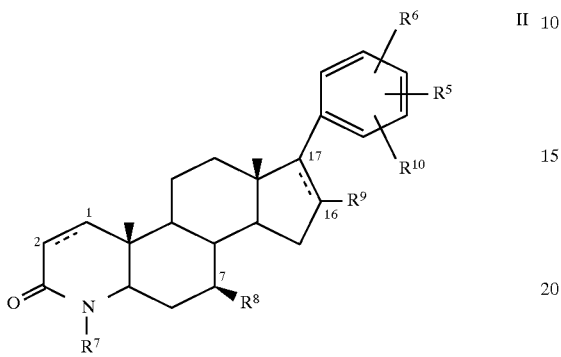

or a pharmaceutically acceptable salt or ester thereof, wherein: the C1–C2 bond and the C16–C17 bond designated "---" each independently represent a single or double bond;

$R^7$ and $R^8$ are independently selected from:
(1) —H,
(2) —$CH_3$ and
(3) —$CH_2CH_3$;

$R^9$ is selected from:
(1) —H and
(2) —$CH_3$; and $R^9$ is β-oriented if C16–C17 is saturated;

$R^{10}$, $R^5$ and $R^6$ are independently selected from:
(1) —H,
(2) —$C_{1-8}$ alkyl, unsubstituted or substituted with —OH,
(3) —$C_{1-3}$ perfluoroalkyl,
(4) —halo,
(5) —OR$^{11}$, wherein $R^{11}$ is
  (a) —H,
  (b) —$C_{1-8}$ alkyl,
  (c) —$C_{1-6}$ alkylcarbonyl,
  (d) —$C_{1-6}$ alkylsulfonyl, or
  (e) —$C_{1-6}$ alkoxycarbonyl,
(6) —NHR$^{11}$,
(7) —$NO_2$,
(8) —S($C_{1-6}$ alkylcarbonyl),
(9) —S(O)$_n C_{1-8}$ alkyl, wherein n is 0, 1 or 2,
(10) —$CO_2 R^{12}$ wherein $R^{12}$ is
  a) —H or
  b) —$C_{1-8}$ alkyl,
(11) —C(O)$R^{12}$,
(12) —C(O)N($R^{12}$)$_2$,
(13) —CN,
(14) —C($R^{12}$)$_2$OR$^{11}$,
(15) —C($R^{12}$)$_2$NR$^{11}$,
(16) —C($R^{12}$)$_2$S($C_{1-8}$ alkyl),
(17) —C($R^{12}$)$_2$S($C_{1-6}$ alkylcarbonyl), and
(18) phenyl, unsubstituted or having 1 to 3 substituents selected from:
  (a) —OH,
  (b) halo,
  (c) $C_{1-3}$ alkyl, and
  (d) $C_{1-3}$ alkoxy; or $R^{10}$ and $R^5$ or $R^5$ and $R^6$, on vicinal carbon atoms, may be joined to form with the phenyl to which they are attached a naphthyl or indanyl group; and the 17-position substituent is β-oriented if C16–C17 is saturated;

(III) a compound of structural formula VII:

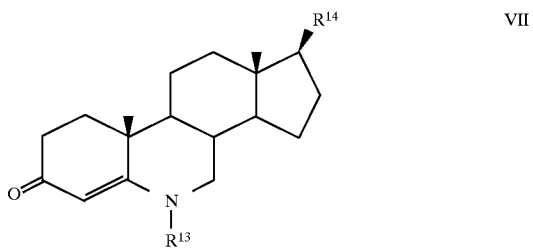

or a pharmaceutically acceptable salt or ester thereof, wherein:

$R^{13}$ is selected from —H, —$CH_3$ and —$CH_2CH_3$;

$R^{14}$ is selected from:
(1) —H, —OH, —$NH_2$, or =O,
(2) —$C_{1-12}$ alkyl,
(3) —$C_{1-12}$ alkyl-phenyl,
(4) —O—$C_{1-12}$ alkyl or —S(O)$_n$—$C_{1-12}$ alkyl,
(5) —O-Het or —S(O)$_n$-Het,
(6) —O-phenyl or —S(O)$_n$-phenyl,
(7) —$C_{1-6}$ alkyl-X-$C_{1-12}$ alkyl,
(8) —$C_{1-6}$ alkyl-X-Het,
(9) —C(O)-phenyl,
(10) —X—C(O)—$C_{1-12}$ alkyl,
(11) —OC(O)—NH$C_{1-12}$ alkyl,
(12) —OC(O)—NH-phenyl,
(13) —CN, and
(14) —NR$^{15}$R$^{16}$, wherein $R^{15}$ and $R^{16}$ are each independently selected from —H, $C_{1-12}$ alkyl, phenyl and Het;

Het is selected from piperidinyl, piperizinyl, pyrrolidinyl, pyrrolyl, furanyl and thienyl;

X is selected from the group consisting of O, NH and S(O)$_n$; and n is zero, 1 or 2;

(IV) a compound of structural formula (VIII):

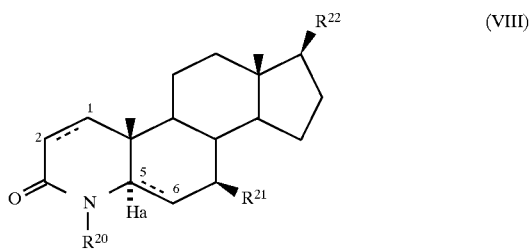

wherein:
the C1–C2 and C5–C6 bonds designated with a dotted line each independently represent a single or double bond, provided that when the C5–C6 is a double bond, $H_a$ is absent and when the C5–C6 bond is a single bond $H_a$ is present and represents hydrogen;

$R^{20}$ is selected from hydrogen and $C_{1-5}$ alkyl;

$R^{21}$ is $C_{1-5}$ alkyl, either straight or branched chain; and $R^{22}$ is $C_{3-7}$ alkyl, either straight or branched chain, optionally having one degree of unsaturation;

(V) a compound of structural formula (XI):

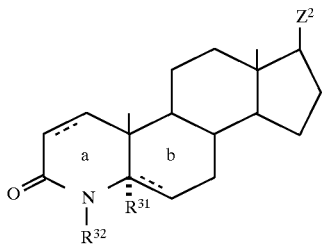

wherein "a" and "b" are both single bonds and $R^{31}$ is hydrogen, or

"a" is a double bond, "b" is a single bond and $R^{31}$ is hydrogen, or

"a" is a single bond, "b" is a double bond and $R^{31}$ is absent;

$Z^2$ is —$XR^{33}$, or —$(CHR^{30})_n$—$XR^{33}$;

n is an integer selected from 1–10;

X is —O— or —$S(O)_p$—,
wherein p is zero, 1 or 2;

$R^{30}$ is —H, aryl, or —$C_{1-3}$ alkyl unsubstituted or substituted with aryl and when n is greater than 1, $R^{30}$ can be the same or different at each occurrence;

$R^{32}$ is —H, methyl, ethyl, —OH, —$NH_2$ or —$SCH_3$;

$R^{33}$ is (1) —$C_{1-20}$ alkyl, unsubstituted or substituted with one or more of:
 (a) —OH,
 (b) halo,
 (c) —$C_{1-8}$ alkoxy,
 (d) —$C_{1-10}$ alkenyl,
 (e) —$CONR^{34}R^{34}$, wherein $R^{34}$ is independently
  (i) —H,
  (ii) —$C_{1-8}$ alkyl unsubstituted or substituted with one or more of $R^{36}$, aryl or heterocycle, the aryl being unsubstituted or substituted with one or more of $R^{36}$ or $R^{38}$,
  (iii) aryl unsubstituted or substituted with one or more of $R^{36}$ or $R^{38}$, or
  (iv) heterocycle, unsubstituted or substituted with one or more of $R^{36}$ or $R^{38}$,
 (f) —$COOR^{35}$, wherein $R^{35}$ is
  (i) —H,
  (ii) —$C_{1-8}$ alkyl unsubstituted or substituted with one or more of $R^{36}$ or aryl, the aryl being unsubstituted or substituted with one or more of $R^{36}$ or $R^{38}$, or
  (iii) aryl, unsubstituted or substituted with one or more of $R^{36}$ or$R^{38}$,
 (g) —$S(O)_p$—$R^{35}$, wherein p is defined above,
 (h) —$N(R^{34})_2$,
 (i) aryl, unsubstituted or substituted with one or more of aryl, $R^{36}$ or $R^{38}$,
 (j) heterocycle, unsubstituted or substituted with one or more of $R^{36}$ or $R^{38}$,
 (k) —$C_{3-10}$ cycloalkyl, such as cyclohexyl, norbomyl, or adamantyl, unsubstituted or substituted with one or more of $R^{36}$ or $R^{38}$, or
  (1) —$CONR^{37}$—CO—$NHR^{37}$, wherein $R^{37}$ is —H, —$C_{1-8}$ alkyl, benzyl or cyclohexyl,
  (2) aryl, unsubstituted or substituted with one or more of aryl, $R^{36}$ or $R^{38}$, or
  (3) heterocycle or —$C_{3-10}$ cycloalkyl, either of which is unsubstituted or substituted with one or more of $R^{36}$ or $R^{38}$;

$R^{36}$ is (1) —OH,
 (2) —$C_{1-3}$ alkoxy,
 (3) —CN,
 (4) —$COOR^{35}$
 (5) —$C_{1-8}$alkyl-$COOR^{35}$,
 (6) —$NO_2$, or
 (7) -halo; and
 (8) amino, mono-$C_1$–$C_4$ alkylamino, di-$C_1$–$C_4$-alkylamino;

$R^{38}$ is (1) —$C_{1-8}$ alkyl, unsubstituted or substituted with one or more of aryl or $R^{36}$,
 (2) —CO—A, —$C_{1-8}$ alkyl—CO—A, —NHCO—A, or —$S(O)_p$—A, wherein p is defined above and A is
  (a) —H,
  (b) —$C_{1-8}$ alkyl, unsubstituted or substituted with one or more of
   (i) —$R^{36}$, or
   (ii) aryl, unsubstituted or substituted with one or more of $R^{36}$, or
  (c) aryl, unsubstituted or substituted with one or more of $R^{36}$,
 (3) —NHCO-heterocycle,
 (4) —$N(R^{39})_2$ or —$CON(R^{39})_2$ wherein $R^{39}$ is independently heterocycle, or —A,
 (5) —NHCO—$(CH_2)_q$—CO—$Q^1$, wherein q is 1–4, and $Q^1$ is —$N(R^{39})_2$ or —$OR^{39}$;
  with the proviso that when Z is —$OR^{33}$, $R^{32}$ is —H, a is a single bond and b is a single or double bond, $R^4$ is not isopentyl; and
  4,7-dimehtyl-4-aza-5α-cholestan-3-one;
   or a pharmaceutically acceptable salt, ester, or stereoisomer thereof.

3. The method of treating preterm labor according to claim 1 wherein the 50α-reductase type 1 inhibitor is selected from:
4-aza-4,7β-dimethyl-5α androstane-3,1 6-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5αandrostane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;

3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy]-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-[(4-phenyl)phenoxy]-5α-androstane;
3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
6-methyl-6-aza-androst-4-en-3,17-dione;
6-methyl-17-propyl-6-aza-androst-4-en-3-one;
6-methyl-6-aza-androst-4-en-3-one;
6-methyl-17-hydroxy-6-aza-androst-4-en-3-one;
6-methyl-17-t-butylcarbamoyloxy-6-aza-androst-4-en-3-one;
6-aza-cholest-4-en-3-one;
6-methyl-6-aza-cholest-4-en-3-one;
7β,20-dimethyl-4-aza-5α-pregn-17-en-3-one;
7β,20-dimethyl-4-aza-5α-pregn-1,17-dien-3-one;
20-ethyl-4,7β-dimethyl-4-aza-5α-pregn-17-en-3-one;
20-ethyl-4,7β-dimethyl-4-aza-5αpregnan-3-one;
7β,20-dimethyl-4-aza-5α-pregnan-3-one;
7β,20-dimethyl-4-aza-5αpregn-1-en-3-one;
20-ethyl-4,7β-dimethyl-4-aza-5α-pregnan-3-one;
20-propyl-4,7β-dimethyl-4-aza-5α-pregnan-3-one;
20-ethyl-4,7-dimethyl-4-aza-5α-pregn-1-en-3-one;
4,7β,20-trimethyl-4-aza-5α-pregn-1-en-3-one;
20-propyl-4,7-dimethyl-4-aza-5α-pregn-1-en-3-one;
20-ethyl-7β-methyl-4-aza-5α-pregn-1-en-3-one;
20-propyl-7β-methyl-4-aza-5α-pregnan-3-one;
20-propyl-7β-methyl-4-aza-5α-pregn-1-en-3-one;
17β-n-propyl-7β-methyl-4-aza-5α-androst-1-en-3-one;
17β-n-propyl-4,7β-dimethyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7-methyl-4-aza-5α-androst-1-en-3-one;
17β-n-butyl-4,7β-dimethyl-4-aza-5αandrost-1-en-3-one;
17β-isobutyl-4,7β-dimethyl-4-aza-5α-androst-1-en-3-one;
17β-tert.-butyl-4,7β-dimethyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
17β-(5-methylhexyl)-7β-methyl-4-aza-5α-androst-1-en-3-one;
17β-(5-methylhexyl)-4,7β-dimethyl-4-aza-5α-androst-1-en-3-one;
17β-n-propyl-7β-methyl-4-aza-5α-androstan-3-one;
17β-n-propyl-4,7β-dimethyl-4-aza-5α-androstan-3-one;
17β-n-butyl-7β-methyl-4-aza-5α-androstan-3-one;
17β-n-butyl-4,7β-dimethyl-4-aza-5α-androstan-3-one;
17β-(5-methylhexyl)-7β-methyl-4-aza-5α-androstan-3-one;
17β-(5-methylhexyl)-4,7β-dimethyl-4-aza-5α-androstan-3-one;
7β,20-dimethyl-4-aza-5α-pregn-17-en-3-one;
7β,20-dimethyl-4-aza-5α-pregn-1,17-dien-3-one;
20-ethyl-4,7β-dirnethyl-4-aza-5α-pregn-17-en-3-one;
20-ethyl-4,7β-dimethyl-4-aza-5α-pregnan-3-one;
7β,20-dimethyl -4-aza-5α-pregnan-3-one;
7β,20-dimethyl-4-aza-5α-pregn-1-en-3-one;
20-ethyl-4,7β-dimethyl-4-aza-5α-pregnan-3-one;
20-propyl-4,7β-dimethyl-4-aza-50α-pregnan-3-one;
17β-n-propyl-7β-methyl-4-aza-5α-androst-1-en-3-one;
17β-n-butyl-7β-methyl-4-aza-5α-androst-1-en-3-one;
17β-(5-methylhexyl)-7β-methyl-4-aza-5α-androst-1-en-3-one;
17β-n-propyl-7β-methyl-4-aza-5α-androstan-3-one;
17β-n-butyl-7β-methyl-4-aza-5α-androstan-3-one;
17β-(5-methylhexyl)-7β-methyl-4-aza-5α-androstan-3-one;
7β,20-dimethyl-4-aza-5α-pregn-1,17-dien-3-one;
7β,20-dimethyl-4-aza-5α-pregn-1-en-3-one;
20-ethyl-7β-methyl-4-aza-5α-pregn-1-en-3-one;
20-propyl-7β-methyl-4-aza-5α-pregn-1-en-3-one;
17β-n-propyl-7β-methyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
17β-(5-methylhexyl)-7β-methyl-4-aza-5α-androst-1-en-3-one;
7β,20-dimethyl-4-aza-5α-pregn-17-en-3-one;
7β,20-dimethy1-4-aza-5α-pregn-1,17-dien-3-one;
20-ethyl-4,7β-dimethyl-4-aza-5α-pregn-17-en-3-one;
20-ethyl-4,7β-dimethyl-4-aza-5α-pregnan-3-one;
7β,20-dimethyl-4-aza-5α-pregnan-3-one;
7β,20-dimethyl-4-aza-5α-pregn-1-en-3-one;
20-ethyl-4,7β-dimethyl-4-aza-5α-pregnan-3-one;
20-propyl-4,7β-dimethyl-4-aza-5α-pregnan-3-one;
20-ethyl-4,7β-dimethyl-4-aza-5α-pregn-1-en-3-one;
4,7β,20-trimethy1-4-aza-5α-pregn-1-en-3-one;
20-propyl-4,7β-dimethyl-4-aza-5α-pregn-1-en-3-one;
20-ethyl-7β-methyl-4-aza-5α-pregn-1-en-3-one;
20-propyl-7β-methyl-4-aza-5α-pregnan-3-one;
20-propyl-7β-methyl-4-aza-5α-pregn-1-en-3-one;
17β-n-propyl-7β-methyl-4-aza-5α-androst-1-en-3-one;
17β-n-propyl-4,7β-dimethyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-butyl-4,7β-dimethyl-4-aza-5α-androst-1-en-3-one;
17β-isobutyl-4,7β-dimethyl-4-aza-5α-androst-1-en-3-one;
17β-tert.-butyl-4,7β-dimethyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
17β-(5-methylhexyl)-7β-methyl-4-aza-5α-androst-1-en-3-one;
17β-(5-methythexyl)-4,7β-dimethyl-4-aza-5α-androst-1-en-3-one;
17β-n-propyl-7β-methyl-4-aza-5α-androstan-3-one;
17β-n-propyl-4,7β-dimethyl-4-aza-5α-androstan-3-one;
17β-n-butyl-7β-methyl-4-aza-5α-androstan-3-one;
17β-n-butyl-4,7β-dimethyl-4-aza-5α-androstan-3-one;
7β,20-dimethyl-4-aza-5α-pregn-1,17-dien-3-one;
7β,20-dimethyl-4-aza-5α-pregn-1-en-3-one;
20-ethyl-7β-methyl-4-aza-5α-pregn-1-en-3-one;
20-propyl-7β-methyl-4-aza-5α-pregn-1-en-3-one;
17β-n-propyl-7β-methyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-50α-androst-1-en-3-one;
17β-n-pentyl-7β-methyl-4-aza-5α-androst-1-en-3-one;
17β-isopentyl-7β-methyl-4-aza-5α-androst-1-en-3-one;
7β,20-dimethyl-4-aza-5α-pregn-1-en-3-one;
20-ethyl-7β-methyl-4-aza-5α-pregn-1-en-3-one;
20-propyl-7β-methyl-4-aza-5α-pregn-1-en-3-one;

17β-n-propyl-7β-methyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
20-(methoxymethyl)-4-methyl-5α-4-azapregnan-3-one;
17-(carbobenzyloxymethoxymethyl)-4-methyl-5α-4-azaandrostan-3-one;
5α-4-azaandrostan-3-on-17β-yloxy-N-(4-acetylphenyl) acetamide;
17α-thiophenoxy-4-methyl-5α-4-azaandrostan-3-one;
17-(methoxymethyl)-4-methyl-5α-4-azaandrostan-3-one;
17-(ethylthiomethyl)-4-methyl-5α-4-azaandrostan-3-one;
17-(carboxymethoxymethyl)-4-methyl -5α-4-azaandrostan-3-one;
17-(carboethoxymethoxymethyl)-4-methyl-5α-4-azaandrostan-3-one;
17-(carbobenzyloxymethoxymethyl)-4-methyl-5α-4-azaandrostan-3-one;
17-(diphenylmethoxymethyl)-4-methyl-5α-4-azaandrostan-3-one;
20-(diphenylmethoxy)-4-methyl-5α-4-azapregnan-3-one;
20-methoxy-4-methyl-5α-4-azapregnan-3-one;
20-(methoxymethyl)-4-methyl-5α-4-azapregnan-3-one;
20-(diphenylmethoxymethyl)-4-methyl-5α-4-azapregnan-3-one;
20-(ethylthiomethyl)-4-methyl-5α-4-azapregnan-3-one;
20-(isopropylthiomethyl)-4-methyl-5α-4-azapregnan-3-one; ethyl 4-methyl-5α-4-azaandrostan-3-on-17β-yloxyacetate;
diphenylmethyl 4-methyl-5α-4-azaandrostan-3-on-17β-yloxyacetate;
4-methyl-5α-4-azaandrostan-3-on-17β-yloxy-N-(3,4-dichlorobenzyl)acetamide;
4-methyl-5α-4-azaandrostan-3-on-17β-yloxy-N-phenylacetamide;
4-methyl-5α-4-azaandrostan-3-on-17β-yloxyacetic acid;
4-methyl-5α-4-azaandrostan-3-on-17β-yloxy-N-(4-acetylphenyl)acetamide;
4-methyl-5α-4-azaandrostan-3-on-17β-yloxyacetamide;
17β-(4-biphenyloxy)-4-methyl-5α-4-azaandrostan-3-one;
17β-(2,4-dinitrophenoxy)-4-methyl-5α-4-azaandrostan-3-one;
4-methyl-17α-phenoxy-5α-4-azaandrostan-3-one;
17α-(4-biphenyloxy)-4-methyl-5α-4-azaandrostan-3-one;
17β-diphenylmethoxy-4-methyl-5α-4-azaandrostan-3-one;
4-methyl-17α-thiophenoxy-5α-4-azaandrostan-3-one;
4-methyl-17α-phenylsulfonyl-5α-4-azaandrostan-3-one;
4-methyl-17α-phenylsulfinyl-5Oα-4-azaandrostan-3-one;
4-methyl-17β-(4-nitrophenoxy)-5α-4-azaandrostan-3-one;
17β-(4-aminophenoxy)-4-methyl-5α-4-azaandrostan-3-one hydrochloride;
17β-(4-acetamidophenoxy)-4-methyl-5α-4-azaandrostan-3-one;
17β-(4-cyanophenoxy)-4-methyl-5α-4-azaandrostan-3-one;
17β-(4-carboxamidophenoxy)-4-methyl-5α-4-azaandrostan-3-one;
17β-methyleneoxy-[N-cyclohexyl-N-(N-cyclohexylcarbamoyl)-carbamoyl]-4-methyl-5α-4-azaandrostan-3-one;
4-methyl-17β-(3-pyridyl)oxy-5α-4-azaandrostan-3-one;
4-methyl-i 17β-(2-pyridyl)methoxy-5α-4-azaandrostan-3-one;
17β-benzyloxy-4-methyl-5α-4-azaandrostan-3-one; ethyl 5α-4-azaandrostan-3-on-17β-yloxyacetate;
5α-4-azaandrostan-3-on-17β-yloxyacetic acid;

5α-4-azaandrostan-3-on-17β-yloxy-N-phenylacetamide;
5α-4-azaandrostan-3-on-17β-yloxy-N-(4-acetylphenyl) acetamide, diphenylmethyl 5α-4-azaandrostan-3-on-17β-yloxyacetate;
17β-methyleneoxy-[N-cyclohexyl-N-(N-cyclohexylcarbamoyl)-carbamoyl]-5α-4-azaandrostan-3-one;
5α-4-azaandrostan-3-on-17β-yloxy-N-[4-(1(RS)-hydroxyethyl)-phenyl]acetamide;
5α-4-azaandrostan-3-on-17β-yloxy-N-(4-t-butylphenyl) acetamide;
17β-methyleneoxy-[N-isopropyl-N-(N-isopropylcarbamoyl)-carbamoyl]-5α-4-azaandrostan-3-one;
17-(4-methylpentyloxy)-4-methyl-5α-4-azaandrostan-3-one;
17-hexyloxy-4-methyl-5α-4-azaandrostan-3-one;
4-methyl-17-propyloxy-5α-4-azaandrostan-3-one;
4-methyl-17-undecyloxy-5α-4-azaandrostan-3-one;
17-allyloxy-4-methyl-5α-4-azaandrostan-3-one;
17-allyloxy-4-methyl-4-azaandrost-5-en-3-one;
17-hexyloxy-4-methyl-4-azaandrost-5-en-3-one;
17-(4-(isobutyl)benzyloxy)methyl-4-methyl-5α-4-azaandrostan-3-one;
17-(4-acetamidobenzyloxy)methyl-4-methyl-5α-4-azaandrostan-3-one;
4-methyl-17-(3-nitrobenzyloxy)methyl-5α-4-azaandrostan-3-one;
4-methyl-17-(phenoxyethoxymethyl)-5α-4-azaandrostan-3-one;
17-(3-(isopropylthio)propyloxy)methyl-4-methyl-5α-4-azaandrostan-3-one;
17-(2-fluorobenzyloxy)methyl-4-methyl-5α-4-azaandrostan-3-one;
4-methyl-17-(3-(trifluoromethyl)benzyloxy)methyl-5α-4-azaandrostan-3-one;
17-(4-dimethylaminobenzyloxy)methyl-4-methyl-5α-4-azaandrostan-3-one;
17-((N-t-butyl-carboxamido)methoxymethyl)-4-methyl-5α-4-azaandrostan-3-one;
20-(3-(ethylthio)propyl)-4-methyl-5α-4-azapregnan-3-one;
20-(2-(benzyloxy)ethyl)-4-methyl-5α-4-azapregnan-3-one;
20-(3-methoxybenzyloxy)methyl-4-methyl-5α-4-azapregnan-3-one;
17α-(carboethoxymethoxy)benzyl-4-methyl-5α-4-azaandrostan-3-one;
20-(4-(methylthio)benzyloxy)methyl-4-methyl-5α-4-azapregnan-3-one;
4-methyl-17-n-octylthiomethyl-5α-4-azaandrostan-3-one;
20-(t-butylthiomethyl)-4-methyl-5α-4-azapregnan-3-one;
17-(2-furfuryl)thiomethyl-4-methyl-5α-4-azaandrostan-3-one;
17-(geranyloxymethyl)-4-methyl-5α-4-azaandrostan-3-one;
4-methyl-20-(2-(n-nonylthio)ethyl)-5α-4-azapregnan-3-one;
20-(methylthiomethyl)-4-methyl-5α-4-azapregnan-3-one;
17-(4-(benzyloxy)benzyloxy)methyl-4-methyl-5α-4-azaandrostan-3-one;
20-(diphenylmethylthio)methyl-4-methyl-5α-4-azapregnan-3-one;
17-(3-(ethylthio)propyl)-4-methyl-5α-4-azaandrostan-3-one;
4-methyl-20-(phenylthiomethyl)-5α-4-azapregnan-3-one;
17-(ethylsulfonylmethyl)-4-methyl-5α-4-azaandrostan-3-one;
17-(4-ethoxybenzyloxy)methyl-4-methyl-5α-4-azaandrostan-3-one;
4,7β-dimehtyl-4-aza-5α-cholestan-3-one;

and pharmaceutically acceptable salts thereof.

4. The method of treating preterm labor according to claim 3 wherein the inhibitor of 5α-reductase type 1 is selected from:
- 3-oxo-4-aza-4,7β-dimethyl-16β-(4-chlorophenoxy)-5α-androstane,
- 3-oxo-4-aza-4,7β-dimethyl-16β-(phenoxy)-5α-androstane,
- 3-oxo-4-aza-7-methyl-16β-(4-methylphenoxy)-5αandrost-1-ene, 4,7β-dimethyl-4-aza-5α-cholestan-3-one, and 7β,20-dimethyl-4-aza-5α-pregn-1-en-3-one;

or pharmaceutically acceptable salts thereof.

5. The method of treating preterm labor of claim 1 wherein the inhibitor of 5α-reductase type 1 is a dual inhibitor of 5α-reductase type 1 and 5α-reductase type 2.

6. The method of treating preterm labor according to claim 5 wherein the inhibitor is selected from: those of structural formula IX:

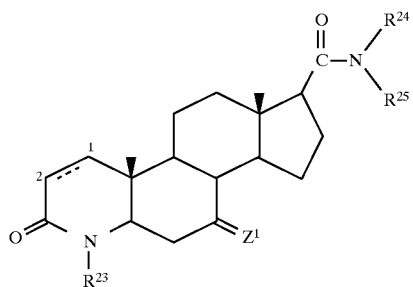

or a pharmaceutically acceptable salt or ester thereof, wherein: the $C_1$–$C_2$ bond designated "---" represents a single or double bond;

$R^{23}$ is selected from:
  (1) —H,
  (2) —CH$_3$ and
  (3) —CH$_2$CH$_3$;

$Z^1$ is selected from:
  (1) oxo,
  (2) α-H and a β-substituent selected from:
    (a) $C_{1-4}$ alkyl,
    (b) $C_{2-4}$ alkenyl,
    (c) —CH$_2$ COOH,
    (d) —OH,
    (e) —COOH,
    (f) —COO ($C_{1-4}$ alkyl),
    (g) —OCONR$^{26}$R$^{27}$ wherein
      $R^{26}$ and $R^{27}$ are independently selected from
        (i) —H,
        (ii) —C$_{1-4}$ alkyl,
        (iii) phenyl and
        (iv) benzyl;
      or $R^{26}$ and $R^{27}$ taken together with the nitrogen to which they are attached represent a 5–6 membered saturated heterocycle optionally containing one other heteroatom selected from —O—, —NH— and —S—;
    (h) $C_{1-4}$ alkoxy,
    (i) $C_{3-6}$ cycloalkoxy,
    (j) —OC(O)R$^{28}$, wherein $R^{28}$ is $C_{1-6}$ alkyl or phenyl,
    (k) halo,
    (l) halo-$C_{1-2}$ alkyl,
    (m) —CF$_3$, and
    (n) $C_{3-6}$ cycloalkyl;
  (3) =CHR$^{29}$;
  (4) spirocyclopropane either unsubstituted or substituted with $R^{29}$;

$R^{24}$ is selected from —H and $C_{1-6}$ alkyl, either unsubstituted or substituted with one or more of aryl, heteroaryl, —COOH or —OH;

$R^{25}$ is —$C_{1-6}$ alkyl substituted with one or more of aryl, heteroaryl, —COOH, —OH or di-aryl amino; and $R^{29}$ is selected from —H and $C_{1-4}$ alkyl.

7. The method of treating pretermn labor according to claim 5 wherein the inhibitor is selected from:
- 17β-N-(2,5-bis(trifluoromethyl))phenyl carbamoyl-4-aza-5Oα-androst-1-en-3-one;
- N-(diphenylmethyl)-3-oxo-4-aza-7β-methyl-5α-androstane-17β-carboxamide;
- N-(diphenylmethyl)-3-oxo-4-aza-7β-methyl-5α-androst-1-ene-17β-carboxamide;
- N-(diphenylmethyl)-3-oxo-4-aza-4,7β-dimethyl-5α-androstane-17β-carboxamide; and
- N-(methyl)-N-(diphenylmethyl)-3-oxo-4-aza-4,7β-dimethyl-5α-androstane-17β-carboxamide.

8. The method of treating preterm labor according to claim 1 wherein the mammal is a female human.

9. A method of preventing premature labor in a mammalian subject susceptible thereto comprising administration of a labor-preventive amount of an inhibitor of 5α-reductase type 1 to the subject.

10. The method of preventing premature labor according to claim 9 wherein the inhibitor of 5α-reductase type 1 is selected from:
(I) a compound of structural formula (I):

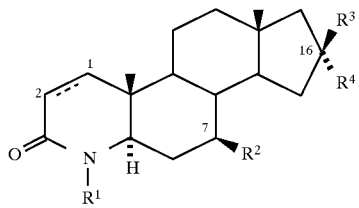

or a pharmaceutically acceptable salt or ester thereof wherein:

the $C_1$–$C_2$ carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)NR$_b$R$_c$, where R$_b$ and R$_c$ are independently H, $C_{1-6}$ alkyl, aryl, or aryl $C_{1-6}$ alkyl; wherein the alkyl moiety can be substituted with 1–3 of: halo; $C_{1-4}$ alkoxy; or trifluoromethyl; and the aryl moiety can be substituted with 1–3 of: halo; $C_{1-4}$ alkyl; $C_{1-4}$ alkoxy; or trifluoromethyl;
(g) $C_{1-10}$ alkyl-X—;
(h) $C_{2-10}$ alkenyl-X—;
wherein the $C_{1-10}$ alkyl in (g) and $C_{2-10}$ alkenyl in (h) can be unsubstituted or substituted with one to three of:
(i) halo; hydroxy; cyano; nitro; mono-, di- or trihalomethyl; oxo; hydroxysulfonyl; carboxy;

(ii) hydroxy $C_{1-6}$ alkyl; $C_{1-6}$alkyloxy; $C_{1-6}$ alkylthio; $C_{1-6}$ alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;

(iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;

(iv) —C(O)NR$_b$R$_c$; —N(R$_b$)—C(O)—R$_c$; —NR$_b$R$_c$; where R$_b$ and R$_c$ are defined above;

(i) aryl-X—;

(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

wherein the aryl in (i) and heteroaryl in (j) can be unsubstituted or substituted with one to three of:

(v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

(vi) $C_{1-6}$ alkyl; hydroxy $C_{1-6}$ alkyl; $C_{1-6}$ alkyloxy; $C_{1-6}$ alkyloxy $C_{1-6}$ alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$ alkyl; R$_b$R$_c$N—C(O)—$C_{1-6}$ alkyl; $C_{1-6}$ alkanoylarnino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;

(vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$ alkyl; $C_{1-4}$alkoxy; or trifluoromethyl;

(viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is $C_{1-6}$ alkyl or aryl, in which the alkyl moiety can be substituted with 1–3 of: halo; $C_{1-4}$ alkoxy; or trifluoromethyl, and the aryl moiety can be substituted with 1–3 of: halo; $C_{1-4}$ alkyl; $C_{1-4}$ alkoxy, or trifluoromethyl; —N(R$_b$)—C(O) NR$_c$Rd, wherein R$_d$ is selected from H, $C_{1-6}$ alkyl, and aryl; in which said $C_{1-6}$ alkyl and aryl can be substituted as described above in (f) for R$_b$ and R$_c$;

(ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) R$^3$ and R$^4$ taken together can be carbonyl oxygen;

(l) R$^3$ and R$^4$ taken together can be =CH—R$_g$, wherein R$_g$ is defined in (viii); and wherein:

X is selected from the group consisting of:
—O—; —S(O)$_n$—; —C(O)—; —CH(R$_e$)—;
—C(O)—O—*; —C(O)—N(R$_e$)—*; —N(R$_e$)
—C(O)—O—*; —O—C(O)—N(R$_e$)—*;
—N(R$_e$)C(O)—N(R$_e$)—; —O—CH(R$_e$)—*;
—N(R$_e$)—; wherein R$_e$ is H, $C_{1-3}$ alkyl, aryl, aryl- $C_{1-3}$ alkyl, or unsubstituted or substituted heteroaryl, as defined above in (j);

wherein the asterisk (*) denotes the bond which is attached to the 16-position in Structure I; and n is zero, 1 or 2;

(II) a compound of structural formula (II):

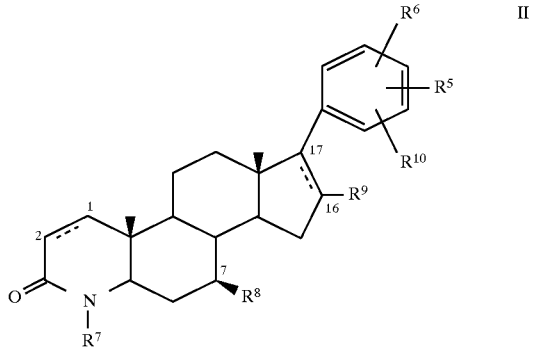

or a pharmaceutically acceptable salt or ester thereof, wherein: the C1–C2 bond and the C16–C17 bond designated "---" each independently represent a single or double bond;

R$^7$ and R$^8$ are independently selected from:
(1) —H,
(2) —CH$_3$ and
(3) —CH$_2$CH$_3$;

R$^9$ is selected from:
(1) —H and
(2) —CH$_3$; and R$^9$ is β-oriented if C16–C17 is saturated;

R$^{10}$, R$^5$ and R$^6$ are independently selected from:
(1) —H,
(2) —$C_{1-8}$ alkyl, unsubstituted or substituted with —OH,
(3) —$C_{1-3}$ perfluoroalkyl,
(4) -halo,
(5) —OR$^1$, wherein R$^{11}$ is
   (a) —H,
   (b) —C1-8 alkyl,
   (c) —$C_{1-6}$ alkylcarbonyl,
   (d) —$C_{1-6}$ alkylsulfonyl, or
   (e) —$C_{1-6}$ alkoxycarbonyl,
(6) —NHR$^{11}$,
(7) —NO$_2$,
(8) —S($C_{1-6}$ alkylcarbonyl),
(9) —S(O)$_n$$C_{1-8}$ alkyl, wherein n is 0, 1 or 2,
(10) —CO$_2$R$^{12}$ wherein R$^{12}$ is
   a) —H or
   b) —$C_{1-8}$ alkyl,
(11) —C(O)R$^{12}$,
(12) —C(O)N(R$^{12}$)$_2$,
(13) —CN,
(14) —C(R$^{12}$)$_2$OR$^{11}$,
(15) —C(R$^{12}$)$_2$NR$^{11}$,
(16) —C(R$^{12}$)$_2$S($C_{1-8}$ alkyl),
(17) —C(R$^{12}$)$_2$S($C_{1-6}$ alkylcarbonyl), and
(18) phenyl, unsubstituted or having 1 to 3 substituents selected from:
   (a) —OH, (b) halo,
(c) $C_{1-3}$ alkyl, and
(d) $C_{1-3}$ alkoxy; or
$R^{10}$ and $R^5$ or $R^5$ and $R^6$, on vicinal carbon atoms, may be joined to form with the phenyl to which they are attached a naphthyl or indanyl group; and the 17-position substituent is β-oriented if C16–C17 is saturated;

(III) a compound of structural formula VII:

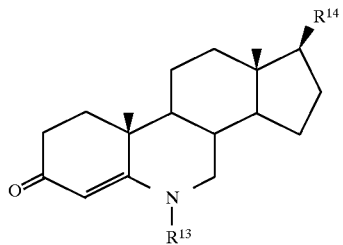

or a pharmaceutically acceptable salt or ester thereof, wherein:

$R^{13}$ is selected from —H, —$CH_3$ and —$CH_2CH_3$;
$R^{14}$ is selected from:
(1) —H, —OH, —$NH_2$, or =O,
(2) —$C_{1-12}$ alkyl,
(3) —$C_{1-12}$ alkyl-phenyl,
(4) —O—$C_{1-12}$ alkyl or —S(O)$_n$—$C_{1-12}$ alkyl,
(5) —O-Het or —S(O)n-Het,
(6) —O-phenyl or —S(O)$_n$-phenyl,
(7) —$C_{1-6}$ alkyl-X-$C_{1-12}$ alkyl,
(8) —$C_{1-6}$ alkyl-X-Het,
(9) —C(O)-phenyl,
(10) —X—C(O)—$C_{1-12}$ alkyl,
(11) —OC(O)—NH$C_{1-12}$ alkyl,
(12) —OC(O)—NH-phenyl,
(13) —CN, and
(14) —NR$^{15}$R$^{16}$, wherein $R^{15}$ and $R^{16}$ are each independently selected from —H, $C_{1-12}$ alkyl, phenyl and Het;

Het is selected from piperidinyl, piperizinyl, pyrrolidinyl, pyrrolyl, furanyl and thienyl;
X is selected from the group consisting of O, NH and S(O)$_n$; and n is zero, 1 or 2;

(IV) a compound of structural formula (VIII):

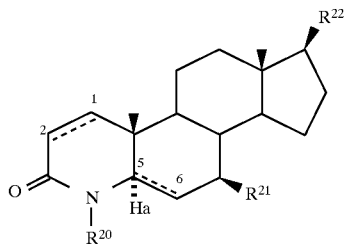

wherein:
the C1–C2 and C5–C6 bonds designated with a dotted line each independently represent a single or double bond, provided that when the C5–C6 is a double bond, $H_a$ is absent and when the C5–C6 bond is a single bond $H_a$ is present and represents hydrogen;
$R^{20}$ is selected from hydrogen and $C_{1-5}$ alkyl;
$R^{21}$ is $C_{1-5}$ alkyl, either straight or branched chain; and
$R^{22}$ is $C_{3-7}$ alkyl, either straight or branched chain, optionally having one degree of unsaturation;

(V) a compound of structural formula (XI):

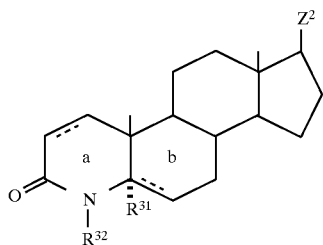

wherein "a" and "b" are both single bonds and $R^{31}$ is hydrogen, or
"a" is a double bond, "b" is a single bond and $R^{31}$ is hydrogen, or
"a" is a single bond, "b" is a double bond and $R^{31}$ is absent;

$Z^2$ is —XR$^{33}$, or —(CHR$^{30}$)$_n$—XR$^{33}$;
n is an integer selected from 1–10;
X is —O— or —S(O)$_p$—,
wherein p is zero, 1 or 2;
$R^{30}$ is —H, aryl, or —$C_{1-3}$ alkyl unsubstituted or substituted with aryl and when n is greater than 1, $R^{30}$ can be the same or different at each occurrence;
$R^{32}$ is —H, methyl, ethyl, —OH, —$NH_2$ or —$SCH_3$;
$R^{33}$ is (1) —$C_{1-20}$ alkyl, unsubstituted or substituted with one or more of:
(a) —OH,
(b) halo,
(c) —$C_{1-8}$ alkoxy,
(d) —$C_{1-10}$ alkenyl,
(e) —CONR$^{34}$R$^{34}$, wherein $R^{34}$ is independently
(i) —H,
(ii) —$C_{1-8}$ alkyl unsubstituted or substituted with one or more of $R^{36}$, aryl or heterocycle, the aryl being unsubstituted or substituted with one or more of $R^{36}$ or $R^{38}$,
(iii) aryl unsubstituted or substituted with one or more of $R^{36}$ or $R^{38}$, or
(iv) heterocycle, unsubstituted or substituted with one or more of $R^{36}$ or $R^{38}$,
(f) —COOR$^{35}$, wherein $R^{35}$ is
(i) —H,
(ii) —$C_{1-8}$ alkyl unsubstituted or substituted with one or more of $R^{36}$ or aryl, the aryl being unsubstituted or substituted with one or more of $R^{36}$ or $R^{38}$, or
(iii) aryl, unsubstituted or substituted with one or more of $R^{36}$ or $R^{38}$,
(g) —S(O)$_p$—R$^{35}$, wherein p is defined above,
(h) —N(R$^{34}$)$_2$,
(i) aryl, unsubstituted or substituted with one or more of aryl, $R^{36}$ or $R^{38}$,
(j) heterocycle, unsubstituted or substituted with one or more of $R^{36}$ or $R^{38}$,
(k) —$C_{3-10}$ cycloalkyl, such as cyclohexyl, norbornyl, or adamantyl, unsubstituted or substituted with one or more of $R^{36}$ or $R^{38}$, or
(1) —CONR$^{37}$—CO—NHR$^{37}$, wherein $R^{37}$ is —H, —$C_{1-8}$ alkyl, benzyl or cyclohexyl,
(2) aryl, unsubstituted or substituted with one or more of aryl, $R^{36}$ or $R^{38}$, or
(3) heterocycle or —$C_{3-10}$ cycloalkyl, either of which is unsubstituted or substituted with one or more of $R^{36}$ or $R^{38}$;

$R^{36}$ is (1) —OH,
(2) —$C_{1-3}$ alkoxy,
(3) —CN,
(4) —COOR$^{35}$
(5) —$C_{1-8}$ alkyl-COOR$^{35}$,
(6) —NO$_2$, or
(7) -halo; and
(8) amino, mono-$C_1$–$C_4$ alkylamino, di-$C_1$–$C_4$-alkylamino;

$R^{38}$ is (1) —$C_{1-8}$ alkyl, unsubstituted or substituted with one or more of aryl or $R^{36}$,
(2) —CO—A, —$C_{1-8}$ alkyl-CO—A, —NHCO—A, or—S(O)$_p$—A, wherein p is defined above and A is
(a) —H,
(b) —$C_{1-8}$ alkyl, unsubstituted or substituted with one or more of
(i) —$R^{36}$, or
(ii) aryl, unsubstituted or substituted with one or more of $R^{36}$, or
(c) aryl, unsubstituted or substituted with one or more of $R^{36}$,
(3) —NHCO-heterocycle,
(4) —N(R$^{39}$)$_2$ or —CON(R$^{39}$)$_2$ wherein $R^{39}$ is independently heterocycle, or —A,
(5) —NHCO—(CH$_2$)$_q$—CO—Q$^1$, wherein q is 1–4, and Q$^1$ is —N(R$^{39}$)$_2$ or —OR$^{39}$;
with the proviso that when Z is —OR$^{33}$, R$^{32}$ is —H, a is a single bond and b is a single or double bond, $R^4$ is not isopentyl; and
4,7β-dimethyl-4-aza-5α-cholestan-3-one;
or a pharmaceutically acceptable salt, ester, or stereoisomer thereof.

11. The method of preventing premature labor according to claim 9 wherein the 5α-reductase type 1 inhibitor is selected from:
4-aza-4,7β-dimethyl-5α-androstane-3,16-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16-(n-propyloxy)-5α-androstane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16-(phenoxy)-5α-androst-1-ene;
3-oxo-4-aza-4-methyl-16ox-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16,-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5-androst-1-ene;
3-oxo-4-aza-4,7β-dimethyl-16-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-50α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-50α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16c-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-50c-androstane;
3-oxo-4-aza-4,7β-dimethyl-16β-(2-pyrinidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-50α-androstane;
3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16β-(4-chlorobenzylidene)-50α-androstane;
3-oxo-4-aza-4,7β-dimethyl-16β-benzylidene-5α-androstane;
3-oxo-4-aza-4,7β-dimethyl-16β-(4-methylbenzylidene)-50α-androstane;
3-oxo-4-aza-4,7β-dimethyl-16β-(4-chlorobenzyl)-5α-androstane;
3-oxo-4-aza-4,7β-dimethyl-16β-(4-methylbenzyl)-5α-androstane;
3-oxo-4-aza-4,7β-dimethyl-16β-(3-pyridylmethyl)-5α-androstane;
3-oxo-4-aza-4,7β-dimethyl-16β-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
6-methyl-6-aza-androst-4-en-3,17-dione;
6-methyl-17-propyl-6-aza-androst-4-en-3-one;
6-methyl-6-aza-androst-4-en-3-one;
6-methyl-17-hydroxy-6-aza-androst-4-en-3-one;
6-methyl-17-t-butylcarbamoyloxy-6-aza-androst-4-en-3-one;
6-aza-cholest-4-en-3-one;
6-methyl-6-aza-cholest-4-en-3-one;
7β,20-dimethyl-4-aza-5α-pregn-17-en-3-one;
7β,20-dimethyl-4-aza-5α-pregn-1,17-dien-3-one;
20-ethyl-4,7-dimethyl-4-aza-5α-pregn-17-en-3-one;
20-ethyl-4,7β-dimethyl-4-aza-5α-pregnan-3-one;
7β,20-dimethyl-4-aza-5α-pregnan-3-one;
7β,20-dimethyl-4-aza-5α-pregn-1-en-3-one;
20-ethyl-4,7β-dimethyl-4-aza-5α-pregnan-3-one;
20-propyl-4,7β-dimethyl-4-aza-5α-pregnan-3-one;
20-ethyl-4,7β-dimethyl-4-aza-5α-pregn-1-en-3-one;
4,7β,20-trimethyl-4-aza-5α-pregn-1-en-3-one;
20-propyl-4,7β-dimethyl-4-aza-5α-pregn-1-en-3-one;
20-ethyl-7β-methyl-4-aza-5α-pregn-1-en-3-one;
20-propyl-7β-methyl-4-aza-5α-pregnan-3-one;
20-propyl-7β-methyl-4-aza-5α-pregn-1-en-3-one;
17β-n-propyl-7β-methyl-4-aza-5α-androst-1-en-3-one;
17β-n-propyl-4,7β-dimethyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-butyl-4,7β-dimethyl-4-aza-5α-androst-1-en-3-one;
17β-isobutyl-4,7β-dimethyl-4-aza-5α-androst-1-en-3-one;
17β-tert.-butyl-4,7β-dimethyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
17β-(5-methylhexyl)-7β-methyl-4-aza-5α-androst-1-en-3-one;
17β-(5-methylhexyl)-4,7β-dimethyl-4-aza-5α-androst-1-en-3-one;
17β-n-propyl-7β-methyl-4-aza-5α-androstan-3-one;
17β-n-propyl-4,7β-dimethyl-4-aza-5α-androstan-3-one;
17β-n-butyl-7β-methyl-4-aza-5α-androstan-3-one;
17β-n-butyl-4,7β-dimethyl-4-aza-5α-androstan-3-one;
17β-(5-methylhexyl)-7β-methyl-4-aza-5α-androstan-3-one;
17β-(5-methylhexyl)-4,7β-dimethyl-4-aza-5α-androstan-3-one;
7β,20-dimethyl-4-aza-5α-pregn-17-en-3-one;
7β,20-dimethyl-4-aza-5α-pregn-1,17-dien-3-one;
20-ethyl-4,7β-dimethyl-4-aza-50α-pregn-17-en-3-one;
20-ethyl-4,7β-dimethyl-4-aza-5α-pregnan-3-one;

7β,20-dimethyl-4-aza-5α-pregnan-3-one;
7β,20-dimethyl-4-aza-5α-pregn-1-en-3-one;
20-ethyl-4,7β-dimethyl-4-aza-5α-pregnan-3-one;
20-propyl-4,7β-dimethyl-4-aza-5α-pregnan-3-one;
17β-n-propyl-7β-methyl-4-aza-5α-androst-1-en-3-one;
17β-n-butyl-7β-methyl-4-aza-5α-androst-1-en-3-one;
17β-(5-methythexyl)-7β-methyl-4-aza-5α-androst-1-en-3-one;
17β-n-propyl-7β-methyl-4-aza-5α-androstan-3-one;
17β-n-butyl-7β-methyl-4-aza-5α-androstan-3-one;
17β-(5-methylhexyl)-7β-methyl-4-aza-5α-androstan-3-one;
7β,20-dimethyl-4-aza-5α-pregn-1,17-dien-3-one;
7β,20-dimethyl-4-aza-5α-pregn- -en-3-one;
20-ethyl-7β-methyl-4-aza-5α-pregn-1-en-3-one;
20-propyl-7β-methyl-4-aza-5α-pregn-1-en-3-one;
17β-n-propyl-7β-methyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
17β-(5-methythexyl)-7β-methyl-4-aza-50c-androst-1-en-3-one;
7β,20-dimethyl-4-aza-50α-pregn-17-en-3-one;
7β,20-dimethyl-4-aza-5α-pregn-1,17-dien-3-one;
20-ethyl-4,7β-dimethyl-4-aza-5α-pregn-17-en-3-one;
20-ethyl-4,7β-dimethyl-4-aza-5α-pregnan-3-one;
7β,20-dimethyl-4-aza-5α-pregnan-3-one;
7β,20-dimethyl-4-aza-5α-pregn-1-en-3-one;
20-ethyl-4,7β-dimethyl-4-aza-5α-pregnan-3-one;
20-propyl-4,7β-dimethyl-4-aza-5α-pregnan-3-one;
20-ethyl-4,7β-dimethyl-4-aza-5α-pregn-1-en-3-one;
4,7β,20-trimethyl-4-aza-5α-pregn-1-en-3-one;
20-propyl-4,7β-dimethyl-4-aza-5α-pregn-1-en-3-one;
20-ethyl-7β-methyl-4-aza-5α-pregn-1-en-3-one;
20-propyl-7β-methyl-4-aza-5α-pregnan-3-one;
20-propyl-7β-methyl-4-aza-5α-pregn-1-en-3-one;
17β-n-propyl-7β-methyl-4-aza-5α-androst-1-en-3-one;
17β-n-propyl-4,7β-dimethyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-butyl-4,7β-dimethyl-4-aza-5α-androst-1-en-3-one;
17β-isobutyl-4,7β-dimethyl-4-aza-5α-androst-1-en-3-one;
17β-tert.-butyl-4,7β-dimethyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
17β-(5-methylhexyl)-7β-methyl-4-aza-5α-androst-1-en-3-one;
17β-(5-methylhexyl)-4,7β-dimethyl-4-aza-5α-androst-1-en-3-one;
17β-n-propyl-7β-methyl-4-aza-5α-androstan-3-one;
17β-n-propyl-4,7β-dimethyl-4-aza-5α-androstan-3-one;
17β-n-butyl-7β-methyl-4-aza-5α-androstan-3-one;
17β-n-butyl-4,7β-dimethyl-4-aza-5α-androstan-3-one;
7β,20-dimethyl-4-aza-50α-pregn-1,17-dien-3-one;
7β,20-dimethyl-4-aza-5α-pregn-1-en-3-one;
20-ethyl-7β-methyl-4-aza-5α-pregn-1-en-3-one;
20-propyl-7β-methyl-4-aza-5α-pregn-1-en-3-one;
17β-n-propyl-7β-methyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
7β,20-dimethyl-4-aza-5α-pregn-1-en-3-one;
20-ethyl-7β-methyl-4-aza-5α-pregn-1-en-3-one;
20-propyl-7β-methyl-4-aza-5α-pregn-1-en-3-one;
17β-n-propyl-7β-methyl-4-aza-5α-androst-1-en-3-one;
17β-n-butyl-7β-methyl-4-aza-5α-androst-1-en-3-one;
17β-isobutyl-7β-methyl-4-aza-5α-androst-1-en-3-one;
17β-tert.-butyl-7β-methyl-4-aza-5α-androst-1-en-3-one;
17β-n-pentyl-7β-methyl-4-aza-5α-androst-1-en-3-one;
17β-isopentyl-7β-methyl-4-aza-5α-androst-1-en-3-one;
20-(methoxymethyl)-4-methyl-5α-4-azapregnan-3-one;
17-(carbobenzyloxymethoxymethyl)-4-methyl-5α-4-azaandrostan-3-one;
5α-4-azaandrostan-3-on-17β-yloxy-N-(4-acetylphenyl)acetamide;
17α-thiophenoxy-4-methyl-5α-4-azaandrostan-3-one;
17-(methoxymethyl)-4-methyl-5α-4-azaandrostan-3-one;
17-(ethylthiomethyl)-4-methyl-5α-4-azaandrostan-3-one;
17-(carboxymethoxymethyl)-4-methyl-5α-4-azaandrostan-3-one;
17-(carboethoxymethoxymethyl)-4-methyl-5α-4-azaandrostan-3-one;
17-(carbobenzyloxymethoxymethyl)-4-methyl-5α-4-azaandrostan-3-one;
17-(diphenylmethoxymethyl)-4-methyl-5α-4-azaandrostan-3-one;
20-(diphenylmethoxy)-4-methyl-5α-4-azapregnan-3-one;
20-methoxy-4-methyl-5α-4-azapregnan-3-one;
20-(methoxymethyl)-4-methyl-5α-4-azapregnan-3-one;
20-(diphenylmethoxymethyl)-4-methyl-5α-4-azapregnan-3-one;
20-(ethylthiomethyl)-4-methyl-5α-4-azapregnan-3-one;
20-(isopropylthiomethyl)-4-methyl -5α-4-azapregnan-3-one; ethyl 4-methyl-5α-4-azaandrostan-3-on-17β-yloxyacetate; diphenylmethyl 4-methyl-5α-4-azaandrostan-3-on-17β-yloxyacetate;
4-methyl-5α-4-azaandrostan-3-on-17β-yloxy-N-(3,4-dichlorobenzyl)acetamide;
4-methyl-5α-4-azaandrostan-3-on-17β-yloxy-N-phenylacetamide;
4-methyl-5α-4-azaandrostan-3-on-17β-yloxyacetic acid;
4-methyl-5α-4-azaandrostan-3-on-17β-yloxy-N-(4-acetylphenyl)acetamide;
4-methyl-5α-4-azaandrostan-3-on-17β-yloxyacetamide;
7β-(4-biphenyloxy)-4-methyl-5α-4-azaandrostan-3-one;
7β-(2,4-dinitrophenoxy)-4-methyl-5α-4-azaandrostan-3-one;
4-methyl-17α-phenoxy-5α-4-azaandrostan-3-one;
17α-(4-biphenyloxy)-4-methyl-5α-4-azaandrostan-3-one;
17β-diphenylmethoxy-4-methyl-5α-4-azaandrostan-3-one;
4-methyl-17α-thiophenoxy-5α-4-azaandrostan-3-one;
4-methyl-17α-phenylsulfonyl-5α-4-azaandrostan-3-one;
4-methyl-17α-phenylsulfinyl-5α-4-azaandrostan-3-one;
4-methyl-17β-(4-nitrophenoxy)-5α-4-azaandrostan-3-one;
17β-(4-aminophenoxy)-4-methyl-5α-4-azaandrostan-3-one hydrochloride;
17β-(4-acetamidophenoxy)-4-methyl-5α-4-azaandrostan-3-one;
17β-(4-cyanophenoxy)-4-methyl-5α-4-azaandrostan-3-one;
17β-(4-carboxamidophenoxy)-4-methyl-5α-4-azaandrostan-3-one;
17β-methyleneoxy-[N-cyclohexyl-N-(N-cyclohexylcarbamoyl)-carbamoyl]-4-methyl-5α-4-azaandrostan-3-one;
4-methyl-17β-(3-pyridyl)oxy-5α-4-azaandrostan-3-one;
4-methyl-17β-(2-pyridyl)methoxy-5α-4-azaandrostan-3-one;
17β-benzyloxy-4-methyl-5α-4-azaandrostan-3-one; ethyl 5α-4-azaandrostan-3-on-17β-yloxyacetate;

5α-4-azaandrostan-3-on-17β-yloxyacetic acid;
5α-4-azaandrostan-3-on-17β-yloxy-N-phenylacetamide;
5α-4-azaandrostan-3-on-17β-yloxy-N-(4-acetylphenyl) acetamide, diphenylmethyl 5α-4-azaandrostan-3-on-17β-yloxyacetate;
17β-methyleneoxy-[N-cyclohexyl-N-(N-cyclohexylcarbamoyl)-carbamoyl]-5α-4-azaandrostan-3-one;
5α-4-azaandrostan-3-on-17β-yloxy-N-[4-(1(RS)-hydroxyethyl)-phenyl]acetamide;
5α-4-azaandrostan-3-on-17β-yloxy-N-(4-t-butylphenyl) acetamide;
17β-methyleneoxy-[N-isopropyl-N-(N-isopropylcarbamoyl)-carbamoyl]-5α-4-azaandrostan-3-one;
17β-(4-methylpentyloxy)-4-methyl-5α-4-azaandrostan-3-one;
17-hexyloxy-4-methyl-5α-4-azaandrostan-3-one;
4-methyl-17-propyloxy-5α-4-azaandrostan-3-one;
4-methyl-17-undecyloxy-5α-4-azaandrostan-3-one;
17-allyloxy-4-methyl-5α-4-azaandrostan-3-one;
17-allyloxy-4-methyl-4-azaandrost-5-en-3-one;
17-hexyloxy-4-methyl-4-azaandrost-5-en-3-one;
17-(4-(isobutyl)benzyloxy)methyl-4-methyl-5α-4-azaandrostan-3-one;
17-(4-acetamidobenzyloxy)methyl-4-methyl-5α-4-azaandrostan-3-one;
4-methyl-17-(3-nitrobenzyloxy)methyl-5α-4-azaandrostan-3-one;
4-methyl-17-(phenoxyethoxymethyl)-5α-4-azaandrostan-3-one;
17-(3-(isopropylthio)propyloxy)methyl-4-methyl-5α-4-azaandrostan-3-one;
17-(2-fluorobenzyloxy)methyl-4-methyl-5α-4-azaandrostan-3-one;
4-methyl-17-(3-(trifluoromethyl)benzyloxy)methyl-5α-4-azaandrostan-3-one;
17-(4-dimethylaminobenzyloxy)methyl-4-methyl-5α-4-azaandrostan-3-one;
17-((N-t-butyl-carboxamido)methoxymethyl)-4-methyl-5α-4-azaandrostan-3-one;
20-(3-(ethylthio)propyl)-4-methyl-5α-4-azapregnan-3-one;
20-(2-(benzyloxy)ethyl)-4-methyl-5α-4-azapregnan-3-one;
20-(3-methoxybenzyloxy)methyl-4-methyl-5α-4-azapregnan-3-one;
17α-(carboethoxymethoxy)benzyl-4-methyl-5α-4-azaandrostan-3-one;
20-(4-(methylthio)benzyloxy)methyl-4-methyl-5α-4-azapregnan-3-one;
4-methyl-17-n-octylthiomethyl-5α-4-azaandrostan-3-one;
20-(t-butylthiomethyl)-4-methyl-5α-4-azapregnan-3-one;
17-(2-furfuryl)thiomethyl-4-methyl-5α-4-azaandrostan-3-one;
17-(geranyloxymethyl)-4-methyl-5α-4-azaandrostan-3-one;
4-methyl-20-(2-(n-nonylthio)ethyl)-5α-4-azapregnan-3-one;
20-(methylthiomethyl)-4-methyl-5α-4-azapregnan-3-one;
17-(4-(benzyloxy)benzyloxy)methyl-4-methyl-5α-4-azaandrostan-3-one;
20-(diphenylmethylthio)methyl-4-methyl-5α-4-azapregnan-3-one;
17-(3-(ethylthio)propyl)-4-methyl-5α-4-azaandrostan-3-one;
4-methyl-20-(phenylthiomethyl)-5α-4-azapregnan-3-one;
17-(ethylsulfonylmethyl)-4-methyl-5α-4-azaandrostan-3-one;
17-(4-ethoxybenzyloxy)methyl-4-methyl-5α-4-azaandrostan-3-one;

and pharmaceutically acceptable salts thereof.

12. The method of preventing premature labor according to claim 11 wherein the inhibitor of 5α-reductase type 1 is selected from:

3-oxo-4-aza-4,7β-dimethyl-16β-(4-chlorophenoxy)-5α-androstane, 3-oxo-4-aza-4,7β-dimethyl-16β-(phenoxy)-5α-androstane, and 3-oxo-4-aza-7-methyl-16β-(4-methylphenoxy)-5α-androst-1-ene, 4,7β-dimethyl-4-aza-5α-cholestan-3-one, and 7β,20-dimethyl-4-aza-5α-pregn-1-en-3-one;
or pharmaceutically acceptable salts thereof.

13. The method of preventing premature labor according to claim 9 wherein the inhibitor of 5α-reductase type 1 is a dual inhibitor of 5α-reductase type 1 and 5α-reductase type 2.

14. The method of preventing premature labor according to claim 13 wherein the inhibitor is selected from: those of structural formula IX:

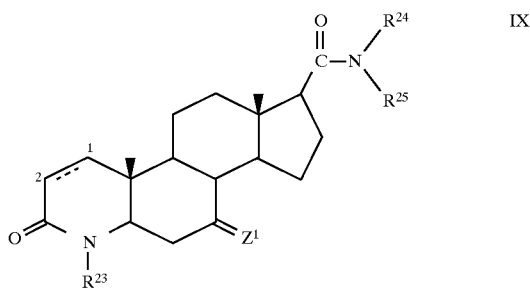

or a pharmaceutically acceptable salt or ester thereof, wherein: the $C_1$–$C_2$ bond designated "---" represents a single or double bond;

$R^{23}$ is selected from:
(1) —H,
(2) —$CH_3$ and
(3) —$CH_2CH_3$;

$Z^1$ is selected from:
(1) oxo,
(2) α-H and a β-substituent selected from:
(a) $C_{1-4}$ alkyl,
(b) $C_2$-4 alkenyl,
(c) —$CH_2$ COOH,
(d) —OH,
(e) —COOH,
(f) —COO ($C_{1-4}$ alkyl),
(g) —OCONR$^{26}$R$^{27}$ wherein
$R^{26}$ and $R^{27}$ are independently selected from
(i) —H,
(ii) —$C_{1-4}$ alkyl,
(iii) phenyl and
(iv) benzyl;
or $R^{26}$ and $R^{27}$ taken together with the nitrogen to which they are attached represent a 5–6 membered saturated heterocycle optionally containing one other heteroatom selected from —O—, —NH— and —S—;
(h) $C_{1-4}$ alkoxy,
(i) $C_{3-6}$ cycloalkoxy,
(j) —OC(O)R$^{28}$, wherein R$^{28}$ is $C_{1-6}$ alkyl or phenyl,
(k) halo,
(l) halo-$C_{1-2}$ alkyl,
(m) —$CF_3$, and
(n) $C_{3-6}$ cycloalkyl;
(3) =CHR$^{29}$;

(4) spirocyclopropane either unsubstituted or substituted with $R^{29}$;

$R^{24}$ is selected from —H and $C_{1-6}$ alkyl, either unsubstituted or substituted with one or more of aryl, heteroaryl, —COOH or —OH;

$R^{25}$ is —$C_{1-6}$ alkyl substituted with one or more of aryl, heteroaryl, —COOH, —OH or di-aryl amino; and $R^{29}$ is selected from —H and $C_{1-4}$ alkyl.

15. The method of preventing premature labor according to claim 13 wherein the inhibitor is selected from:

17β-N-(2,5-bis(trifluoromethyl))phenyl carbamoyl-4-aza-5α-androst-1-en-3-one;

N-(diphenylmethyl)-3-oxo-4-aza-7β-methyl-5α-androstane-17β-carboxamide;

N-(diphenylmethyl)-3-oxo-4-aza-7β-methyl-5α-androst-1-ene-17β-carboxamide;

N-(diphenylmethyl)-3-oxo-4-aza-4,7β-dimethyl-5α-androstane-17β-carboxamide; and

N-(methyl),N-(diphenylmethyl)-3-oxo-4-aza-4,7β-dimethyl-5α-androstane-17β-carboxamide.

16. The method of preventing preterm labor according to claim 9 wherein the mammalian subject is a female human.

17. A method of stopping labor preparatory to Cesarean delivery in a mammal in need thereof, comprising administering to the mammal a therapeutically effective amount of a 5α-reductase type 1 inhibitor.

18. A method for improving survival of a farm animal neonate comprising controlling the timing of parturition to effect delivery of the neonate during daylight hours by administering to the farm animal which is expected to deliver the neonate within 24 hours a therapeutically effective amount of a 5α-reductase type 1 inhibitor.

19. A pharmaceutical composition comprising a pharmaceutically acceptable carrier, a therapeutically effective amount of a 5α-reductase type 1 inhibitor and a therapeutically effective amount of another tocolytic agent selected from:

(a) a β$_2$-adrenergic agonist,
(b) magnesium sulfate,
(c) ethanol,
(d) an oxytocin receptor antagonist,
(e) a calcium transport blocker,
(f) a prostaglandin synthesis inhibitor,
(g) a nitric oxide donor,
(h) a phosphodiesterase inhibitor, and
(i) a progestin.

20. The pharmaceutical composition according to claim 19 wherein:

(1) the β$_2$-adrenergic agonist is selected from:
(a) ritodrine,
(b) salbutamol,
(c) terbutaline, and
(d) albuterol;
(2) the oxytocin antagonist is: atosiban;
(3) the calcium transport blocker is selected from:
(a) nicardipine, and
(b) nifedipine;
(4) the prostaglandin synthesis inhibitor is: indomethacin;
(5) the nitric oxide donor is selected from:
(a) nitroglycerine, and
(b) S-nitroso-N-acetyl penicillamine; and
(6) the progestin is progesterone.

21. A pharmaceutical composition for vaginal administration comprising an inhibitor of 5α-reductase type 1 and a pharmaceutically acceptable carrier.

22. The pharmaceutical composition for vaginal administration according to claim 21 wherein the inhibitor of 5α-reductase type 1 is selected from:

3-oxo-4-aza-4,7β-dimethyl-16β-(4-chlorophenoxy)-5α-androstane, 3-oxo-4-aza-4,7β-dimethyl-16β-(phenoxy)-5α-androstane, and 3-oxo-4-aza-7-methyl-16β-(4-methylphenoxy)-5α-androst-1-ene, 4,7β-dimethyl-4-aza-5α-cholestan-3-one, and 7β,20-dimethyl-4-aza-5α-pregn-1-en-3-one; or pharmaceutically acceptable salts thereof.

23. The pharmaceutical composition for vaginal administration according to claim 21 which is a suppository.

* * * * *